United States Patent [19]
Gonez et al.

[11] Patent Number: 5,821,075
[45] Date of Patent: Oct. 13, 1998

[54] NUCLEOTIDE SEQUENCES FOR NOVEL PROTEIN TYROSINE PHOSPHATASES

[75] Inventors: Leonel Jorge Gonez, Hughesdale, Australia; Jan Saras, Upsala, Sweden; Lana Claesson-Welsh, Upsala, Sweden; Carl-Henrik Heldin, Upsala, Sweden

[73] Assignee: The Ludwig Institute for Cancer Research, New York, N.Y.

[21] Appl. No.: 596,291

[22] PCT Filed: Sep. 1, 1994

[86] PCT No.: PCT/US94/09943

§ 371 Date: Aug. 9, 1996

§ 102(e) Date: Aug. 9, 1996

[87] PCT Pub. No.: WO95/06735

PCT Pub. Date: Mar. 9, 1995

Related U.S. Application Data

[63] Continuation of Ser. No. 115,573, Sep. 1, 1993, abandoned.

[51] Int. Cl.$^6$ .............................. C12Q 1/42; C12N 15/55; C07K 14/435

[52] U.S. Cl. ........................... 435/21; 435/196; 435/7.21; 435/69.1; 435/320.1; 435/18; 536/23.5; 530/350

[58] Field of Search ........................... 536/23.5; 435/195, 435/196, 7.2, 7.21, 21, 69.1, 320.1, 18; 530/350

[56] References Cited

FOREIGN PATENT DOCUMENTS

| | | |
|---|---|---|
| 2086377 | 8/1993 | Canada. |
| WO91/13173 | 9/1991 | WIPO. |

OTHER PUBLICATIONS

Lewin, Science, 237, 1570, Sep. 1987.

Reeck et al., Cell, 50, 667, Aug. 1987.

Saras et al., "Cloning and characterization of PTPL1, a protein tyrosine phosphatase with similarities to cytoskeletal–associated proteins", Sep. 30, 1994, pp. 24082–24089, J.Biol.Chem., vol. 269, No. 39.

Maekawa et al., "Molecular cloning of a novel protein–tyrosine phosphatase containing a membrane–binding domain and GLGF repeats", Jan. 10, 1994, pp. 200–206, Febs Letters, vol. 337.

Yung et al., "Differential expression of protein tyrosine phosphatases in primary human brain tumors", Mar. 1993, p. 527, Proc. Am. Assoc. Cancer Research, vol. 34.

Lombroso et al., "Characterization of a protein–tyrosine phosphatase enriched in striatum",Aug. 1991, pp. 7242–7246, Proc. Natl. Acad. Sciences, vol. 88.

Toews et al., "Evidence for involvement of tyrosine phosphorylation in serum–induced sensitization of cyclic AMP accumulation in C62B rat glioma cells", 1992, p. A1075, Faseb J., vol. 6, No. 4.

Yang et al., "Isolation of a cDNA clone encoding a human protein–tyrosine phosphatase with homology to the cytoskeletal–associated proteins band 4.1, ezrin and talin", 1991, pp. 5949–5953, Proc. Natl. Acad. Sciences, vol. 88.

Gu et al., "Identification cloning, and expression of cytosolic megakaryocyte protein–tyrosine–phosphatase with sequence homology to cytoskeletal protein 4.1", 1991, pp. 5867–5871, Proc. Natl. Acad Sciences, vol. 88.

Adachi et al., "Molecular cloning and chromosomal mapping of a human protein–tyrosine phosphatase LC–PTP", Aug. 14, 1992, pp. 1607–1615, Biochem. Biophys. Res. Commun., vol. 186, No. 3.

*Primary Examiner*—Sally Teng
*Attorney, Agent, or Firm*—Wolf, Greenfield & Sacks, P.C.

[57] ABSTRACT

The invention relates to the cloning of two novel protein tyrosine phosphatases. Nucleic acid sequences encoding these phosphatases (PTPL1 and GLM-2) as well as antisense sequences are also provided. The recombinantly produced PTPL1 and GLM-2 proteins also are provided, as well as antibodies to these proteins. Methods relating to isolating the phosphatases, using the nucleic acid sequences, and using the phosphatases also are provided.

12 Claims, 5 Drawing Sheets

Fig. 1

```
MEHYLPARVME--KLDLSYIKEELPKLHNTYVGASEKETELEFLKVCQRLTEY    PTPL1
SERLIPQRVMDQHKLTRDQWEDRIQVWHAEHRGMLKDNAMLEYLKIAQDLEMY    Ezrin
DFKLAPNQ---------TKELEEKVMELHKSYRSMTPAQADLEFLENAKKLSMY   Band 4.1
DYSFIPNQ---------PQDFEKEIAKLHQQHIGLSPAEAEFNYLNTARTLELY   PTPase MEG
DSHFIPDQ---------NEDFLTKVESLHEQHSGLKQSEAESCYINIARTLDFY   PTPH1

GVHFHRVHPEKKSQTGILLGVCSKGVLVFEVHNGVRTLVLRFPWRETKKISFS    PTPL1
GINYFEIK---NKKGTDLWLGVDALGLNIYEKDDKLTPKI-GFPWSEIRNISFN   Ezrin
GVDLHKAK---DLEGVDIILGVCSSGLLVYKDKLRINR----FPWPKVLKISYK   BAND 4.1
GVEFHYAR---DQSNNEIMIGVMSGGILIYKNRVRMNT----FPWLKIVKISFK   PTPase MEG
GVELHSGR---DLHNLDLMIGIASAGVAVYRKYICTSF----YPWVNILKISFK   PTPH1

KKKITLQNTSDGIKH----GFQTDNSKICQYLLHLCSYQHKFQLQMR---AR    PTPL1
DKKFVIKP----IDKKAPDFVFYAPRLRINKRILQLCMGNHELYMRRRKPDTI    Ezrin
RSSFFIKIRPGEQEQYESTIGFKLPSYRAAKKLWKVCVEHHTFF-RLTSTDTI    Band 4.1
CKQFFIQLRKELHESRETLLGFNMVNYRACKNLWKACVEHHTFF-RLDRPLPP    PTPase MEG
RKKFFIHQRQKQAESREHIVAFNMLNYRSCKNLWKSCVEHHTFF-QAKKLLPQ    PTPH1
```

Fig. 1 cont.

| | | | | | | |
|---|---|---|---|---|---|---|
| PTPL1 | 1 | DAKYGLGFQIIGGEK | MGRLDLGIFISSVAPGGPADFH | GCLKPGDRLISV | NSV | SLEGVSEHAAIEILQNAPEDVTLVI |
| PTPL1 | 2 | KNDNSLOISVTGGVN | TSVRHGGIYVKAVIPQGAAAESD | GRIHKGDRVLAV | NGV | SLEGATEKQAVETLRNTGQVVHLLL |
| PTPL1 | 3 | KNSSGLGFSFSREDNLIPEQINASIVRVKKLFAGQPAAES | | GKIDVGDVILKV | NGA | SLKGLSQQEVISALRGTAPEVFLLL |
| PTPL1 | 4 | SEKASLGFTVTKGNQ | RIGCYVHDVI QDPAKSD | GRLKPGDRLIKV | NDT | DVTNMTHTDAVNLLRAASKTVRLVI |
| PTPL1 | 5 | CNKBELGFSLCGGHD | SLYQVVIISDINPRSVAAIE | GNLQLLDVIHYV | NGV | STQGMTLEEVNRALDMSLPSLVLKA |
| PTPH1 | | DEDGKPGFNLKGGVD | QKNPLVVSRINPSSPADTCIPKLNEGDQIVLI | | NGR | DISEHTHDQVVMFIKASRESHSREL |
| PTPase MEG | | DENGRFGFNVKGGYD | QKMPVIVSRVAPQTPADLCVPRLNEGDQVVLI | | NGR | DIAEHTHDQVVLFIKASCERHSGEL |
| dlg-A | 1 | RGNSGLGFSIAGGTDNPHI | GTDTSIYITKLISGGAAAAD | GRLSINDIIVSV | NDV | SVVDVPHASAVDALKKAGNVVKLHV |
| dlg-A | 2 | KGGKGLGFSIAGGIGNQHI | PGDNGIYVTKLTDGGRAQVD | GRLSIGDKLIAVRTNGSEKNLENVTHELAVATLKSITDKVTLII | | | |
| dlg-A | 3 | KGPQGLGFNIVGGED | GQGIYVSFILAGGPADLG | SELKRGDQLLSV | NNV | NLTHATHEEAAQALKTSGGVVTLLA |
| PSD-95 | 1 | RGNSGLGFSIAGGTDNPHI | GDDPSIFITKIIPGGAAAQD | GRLRVNDSILFV | NEV | DVREVTHSAAVEALKEAGSIVRLYV |
| PSD-95 | 2 | KGPKGLGFSIAGGVGNQHI | PGDNSIYVTKIIEGGAAHKD | GRLQIGDKILAV | NSV | GLEDVMHEDAVAALKNTYDVVYLKV |
| PSD-95 | 3 | RGSTGLGFNIVGGED | GEGIFISFILAGGPADLS | GELRKGDQILSV | NGV | DLRNASHEQAAIALKNAGQTVTIIA |
| 220-KD | 1 | HRAPGFGIAISGGRDNPHFQSGETSIVISDVLKGGPAB | | GQLQENNRVAMV | NGV | SMDNVEHAFAVQQLRKSGKNAKITI |
| 220-KD | 2 | RKNEEYGLRPASH | IFVKEISQDSLAARD | GDIQEGDVVLKI | NGT | VTENMSLTDAKTLIERSKGKLKMVV |
| 220-KD | 3 | RKGDSVGLRLAGGND | VGIFVAGVLEDSPAAKE | G LEEGDQILRV | NNV | DFTNIIREEAVLFLLDLPKGEEVTI |
| p55 | | VTEEPMGITLKLNEK | QSCTVARILHGGMIHRQ | GSLHVGDEILEI | NGT | NVTNHSVDQLQKAMKETKGMISLKV |
| NOS | | RKVGGLGFLVKERVS | PKKVIISDLIRGGAAEQS | GLIQAGDIILAV | NDR | PLVDLSYDSALEVLRGIASETHVVL |
| 0118 (ROS) | | EDHEOLGISITGGLE | HGVPILISGIHPGQPADRC | GGLHVGDAILAV | NGV | NLRDTLHLGAVTILSQQRGEIEFEV |

Fig. 2

NUCLEOTIDE SEQUENCES FOR NOVEL PROTEIN TYROSINE PHOSPHATASES

This application is a national stage application under 35 U.S.C. §371 of PCT/US94/09943, filed Sep. 1, 1993, which is a continuation of U.S. application Ser. No. 08/115,573, filed Sep. 1, 1993, now abandoned.

FIELD OF THE INVENTION

This invention relates to the isolation and cloning of nucleic acids encoding two novel protein tyrosine phosphatases (PTPs). Specifically, the present invention relates to the isolation and cloning of two PTPs from human glioblastoma cDNA which have been designated PTPL1 and GLM-2. The present invention provides isolated PTP nucleic acid sequences; isolated PTP anti-sense sequences; vectors containing such nucleic acid sequences; cells, cell lines and animal hosts transformed by a recombinant vector so as to exhibit increased, decreased, or differently regulated expression of the PTPs; isolated probes for identifying sequences substantially similar or homologous to such sequences; substantially pure PTP proteins and variants or fragments thereof; antibodies or other agents which bind to these PTPs and variants or fragments thereof; methods of assaying for activity of these PTPs; methods of assessing the regulation of PTPL1 or GLM-2; and methods of identifying and/or testing drugs which may affect the expression or activity of these PTPs.

BRIEF DESCRIPTION OF THE BACKGROUND ART

Protein tyrosine phosphorylation plays an essential role in the regulation of cell growth, proliferation and differentiation (reviewed in Hunter, T. (1987) Cell 50:823–8291). This dynamic process is modulated by the counterbalancing activities of protein tyrosine kinases (PTKS) and protein tyrosine phophatases (PTPs). The recent elucidation of intracellular signaling pathways has revealed important roles for PTKS. Conserved domains like the Src homology 2 (SH2) (Suh, P.-G., et al., (1988) Proc. Natl. Acad Sci. (USA) 85,5419–5423) and the Src homology 3 (SH3) (Mayer, B. J., et al., (1988) Nature 352:272–275) domains have been found to determine the interaction between activated PTKS and signal transducing molecules (reviewed in Pawson, T., and Schiessinger, J. (1993) Current Biol. 3:434–442; Koch, C. A., et al., (1991) Science 252:668–674). The overall effect of such protein interactions is the formation of signaling cascades in which phosphorylation and dephosphorylation of proteins on tyrosine residues are major events. The involvement of PTPs in such signaling cascades is beginning to emerge from studies on the regulation and mechanisms of action of several representatives of this broad family of proteins.

Similarly to PTKS, PTPs can be classified according to their secondary structure into two broad groups, i.e. cytoplasmic and transmembrane molecules (reviewed in Charbonneau, H., and Tonks, N. K. (1992) Annu. Rev. Cell Biol. 8:463–493; Pot, D. A., and Dixon, J. E. (1992) Biochim. Biophys. Acta 1136:35–43). Transmembrane PTPs have the structural organization of receptors and thus the potential to initiate cellular signaling in response to external stimuli. These molecules are characterized by the presence of a single transmembrane segment and two tandem PTP domains; only two examples of transmembrane PTPs that have single PTP domains are known, HPTP-P (Krueger, N. X., et al., (1990) EMBO J. 9:3241–3252) and DPTP10D (Tian, S. -S., et al., (1991) Cell 67:675–685).

Nonreceptor PTPs display a single catalytic domain and contain, in addition, non-catalytic amino acid sequences which appear to control intracellular localization of the molecules and which may be involved in the determination of substrate specificity (Mauro, L. J., and Dixon, J. E. (1994) TIBS 19:151–155) and have also been suggested to be regulators of PTP activity (Charbonneau, H., and Tonks, N. K. (1992) Annu. Rev. Cell Biol. 8:463–493). PTP1B (Tonks, N. K., et al., (1988) J. Biol. Chem. 263:6731–6737) is localized to the cytosolic face of the endoplasmic reticulum via its C-terminal 35 amino acids (Frangioni, J. V., et al., (1992) Cell 68:545–560). The proteolytic cleavage of PTP1B by the calcium dependent neutral protease calpain occurs upstream from this targeting sequence, and results in the relocation of the enzyme from the endoplasmic reticulum to the cytosol; such relocation is concomitant with a two-fold stimulation of PTP1B enzymatic activity (Frangioni, J. V., et al., (1993) EMBO J. 12:4843–4856). Similarly, the 11 kDa C-terminal domain of T-cell PTP (Cool, D. E., et al., (1989) Proc. Natl. Acad. Sci. (USA) 86:5257–5261) has also been shown to be responsible for enzyme localization and functional regulation (Cool, D. E., et al., (1990) Proc. Natl. Acad. Sci. (USA) 87:7280–7284; Cool, D. E., et al., (1992) Proc. Natl. Acad. Sci. (USA) 89:5422–5426).

PTPs containing SH2 domains have been described including PTP1C (Shen, S. -H., et al., (1991) Nature 352:736–739), also named HCP (Yi, T., et al., (1992) Mol. Cell. Biol. 12:836–846), SHP (Matthews, R. J., et al., (1992) Mol. Cell. Biol 12:2396–2405) or SH-PTP1 (Plutzky, J., et al., (1992) Proc. Natl. Acad. Sci. (USA) 89:1123–1127), and the related phosphatase PTP2C (Ahmad, S., et al., (1993) Proc. Nati. Acad. Sci. (USA) 90:2197–2201), also termed SH-PTP2 (Freeman Jr., R. M., et al., (1992) Proc. Natl. Acad. Sci. (USA) 89:11239–11243), SH-PTP3 (Adachi, M., et al., (1992) FEBS Letters 314:335–339), PTP1D (Vogel, W., et al., (1993) Science 259:1611–1614) or Syp (Feng, G.-S., et al., (1993) Science 259:1607–1611). The Drosophila csk gene product (Perkins, L. A., et al., (1992) Cell 70:225–236) also belongs to this subfamily. PTP1C has been shown to associate via its SH2 domains with ligand-activated c-Kit and CSF-1 receptor PTKs (Yi, T., and Ihle, J. N. (1993) Mol. Cell. Biol. 13:3350–3358; Young, Y.-G., et al., (1992) J. Biol. Chem. 267:23447–23450) but only association with activated CSF-1 receptor is followed by tyrosine phosphorylation of PTP1C. Syp interacts with and is phosphorylated by the ligand activated receptors for epidermal growth factor and platelet-derived growth factor (Feng, G.-S., et al., (1993) Science 259:1607–1611). Syp has also been reported to associate with tyrosine phosphorylated insulin receptor substrate 1 (Kuhne, M. R., et al., (1993) J. Biol. Chem. 268:11479–11481).

Two PTPs have been identified, PTPH1 (Yang, Q., and Tonks, N. K. (1991) Proc. Natl. Acad. Sci. (USA) 88:5949–5953) and PTPase MEG (Gu, M., et al., (1991) Proc. Natl. Acad. Sci. (USA) 88:5867–5871), which contain a region in their respective N-terminal segments with similarity to the cytoskeletal- associated proteins band 4.1 (Conboy, J., et al., (1986) Proc. Natl. Acad. Sci. (USA) 83:9512–9516), ezrin (Gould, K. L., et al., (1989) EMBO J. 8:4133–4142), talin (Rees, D. J. G., et al., (1990) Nature 347:685–689) and radixin (Funayama, N., et al., (1991) J. Cell Biol. 115:1039–1048). The function of proteins of the band 4.1 family appears to be the provision of anchors for cytoskeletal proteins at the inner surface of the plasma membrane (Conboy, J., et al., (1986) Proc. Natl. Acad. Sci. (USA) 83:9512–9516; Gould, K. L., et al., (1989) EMBO J.

8:4133–4142). It has been postulated that PTPH1 and PTPase MEG would, like members of this family, localize at the interface between the plasma membrane and the cytoskeleton and thereby be involved in the modulation of cytoskeletal function (Tonks, N. K., et al., (1991) *Cold Spring Harbor Symposia on Quantitative Biology* LVI:265–273).

The interest in studying PTKs and PTPs is particularly great in cancer research. For example, approximately one third of the known oncogenes include PTKs (Hunter, T. (1989) In *Oncogenes and Molecular Origins of Cancer*, R. Weinberq, Ed., Coldspring Harbor Laboratory Press, New York). In addition, the extent of tyrosine phosphorylation closely correlates with the manifestation of the transformed phenotype in cells infected by temperature-sensitive mutants of rous sarcoma virus. (Sefton, B., et al., (1980) *Cell* 20:807–816) Similarly, Brown-Shirner and colleagues demonstrated that over-expression of PTP1B in 3T3 cells suppressed the transforming potential of oncogenic neu, as measured by focus formation, anchorage-independent growth and tumorigenicity (Brown-Shirner, S., et al., (1992) *Cancer Res.* 52:478–482). Because they are direct antagonists of PTK activity, the PTPs also may provide an avenue of treatment for cancers caused by excessive PTK activity. Therefore, the isolation, characterization and cloning of various PTPs is an important step in developing, for example, gene therapy to treat PTK oncogene cancers.

SUMMARY OF THE INVENTION

The present invention is based upon the molecular cloning of previously uncloned and previously undisclosed nucleic acids encoding two novel PTPs. The disclosed sequences encode PTPs which we have designated PTPL1 and GLM-2. (PTPL1 was previously designated GLM-1 in U.S. patent application Ser. No. 08/115,573 filed Sep. 1, 1993.) In particular the present invention is based upon the molecular cloning of PTPL1 and GLM-2 PTP sequences from human glioblastoma cells. The invention provides isolated cDNA and RNA sequences corresponding to PTPL1 and GLM-2 transcripts and encoding the novel PTPs. In addition, the present invention provides vectors containing PTPL1 or GLM-2 cDNA sequences, vectors capable of expressing PTPL1 or GLM-2 sequences with endogenous or exogenous promoters, and hosts transformed with one or more of the above-mentioned vectors. Using the sequences disclosed herein as probes or primers in conjunction with such techniques as PCR cloning, targeted gene walling, and colony/plaque hybridization with genomic or cDNA libraries, the invention further provides for the isolation of allelic variants of the disclosed sequences, endogenous PTPL1 or GLM-2 regulatory sequences, and substantially similar or homologous PTPL1 or GLM-2 DNA and RNA sequences from other species including mouse, rat, rabbit and non-human primates.

The present invention also provides fragments and variants of isolated PTPL1 and GLM-2 sequences, fragments and variants of isolated PTFL1 or GLM-2 RNA, vectors containing variants or fragments of PTPL1 or GLM-2 sequences, vectors capable of expressing variants or fragments of PTPL1 or GLM-2 sequences with endogenous or exogenous regulatory sequences, and hosts transformed with one or more of the above-mentioned vectors. The invention further provides variants or fragments of substantially similar or homologous PTPL1 and GLM-2 DNA and RNA sequences from species including mouse, rat, rabbit and non-human primates.

The present invention provides isolated PTPL1 and GLM-2 anti-sense DNA, isolated PTPL1 and GLM-2 anti-sense RNA, vectors containing PTPL1 or GLM-2 anti-sense DNA, vectors capable of expressing PTPL1 or GLM-2 anti-sense DNA with endogenous or exogenous promoters, and hosts transformed with one or more of the above-mentioned vectors. The invention further provides the related PTPL1 or GLM-2 anti-sense DNA and anti-sense RNA sequences from other species including mouse, rat, rabbit and non-human primates The present invention also provides fragments and variants of isolated PTPL1 and GLM-2 anti-sense DNA, fragments and variants of isolated PTPL1 and GLM-2 anti-sense RNA, vectors containing fragments or variants of PTPL1 and GLM-2 anti-sense DNA, vectors capable of expressing fragments or variants of PTPL1 and GLM-2 anti-sense DNA with endogenous or exogenous promoters, and hosts transformed with one or more of the above-mentioned vectors. The invention further provides fragments or variants of the related PTPL1 and GLM-2 anti-sense DNA and PTPL1 and GLM-2 anti-sense RNA sequences from other species including mouse, rat, rabbit and non-human primates.

Based upon the sequences disclosed herein and techniques well known in the art, the invention also provides isolated probes useful for detecting the presence or level of expression of a sequence identical, substantially similar or homologous to the disclosed PTPL1 and GLM-2 sequences. The probes may consist of the PTPL1 and GLM-2 DNA, RNA or anti-sense sequences disclosed herein. The probe may be labeled with, for example, a radioactive isotope; immobilized as, for example, on a filter for Northern or Southern blotting; or may be tagged with any other sort of marker which enhances or facilitates the detection of binding. The probes may be oligonucleotides or synthetic oligonucleotide analogs.

The invention also provides substantially pure PTPL1 and GLM-2 proteins. The proteins may be obtained from natural sources using the methods disclosed herein or, in particular, the invention provides substantially pure PTPL1 and GLM-2 proteins produced by a host cell or transgenic animal transformed by one of the vectors disclosed herein.

The invention also provides substantially pure variants and fragments of PTPL1 and GLM-2 proteins. Using the substantially pure PTPL1 or GLM-2 protein or variants or fragments of the PTPL1 or GLM-2 protein which are disclosed herein, the present invention provides methods of obtaining and identifying agents capable of binding to either PTPL1 or GLM-2. Specifically, such agents include antibodies, peptides, carbohydrates and pharmaceutical agents. The agents may include natural ligands, co-factors, accessory proteins or associated peptides, modulators, regulators, or inhibitors. The entire PTPL1 or GLM-2 protein may be used to test or develop such agents or variants or fragments thereof may be employed. In particular, only certain domains of the PTPL1 or GLM-2 protein may be employed. The invention further provides detectably labeled, immobilized and toxin-conjugated forms of these agents.

The present invention also provides methods for assaying for PTPL1 or GLM-2 PTP activity. For example, using the PTPL1 and GLM-2 anti-sense probes disclosed herein, the presence and level of either PTPL1 or GLM-2 expression may be determined by hybridizing the probes to total or selected mRNA from the cell or tissue to be studied. Alternatively, using the antibodies or other binding agents disclosed herein, the presence and level of PTPL1 or GLM-2 protein may be assessed. Such methods may, for example, be employed to determine the tissue-specificity of PTPL1 or GLM-2 expression.

The present invention also provides methods for assessing the regulation of PTPL1 or GLM-2 function. Such methods include fusion of the regulatory regions of the PTPL1 or GLM-2 nucleic acid sequences to a marker locus, introduction of this fusion product into a host cell using a vector, and testing for inducers or inhibitors of PTPL1 or GLM-2 by measuring expression of the marker locus. In addition, by using labeled PTPL1 and GLM-2 anti-sense transcripts, the level of expression of PTPL1 or GLM-2 mRNA may be ascertained and the effect of various endogenous and exogenous compounds or treatments on PTPL1 or GLM-2 expression may be determined. Similarly, the effect of various endogenous and exogenous compounds and treatments on PTPL1 or GLM-2 expression may be assessed by measuring the level of either PTPL1 or GLM-2 protein with labeled antibodies as disclosed herein.

The present invention provides methods for efficiently testing the activity or potency of drugs intended to enhance or inhibit PTPL1 or GLM-2 expression or activity. In particular, the nucleic acid sequences and vectors disclosed herein enable the development of cell lines and transgenic organisms with increased, decreased, or differently regulated expression of PTPL1 or GLM-2. Such cell lines and animals are useful subjects for testing pharmaceutical compositions.

The present invention further provides methods of modulating the activity of PTPL1 and GLM-2 PTPs in cells. Specifically, agents and, in particular, antibodies which are capable of binding to either PTPL1 or GLM-2 PTP are provided to a cell expressing PTPL1 or GLM-2. The binding of such an agent to the PTP can be used either to activate or inhibit the activity of the protein. In addition, PTPL1 and GLM-2 anti-sense transcripts may be administered such that they enter the cell and inhibit translation of the PTPL1 or GLM-2 mRNA and/or the transcription of PTPL1 or GLM-2 nucleic acid sequences. Alternatively, PTPL1 or GLM-2 RNA may be administered such that it enters the cell, serves as a template for translation and thereby augments production of PTPL1 or GLM-2 protein. In another embodiment, a vector capable of expressing PTPL1 or GLM-2 mRNA transcripts or PTPL1 or GLM-2 anti-sense RNA transcripts is administered such that it enters the cell and the transcripts are expressed.

BRIEF DESCRIPTION OF THE DRAWINGS

FIG. 1. Comparison of PTPL1 SEQ ID NO:11 with proteins of the band 4.1 superfamily (ezrin, -SEQ ID NO:12; band 4.1, -SEQ ID NO:13. The alignment was done using the Clustal V alignment program (Fazioli, F., et al., (1993) Oncogene 8:1335–1345). Identical amino acid residues conserved in two or more sequences, are boxed. A conserved tyrosine residue, which in ezrin has been shown to be phosphorylated by the epidermal growth factor receptor, is indicated by an asterisk FIG. 2. Comparison of amino acid sequences of GLGF-repeats. The alignment was done manually. Numbers of the GLGF-repeats are given starting from the N-terminus of the protein. Residues conserved in at least eight (42%) repeats are showed in bold letters. Five repeats are found In PTPL1 (SEQ ID NO:16, SEQ ID NO:17, SEQ ID NO:18, SEQ ID NO:19, and SEQ ID NO:20), three are found in the guanylate kinases, dlg-A gene product (SEQ ID NO:23, SEQ ID NO:24, and SEQ ID NO:25), PSD-95 (SEQ ID NO:26, SEQ ID NO:27, and SEQ ID NO:28) and the 220-kDa protein (SEQ ID NO:29, SEQ ID NO:30, and SEQ ID NO:31). One GLGF-repeat is found in the guanylate kinase p55 (SEQ ID NO:32), in the PTPs PTPH1 (SEQ ID NO:21) and PTPase MEG (SEQ ID NO:22), and in nitric oxide synthase (NOS, SEQ ID NO:33). One repeat is also found in an altered ros1 transcript from the glioma cell line U-118MG(SEQ ID NO:34).

DETAILED DESCRIPTION OF THE INVENTION DEFINITIONS

Figure 3:
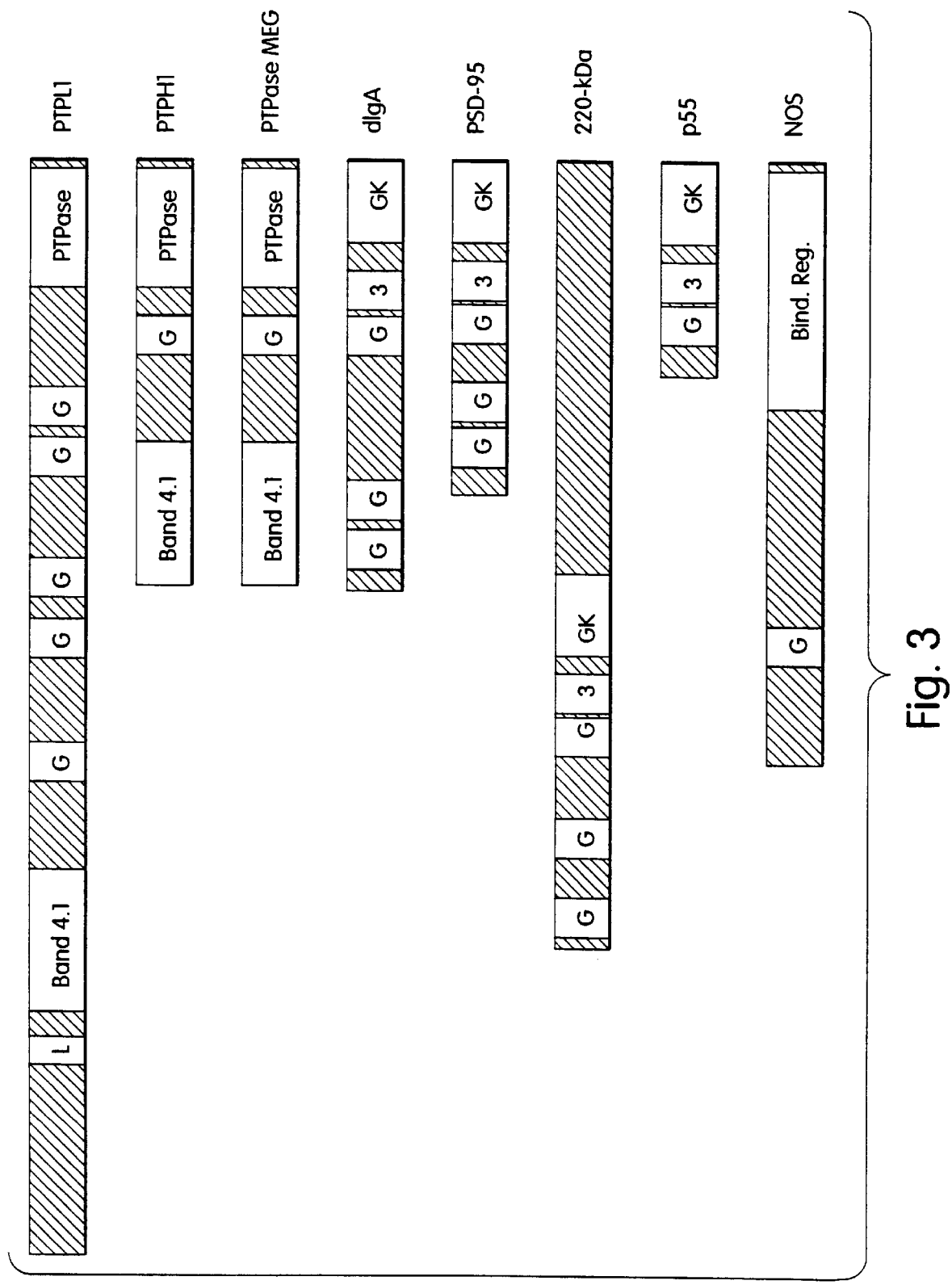
FIG. 3. Schematic diagram illustrating the domain strucure of PTPL1 and other GLGF-repeat containing proteins. Domains and motifs indicated in the figure are L, leucine zipper motif: Band 4.1, band 4.1-like domain; G, GLGF-repeat; PTPase, catalytic PTPase domain; 3, SH3 domain; GK, guanylate kinase domain, Bind. Reg., co-enzyme binding region.

In the description that follows, a number of terms used in biochemistry, molecular biology, recombinant DNA (rDNA) technology and immunology are extensively utilized. In addition, certain new terms are introduced for greater ease of exposition and to more clearly and distinctly point out the subject matter of the invention. In order to provide a clear and consistent understanding of the specification and claims, including the scope to be given such terms, the following definitions are provided.

Gene. A gene is a nucleic acid sequence including a promoter region operably joined to a coding sequence which may serve as a template from which an RNA molecule may be transcribed by a nucleic acid polymerase. A gene contains a promoter sequence to which the polymerase binds, an initiation sequence which signals the point at which transcription should begin, and a termination sequence which signals the point at which transcription should end. The gene also may contain an operator site at which a repressor may bind to block the polymerase and to prevent transcription and/or may contain ribosome binding sites, capping signals, transcription enhancers and polyadenylation signals. The promoter, initiation, termination and, when present, operator sequences, ribosome binding sites, capping signals, transcription enhancers and polyadenylation signals are collectively referred to as regulatory sequences. Regulatory sequences 5' of the transcription initiation codon are collectively referred to as the promoter region. The sequences which are transcribed into RNA are the coding sequences. The RNA may or may not code for a protein. RNA that codes for a protein is processed into messenger RNA (mRNA). Other RNA molecules may serve functions or uses without ever being translated into protein. These include ribosomal RNA (rRNA), transfer RNA (tRNA), and the anti-sense RNAs of the present invention. In eukaryotes, coding sequences between the translation start codon (ATG) and the translation stop codon (TAA, TGA, or TAG) may be of two types: exons and introns. The exons are included in processed mRNA transcripts and are generally translated into a peptide or protein. Introns are excised from the RNA as it is processed into mature mRNA and are not translated into peptide or protein. As used herein, the word gene embraces both the gene including its introns, as may be obtained from genomic DNA, and the gene with the introns excised from the DNA, as may be obtained from cDNA.

Anti-sense DNA is defined as DNA that encodes anti-sense RNA and anti-sense RNA is RNA that is complementary to or capable of selectively hybridizing to some specified RNA transcript. Thus, anti-sense RNA for a particular gene would be capable of hybridizing with that gene's RNA transcript in a selective manner. Finally, an anti-sense gene is defined as a segment of anti-sense DNA operably joined to regulatory sequences such that the sequences encoding the anti-sense RNA may be expressed.

cDNA. Complementary DNA or cDNA is DNA which has been produced by reverse transcription from mature mRNA. In eukaryotes, sequences in RNA corresponding to introns in a gene are excised during mRNA processing. cDNA sequences, therefore, lack the intron sequences present in the genomic DNA to which they correspond. In addition, cDNA sequences will lack the regulatory sequences which are not transcribed into RNA. To create a functional cDNA gene, therefore, the cDNA sequence must be operably joined to a promoter region such that transcription may occur.

Operably Joined. A coding sequence and a promoter region are said to be operably joined when they are covalently linked in such a way as to place the expression or transcription of the coding sequence under the influence or control of the promoter region. If it is desired that the coding sequences be translated into a functional protein, two DNA sequences are said to be operably joined if induction of promoter function results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

If it is not desired that the coding sequence be eventually expressed as a protein or polypeptide, as in the case of anti-sense RNA expression, there is no need to ensure that the coding sequences and promoter region are joined without a frame-shift. Thus, a coding sequence which need not be eventually expressed as a protein or polypeptide is said to be operably joined to a promoter region if induction of promoter function results in the transcription of the RNA sequence of the coding sequences.

The precise nature of the regulatory sequences needed for gene expression may vary between species or cell types, but shall in general include, as necessary, 5' non-transcribing and 5' non-translating sequences involved with initiation of transcription and translation respectively, such as a TATA box capping sequence, CAAT sequence, and the like. Especially, such 5' non-transcribing regulatory sequences will include a promoter region which includes a promoter sequence for transcriptional control of the operably joined gene. Such transcriptional control sequences may also include enhancer sequences or upstream activator sequences, as desired.

Vector. A vector may be any of a number of nucleic acid sequences into which a desired sequence may be inserted by restriction and ligation. Vectors are typically composed of DNA although RNA vectors are also available. Vectors include plasmids, phage, phasmids and cosmids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to a promoter region and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques.

Fragment. As used herein, the term "fragment" means both unique fragments and substantially characteristic fragments. As used herein, the term "fragment" is not to be construed according to standard dictionary definitions.

Substantially Characteristic Fragment. A "substantially characteristic fragment" of a molecule, such as a protein or nucleic acid sequence, is meant to refer to any portion of the molecule sufficiently rare or sufficiently characteristic of that molecule so as to identify it as derived from that molecule or to distinguish it from a class of unrelated molecules. A single amino acid or nucleotide, or a sequence of only two or three, cannot be a substantially characteristic fragment because all such short sequences occur frequently in nature.

A substantially characteristic fragment of a nucleic acid sequence is one which would have utility as a probe in identifying the entire nucleic acid sequence from which it is derived from within a sample of total genomic or cDNA. Under stringent hybridization conditions, a substantially characteristic fragment will hybridize only to the sequence from which it was derived or to a small class of substantially similar related sequences such as allelic variants, heterospecific homologous loci, and variants with small insertions, deletions or substitutions of nucleotides or nucleotide analogues. A substantially characteristic fragment may, under lower stringency hybridization conditions, hybridize with non-allelic and non-homologous loci and be used as a probe to find such loci but will not do so at higher stringency.

A substantially characteristic fragment of a protein would have utility in generating antibodies which would distinguish the entire protein from which it is derived, an allelomorphic protein or a heterospecific homologous protein from a mixture of many unrelated proteins.

It is within the knowledge and ability of one ordinarily skilled in the art to recognize, produce and use substantially characteristic fragments of nucleic acid sequences and proteins as, for example, probes for screening DNA libraries or epitopes for generating antibodies.

Unique Fragment. As used herein, a unique fragment of a protein or nucleic acid sequence is a substantially characteristic fragment not currently known to occur elsewhere in nature (except in allelic or heterospecific homologous variants, i.e. it is present only in the PTPL1 or GLM-2 PTP or a PTPL1 or GLM-2 PTP "homologue"). A unique fragment will generally exceed 15 nucleotides or 5 amino acid residues. One of ordinary skill in the art can identify unique fragments by searching available computer databases of nucleic acid and protein sequences such as Genbank (Los Alamos National Laboratories, USA), SwissProt or the National Biomedical Research Foundation database. A unique fragment is particularly useful, for example, in generating monoclonal antibodies or in screening DNA or cDNA libraries.

Stringent Hybridization Conditions. "Stringent hybridization conditions" is a term of art understood by those of ordinary skill in the art. For any given nucleic acid sequence, stringent hybridization conditions are those conditions of temperature and buffer solution which will permit hybridization of that nucleic acid sequence to its complementary sequence and not to substantially different sequences. The exact conditions which constitute "stringent" conditions, depend upon the length of the nucleic acid sequence and the frequency of occurrence of subsets of that sequence within other non-identical sequences. By varying hybridization conditions from a level of stringency at which no hybridization occurs to a level at which hybridization is first observed, one of ordinary skill in the art can, without undue experimentation, determine conditions which will allow a given sequence to hybridize only with identical sequences. Suitable ranges of such stringency conditions are described in Krause, M. H. and S. A. Aaronson, *Methods in Enzymology*, 200:546–556 (1991). Stringent hybridization conditions, depending upon the length and commonality of a sequence, may include hybridization conditions of 30° C.–65° C. and from 5X to 0.1X SSPC. Less than stringent hybridization conditions are employed to isolate nucleic acid sequences which are substantially similar, allelic or homologous to any given sequence.

When using primers that are derived from nucleic acid encoding a PTPL1 or GLM-2 PTP, one skilled in the art will recognize that by employing high stringency conditions (e.g. annealing at 50°–60° C.), sequences which are greater than about 75% homologous to the primer will be amplified. By employing lower stringency conditions (e.g. annealing at 35°–37° C.), sequences which are greater than about 40–50% homologous to the primer will be amplified.

When using DNA probes derived from a PTPL1 or GLM-2 PTP for colony/plague hybridization, one skilled in the art will recognize that by employing high stringency conditions (e.g. hybridization at 50°–65° C., 5X SSPC, 50% formamide, wash at 50°–65° C., 0.5X SSPC), sequences having regions which are greater than about 90% homologous to the probe can be obtained, and by employing lower stringency conditions (e.g. hybridization at 35°–37° C., 5X SSPC, 40–45% formamide, wash at 42° C. SSPC), sequences having regions which are greater than 35–45% homologous to the probe will be obtained.

Substantially similar. Two nucleic acid sequences are substantially similar if one of them or its anti-sense complement can bind to the other under strict hybridization conditions so as to distinguish that strand from all or substantially all other sequences in a cDNA or genomic library. Alternatively, one sequence is substantially similar to another if it or its anti-sense complement is useful as a probe in screening for the presence of its similar DNA or RNA sequence under strict hybridization conditions. Two proteins are substantially similar if they are encoded by substantially similar DNA or RNA sequences. In addition, even if they are not encoded by substantially similar nucleic acids, two proteins are substantially similar if they share sufficient primary, secondary and tertiary structure to perform the same biological role (structural or functional) with substantially the same efficacy or utility.

Variant. A "variant" of a protein or nucleic acid or fragment thereof is meant to include a molecule substantially similar in structure to the protein or nucleic acid, or to a fragment thereof. Variants of nucleic acid sequences include sequences with conservative nucleotide substitutions, small insertions or deletions, or additions. Variants of proteins include proteins with conservative amino acid substitutions, small insertions or deletions, or additions. Thus, nucleotide substitutions which do not effect the amino acid sequence of the subsequent translation product are particularly contemplated. Similarly, substitutions of structurally similar amino acids in proteins, such as leucine for isoleucine, or insertions, deletions, and terminal additions which do not destroy the functional utility of the protein are contemplated. Allelic variants of nucleic acid sequences and allelomorphic variants or protein or polypeptide sequences are particularly contemplated. As is well known in the art, an allelic variant is simply a naturally occurring variant of a polymorphic gene and that term is used herein as it is commonly used in the field of population genetics. The production of such variants is well known in the art and, therefore, such variants are intended to fall within the spirit and scope of the claims.

Homologous and homologues. As used herein, the term "homologues" is intended to embrace either and/or both homologous nucleic acid sequences and homologous protein sequences as the context may indicate. Homologues are a class of variants, as defined above, which share a sufficient degree of structural and functional similarity so as to indicate to one of ordinary skill in the art that they share a common evolutionary origin and that the structural and functional similarity is the result of evolutionary conservation. To be considered homologues of the PTPL1 or GLM-2 PTP, nucleic acid sequences and the proteins they encode must meet two criteria: (1) The polypeptides encoded by homologous nucleic acids are at least approximately 50–60% identical and preferably at least 70% identical for at least one stretch of at least 20 amino acids. As is well known in the art, both the identity and the approximate positions of the amino acid residues relative to each other must be conserved and not just the overall amino acid composition. Thus, one must be able to "line up" the conserved regions of the homologues and conclude that there is 50–60% identity; and (2) The polypeptides must retain a functional similarity to the PTPL1 or GLM-2 PTP in that it is a protein tyrosine phosphatase.

Substantially Pure. The term "substantially pure" when applied to the proteins, variants or fragments thereof of the present invention means that the proteins are essentially free of other substances to an extent practical and appropriate for their intended use. In particular, the proteins are sufficiently pure and are sufficiently free from other biological constituents of their hosts cells so as to be useful in, for example, protein sequencing, or producing pharmaceutical preparations. By techniques well known in the art, substantially pure proteins, variants or fragments thereof may be produced in light of the nucleic acids of the present invention.

Isolated. Isolated refers to a nucleic acid sequence which has been: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid sequence is one which is readily manipulable by recombinant DNA techniques well known in the art. Thus, a nucleic acid sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid sequence that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

Immunogenetically Effective Amount. An "immunogenetically effective amount" is that amount of an antigen (e.g. a protein, variant or a fragment thereof) necessary to induce the production of antibodies which will bind to the epitopes of the antigen. The actual quantity comprising an "immunogenetically effective amount" will vary depending upon factors such as the nature of the antigen, the organism to be immunized, and the mode of immunization. The determination of such a quantity is well within the ability of one ordinarily skilled in the art without undue experimentation.

Antigen and Antibody. The term "antigen" as used in this invention is meant to denote a substance that can induce a detectable immune response to it when introduced to an animal. Such substances include proteins and fragments thereof.

The term "epitope" is meant to refer to that portion of an antigen which can be recognized and bound by an antibody. An antigen may have one, or more than one epitope. An "antigen" is capable of inducing an animal to produce antibody capable of binding to an epitope of that antigen. An "immunogen" is an antigen introduced into an animal specifically for the purpose of generating an immune response to the antigen. An antibody is said to be "capable of selectively binding" a molecule if it is capable of specifically reacting with the molecule to thereby bind the molecule to the antibody. The selective binding of an antigen and antibody is meant to indicate that the antigen will react, in a highly specific manner, with its corresponding antibody and not with the multitude of other antibodies which may be evoked by other antigens.

The term "antibody" (Ab) or "monoclonal antibody" (Mab) as used herein is meant to include intact molecules as well as fragments thereof (such as, for example, Fab and F(ab')$_2$ fragments) which are capable of binding an antigen. Fab and F(ab')$_2$ fragments lack the Fc fragment of intact antibody, clear more rapidly from the circulation, and may have less non-specific tissue binding than an intact antibody. Single chain antibodies, humanized antibodies, and fragments thereof, also are included.

DESCRIPTION OF THE PREFERRED EMBODIMENTS

The present invention relates to the identification, isolation and cloning of two novel protein tyrosine phosphatases designated PTPL1 and GLM-2. Specifically, the present invention discloses the isolation and cloning of cDNA and the amino acid sequences of PTPL1 and GLM-2 from human glioblastoma and brain cell cDNA libraries. These phosphatases are, initially, discussed separately below. As they are related in function and utility as well as structurally with respect to their catalytic domains, they are subsequently discussed in the alternative.

In order to identify novel PTPs, a PCR-based approach was used. PCR was performed using cDNA from the human glioma cell line U-343 MGa 31L as a template and degenerate primers that were based on conserved regions of PTPs. One primer was derived from the catalytic site (HCSAG) of the PTP domain and two primers were derived from conserved regions in the N-terminal part of the domain. Several PCR-products were obtained, including some corresponding to the cytoplasmic PTPs PTPH1 (Yang, Q., and Tonks, N. K. (1991) *Proc. Natl. Acad. Sci.* (*USA*) 88:5949–5953), PTPase MEG (Gu, M., et al., (1991) *Proc. Natl. Acad. Sci.* (*USA*) 88:5867–5871), P19PTP (den Hertog, J., et al., (1992) *Biochem. Biophys. Res. Commun.* 184:1241–1249), and TC-PTP (Cool, D. E., et al., (1989) *Proc. Natl. Acad. Sci.* (*USA*) 86:5257–5261), as well as to the receptor-like PTPs HPTP-α, HPTP-γ, and HPTP-δ (Krueger, N. X., et al., (1990) *EMBO J.* 9:3241–3252). In addition to these known sequences, three PCR-products encoding novel PTP-like sequences were found.

One of these PCR-products is almost identical to a PCR-product derived from a human leukemic cell line (Honda, H., et al., (1993) *Leukemia* 7:742–746) and was chosen for further characterization and was used to screen an oligo-(dT)-primed U-343 MGa 31L cDNA library which resulted in the isolation of the clone λ6.15. Upon Northern blot analysis of mRNA from human foreskin fibroblasts AG1518, probed with the λ6.15 insert, a transcript of 9.5 kb could be seen. Therefore AG1518 cDNA libraries were constructed and screened with λ6.15 in order to obtain a full-length clone. Screening of these libraries with λ6.15, and thereafter with subsequently isolated clones, resulted in several overlapping clones which together covered 8040 bp including the whole coding sequence of a novel phosphatase, denoted PTPL1. The total length of the open reading frame was 7398 bp coding for 2466 amino acids with a predicted molecular mass of 275 kDa. The nucleotide and deduced amino acid sequence of PTPL1 are disclosed as SEQ ID NO.:1 and SEQ ID NO.:2, respectively. Although the sequence surrounding the putative initiator codon at positions 78–80 does not conform well to the Kozak consensus sequence (Kozak, M. (1987) *Nucl. Acids Res.* 15:8125–8148) there is a purine at position -3 which is an important requirement for an initiation site. The 77 bp 5' untranslated region is GC-rich and contains an inframe stop codon at positions 45–47. A 3' untranslated region of 565 bp begins after a TGA stop codon at positions 7476–7478, and does not contain a poly-A tail.

Figure 1:
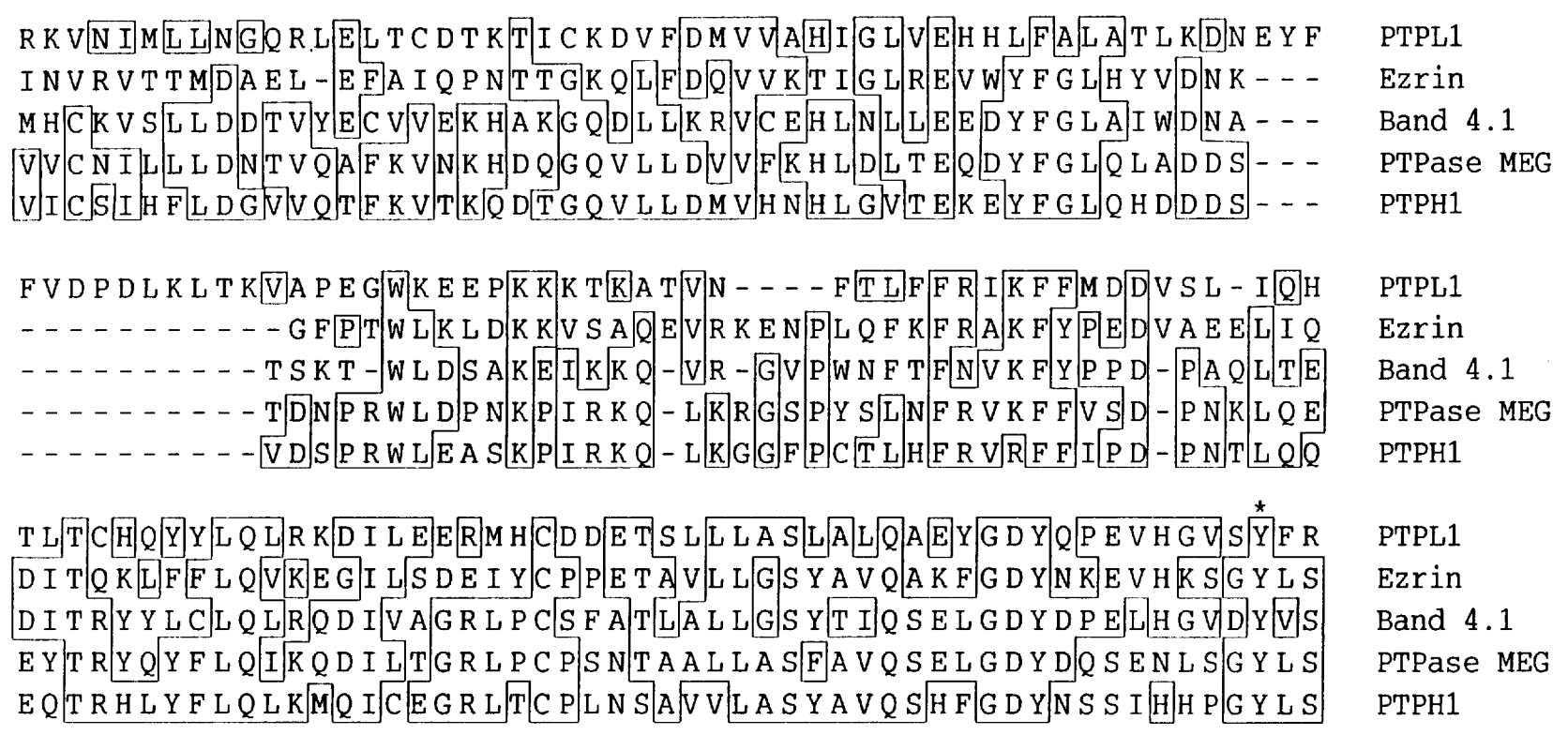

In the deduced amino acid sequence of PTPL1 no transmerubrane domain or signal sequence for secretion are found, indicating that PTPL1 is a cytoplasmic PTP. Starting from the N-terminus, the sequence of the first 470 amino acid residues shows no homology to known proteins. The region 470–505 contains a leucine zipper motif, with a methionine in the position where the fourth leucine usually is found (LX$_6$LX$_6$LX$_6$MX$_6$L); similar replacements of leucine residues with methionine residues are also found in the leucine zippers of the transcription factors CYS-3 (Fu, Y.-H., et al., (1989) *Mol. Cell. Biol.* 9:1120–1127) and dFRA (Perkins, K. K., et al., (1990) *Genes Dev.* 4:822–834). Furthermore, consistent with the notion that this is a functional leucine zipper, no helix breaking residues (glycine and proline) are present in this region. The leucine zipper motif is followed by a 300 amino acid region (570–885) with homology to the band 4.1 superfamily (see FIG. 1). The members of this superfamily are cytoskeleton-associated proteins with a homologous domain in the N-terminus (Tsukita, S., et al., (1992) *Curr. Opin. Cell* Biol. 4:834–839). Interestingly, two cytoplasmic PTPs, PTPH1 and PTPase MEG, contain a band 4.1-like domain. The band 4.1-like domain of PTPL1 is 20% to 24% similar to most known proteins of this superfamily, including ezrin (Gould, K. L., et al., (1989) *EMBO J.* 8:4133–4142), moesin (Lankes, W. T., and Furthmayr, H. (1991) *Proc. Natl. Acad. Sci.* (USA) 88:8297–8301), radixin (Funayama, N., et al., (1991) *J. Cell Biol.* 115:1039–1048), merlin (Trofatter, J. A., et al., (1993) *Cell* 72:791–800), band 4.1 protein (Conboy, J., et al., (1986) *Proc. Natl. Acad. Sci.* (USA) 83:9512–9516), PTPH1 (Yang, Q., and Tonks, N. K. (1991) *Proc. Natl. Acad. Sci.* (USA) 88:5949–5953) and PTPase MEG (Gu, M., et al., (1991) *Proc. Natl. Acad. Sci.* (USA) 88:5867–5871).

Between amino acid residues 1080 and 1940 there are five 80 amino acid repeats denoted GLGF-repeats. This repeat was first found in PSD-95 (Cho, K.-O., et al., (1992) *Neuron* 9:929–942), also called SAP (Kistner, U., et al., (1993) *J. Biol. Chem.* 268:4580–4583), a protein in post-synaptic densities, i.e. structures of the submembranous cytoskeleton in synaptic junctions. Rat PSD-95 is homologous to the discs-large tumor suppressor gene in Drosophila (Woods, D. F., and Bryant, P. J. (1991) *Cell* 66:451–464), dlg-A, which encodes a protein located in septate junctions. These two proteins each contain three GLGF-repeats, one SH-3 domain and a guanylate kinase domain. Through computer searches in protein data bases complemented by manual searches, 19 GLGF-repeats in 9 different proteins, all of them enzymes, were found (see FIG. 2 and FIG. 3). Besides dlg-A and PSD-95, there are two other members of the guanylate kinase family, a 220-kDa protein (Itoh, M., et al., (1993) *J. Cell Biol.* 121:491–502) which is a constitutive protein of the plasma membrane undercoat with three GLGF-repeats, and p55 (Ruff, P., et al., (1991) *Proc. Natl. Acad. Sci.* (USA) 88:6595–6599) which is a palmitoylated protein from erythrocyte membranes with one GLGF-repeat. A close look into the sequence of PTPH1 and PTPase MEG revealed that each of them has one GLGF-repeat between the band 4.1 homology domain and the PTP domain. One GLGF-repeat is also found in nitric oxide synthase from rat brain (Bredt, D. S., et al., (1991) *Nature* 351:714–718), and a glioma cell line, U-118MG, expresses an altered ros1 transcript (Sharma, S., et al., (1989) *Oncogene Res.* 5:91–100), containing a GLGF-repeat probably as a result of a gene fusion.

The PTP domain of TPL1 is localized in the C-terminus (amino acid residues 2195–2449). It contains most of the conserved motifs of PTP domains and shows about 30% similarity to known PTPs.

Use of a 9.5 kb probe including SEQ ID NO.:1 for Northern blot analysis for tissue-specific expression showed high expression of PTPL1 in human kidney, placenta, ovaries, and testes; medium expression in human lung, pancreas, prostrate and brain; low expression in human heart, skeletal muscle, spleen, liver, small intestine and colon; and virtually no detectable expression in human leukocytes. Furthermore, using a rat PCR product for PTPL1 as a probe, PTPL1 was found to be expressed in adult rats but not in rat embryos. This latter finding suggests that PTPL1 may have a role, like many PTPs, in the signal transduction process that leads to cellular growth or differentiation.

The rabbit antiserum αL1A (see Example 5), made against a synthetic peptide derived from amino acid residues 1802–1823 in the PTPL1 sequence, specifically precipitated a component of 250 kDa from [$^{35}$S]methionine and [$^{35}$S] cysteine labeled COS-1 cells transfected with the PTPL1 cDNA. This component could not be detected in untransfected cells, or in transfected cells using either pre-immune serum or antiserum pre-blocked with the immunogenic peptide. Identical results were obtained using the antiserum αL1B (see Example 5) made against residues 450–470 of PTPL1. A component of about 250 kDa could also be detected in immunoprecipitations using AG1518 cells, PC-3 cells, CCL-64 cells, A549 cells and PAE cells. This component was not seen upon precipitation with the preimmune serum, or when precipitation was made with αL1A antiserum preblocked with peptide. The slight variations in sizes observed between the different cell lines could be due to species differences. A smaller component of 78 kDa was also specifically precipitated by the αL1A antiserum. The relationship between this molecule and PTPL1 remains to be determined.

Figure 4:
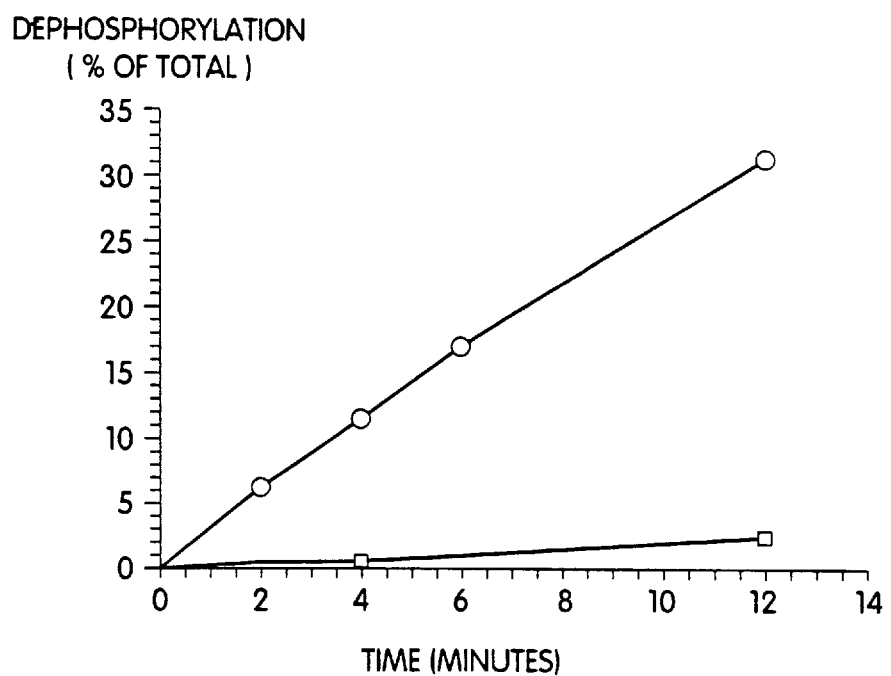
FIG. 4. PTP activity of PTPL1. Immunoprecipitates from COS-1 cells using an antiserum (αL1B) against PTPL1, unblocked (open circles) or blockeod with peptide (open sguares), were incubated for 2, 4, 6 or 12 minutes with myelin basic protein, $^{32}$P-labeled on tyrosine residues. The amount of radioactivity released as inorganic phosphate is expressed as the percentage of the total input of radioactivity.

In order to demonstrate that PTPL1 has PTP activity, immunoprecipitates from COS-1 cells transfected with PTPL1 cDNA were incubated with myelin basic protein, $^{32}$P-labeled on tyrosine residues, as a substrate. The amount of radioactivity released as inorganic phosphate was measured. Immunoprecipitates with αL1B (open circles) gave a time-dependent increase in dephosphorylation with over 30% dephosphorylation after 12 minutes compared to 2% dephosphorylation when the antiserum was pre-blocked with peptide (open squares) (see FIG. 4).

The present invention also provides an isolated nucleic acid sequence encoding a novel PTP designated GLM-2, variants and fragments thereof, and uses relating thereto. One sequence encoding a GLM-2 PTP and surrounding nucleotides is disclosed as SEQ ID NO.:3. This sequence includes the coding sequences for GLM-2 PTP as well as both 5' and 3' untranslated regions including regulatory sequences. The full disclosed sequence, designated SEQ ID NO.:3 is 3090 bp in length.

The nucleic acid sequence of SEQ ID NO.:3 includes 1310 base pairs of 5' untranslated region and 673 bp of 3' untranslated region which do not appear to encode a sequence for a poly-A (polyadenylation) tail. Transcription of SEQ ID NO.:3 begins at approximately position 1146. A translation start codon (ATG) is present at positions 1311 to 1313 of SEQ ID NO.:3. The nucleotides surrounding the start codon (AGCATGG) show substantial similarity to the Kozak consensus sequence (RCCATGG) (Kozak, M. (1987) *Nucl. Acids Res.* 15:8125–8148). A translation stop codon (TGA) is present at positions 2418 to 2420 of SEQ ID NO.:3. The open reading frame of 1107 bp encodes a protein of 369 amino acid residues with a predicted molecular mass of 41 kD. The deduced amino acid sequence of this protein is disclosed as SEQ ID NO.:4.

The sequence disclosed in SEQ ID NO.:3 encodes a single domain PTP similar to the rat PTP STEP (53% identity; Lombroso, et al., 1991) and the human PTP LC-PTP (51% identity; Adachi, M., et al., (1992) *FEBS Letters* 314:335–339). None of the sequenced regions encodes a polypeptide sequence with any substantial similarity to known signal or transmembrane domains. Further indicating that GLM-2 is a cytoplasmic PTP.

Use of a 3.6 kb probe including SEQ ID NO.:3 for Northern blot analysis for tissue-specific expression showed a strong association with human brain tissue and little or no expression in human heart, placenta, lung, liver, skeletal muscle, kidney or pancreas. This is similar to to the pattern of tissue-specific expression shown by STEP.

Cloning and expression of PTPL1 and GLM-2.

In one series of embodiments of the present invention, an isolated DNA, cDNA or RNA sequence encoding a PTPL1 or GLM-2 PTP, or a variant or fragment thereof, is provided. The procedures described above, which were employed to isolate the first PTPL1 and GLM-2 sequences no longer need be employed. Rather, using the sequences disclosed herein, a genomic DNA or cDNA library may be readily screened to isolate a clone containing at least a fragment of a PTPL1 or GLM-2 sequence and, if desired, a full sequence. Alternatively one may synthesize PTPL1 and GLM-2 encoding nucleic acids using the sequences disclosed herein.

The present invention further provides vectors containing nucleic acid sequences encoding PTPL1 and GLM-2. Such vectors include, but are not limited to, plasmids, phage, plasmids and cosmid vectors. In light of the present disclosure, one of ordinary skill in the art can readily place the nucleic acid sequences of the present invention into any of a great number of known suitable vectors using routine procedures.

The source nucleic acids for a DNA library may be genomic DNA or cDNA. Which of these is employed depends upon the nature of the sequences sought to be cloned and the intended use of those sequences.

Genomic DNA may be obtained by methods well known to those or ordinary skill in the art (for example, see *Guide to Molecular Cloning Techniques*, S. L. Berger et al., eds., Academic Press (1987)). Genomic DNA is preferred when it is desired to clone the entire gene including its endogenous regulatory sequences. Similarly, genomic DNA is used when it is only the regulatory sequences which are of interest.

Complementary or cDNA may be produced by reverse transcription methods which are well known to those of ordinary skill in the art (for example, see *Guide to Molecular Cloning Techniques*, S. L. Berger et al., eds., Academic Press (1987)). Preferably, the mRNA preparation for reverse transcription should be enriched in the DNA of the desired sequence. This may be accomplished by selecting cells in which the mRNA is produced at high levels or by inducing high levels of production. Alternatively, in vitro techniques may be used such as sucrose gradient centrifugation to isolate mRNA transcripts of a particular size. cDNA is preferred when the regulatory sequences of a gene are not needed or when the genome is very large in comparison with the expressed transcripts. In particular, cDNA is preferred when a eukaryotic gene containing introns is to be expressed in a prokaryotic host.

To create a DNA or cDNA library, suitable DNA or cDNA preparations are randomly sheared or enzymatically cleaved by restriction endonucleases to create fragments appropriate in size for the chosen library vector. The DNA or cDNA fragments may be inserted into the vector in accordance with conventional techniques, including blunt-ending or staggered-ending termini for ligation. Typically, this is accomplished by restriction enzyme digestion to provide appropriate termini, the filling-in of cohesive ends as appropriate, alkaline phosphatase treatment to avoid undesirable joining, and ligation with appropriate ligases. Techniques for such manipulations are well known in the art and may be found, for example, in Sambrook, et al., *Molecular Cloning, A Laboratory Manual*, 2d ed., Cold Spring Harbor Laboratory Press, Plainview, N.Y. (1989). The library will consist of a great many clones, each containing a fragment of the total DNA or cDNA. A great variety of cloning vectors, restriction endonucleases and ligases are commercially available and their use in creating DNA libraries is well known to those of ordinary skill in the art. See, for example, Sambrook, et al., *Molecular Cloning, A Laboratory Manual*, 2d ed., Cold Spring Harbor Laboratory Press, Plainview, N.Y. (1989).

DNA or cDNA libraries containing sequences coding for PTPL1 or GLM-2 nucleic acid sequences may be screened and a sequence coding for either PTPL1 or GLM-2 identified by any means which specifically selects for that sequence. Such means include (a) hybridization with an appropriate nucleic acid probe(s) containing a unique or substantially characteristic fragment of the desired DNA or cDNA (b) hybridization-selected translational analysis in which native mRNA which hybridizes to the clone in question is translated in vitro and the translation products are further characterized (c) if the cloned genetic sequences are themselves capable of expressing mRNA, immunoprecipitation of a translated PTPL1 or GLM-2 recombinant product produced by the host containing the clone, or preferably (d) by using a unique or substantially characteristic fragment of the desired sequence as a PCR primer to amplify those clones with which it hybridizes.

Preferably, the probe or primer is a substantially characteristic fragment of one of the disclosed sequences. More preferably, the probe is a unique fragment of one of the disclosed sequences. In choosing a fragment, unique and substantially characteristic fragments can be identified by comparing the sequence of a proposed probe to the known sequences found in sequence databases. Alternatively, the entire PTPL1 or GLM-2 sequence may be used as a probe. In a preferred embodiment, the probe is a $^{32}$P random-labeled unique fragment of the PTPL1 or GLM-2 nucleic acid sequences disclosed herein. In a most preferred embodiment, the probe serves as a PCR primer containing a unique or substantially characteristic fragment of the PTPL1 or GLM-2 sequences disclosed herein.

The library to be screened may be DNA or cDNA. Preferably, a cDNA library is screened. In a preferred embodiment, a U-343 MGa 31L human glioblastoma (Nister, M., et al., (1988) *Cancer Res.* 48:3910–3918) or AG1518 human fibroblast (Human Genetic Mutant Cell Repository, Institute for Medical Research, Camden, N.J.) cDNA library is screened with a probe to a unique or substantially characteristic fragment of the PTPL1 sequence. Because PTPL1 is expressed in a wide variety of tissues, cDNA libraries from many tissues may be employedN n another preferred embodiment, a λgt10 human brain cDNA library (Clontech, Calif.) is screened with a probe to a unique or substantially characteristic fragment of the GLM-2 sequence. Because expression of GLM-2 appears to be high in brain tissues but low or absent in other tissues tested, a brain cDNA library is recommended for the cloning of GLM-2.

The selected fragments may be cloned into any of a great number of vectors known to those of ordinary skill in the art. In one preferred embodiment, the cloning vector is a plasmid such as pUC18 or Bluescript (Stratagene). The cloned sequences should be examined to determine whether or not they contain the entire PTPL1 or GLM-2 sequences or desired portions thereof. A series of overlapping clones of partial sequences may be selected and combined to produce a complete sequence by methods well known in the art.

In an alternative embodiment of cloning a PTPL1 or GLM-2 nucleotide sequence, a library is prepared using an expression vector. The library is then screened for clones which express the PTPL1 or GLM-2 protein, for example, by screening the library with antibodies to the protein or with labeled probes for the desired RNA sequences or by assaying for PTPL1 or GLM-2 PTP activity on a phosphorylated substrate such as para-nitrylphenyl phosphate. The above discussed methods are, therefore, capable of identifying cloned genetic sequences which are capable of expressing PTPL1 or GLM-2 PTPs, or variants or fragments thereof.

To express a PTPL1 or GLM-2 PTP, variants or fragments thereof, or PTPL1 or GLM-2 anti-sense RNA, and variants or fragments thereof, transcriptional and translational signals recognizable by an appropriate host are necessary. The cloned PTPL1 or GLM-2 encoding sequences, obtained through the methods described above, and preferably in a double-stranded form, may be operably joined to regulatory sequences in an expression vector, and introduced into a host cell, either prokaryote or eukaryote, to produce recombinant PTPL1 or GLM-2 PTP, a variant or fragment thereof, PTPL1 or GLM-2 anti-sense RNA, or a variant or fragment thereof.

Depending upon the purpose for which expression is desired, the host may be eukaryotic or prokaryotic. For example, if the intention is to study the regulation of PTPL1 or GLM-2 PTP in a search for inducers or inhibitors of its activity, the host is preferably eukaryotic. In one preferred embodiment, the eukaryotic host cells are COS cells derived from monkey kidney. In a particularly preferred embodiment, the host cells are human fibroblasts. Many other eukaryotic host cells may be employed as is well known in the art. For example, it is known in the art that *Xenopus* oocytes comprise a cell system useful for the functional expression of eukaryotic messenger RNA or DNA. This system has, for example, been used to clone the sodium:glucose cotransporter in rabbits (Hediger, M. A., et. al., *Proc. Natl. Acad. Sci.* (*USA*) 84:2634–2637 (1987)). Alternatively, if the intention is to produce large quantities of the PTPL1 or GLM-2 PTPs, a prokaryotic expression system is preferred. The choice of an appropriate expression system is within the ability and discretion of one of ordinary skill in the art.

Depending upon which strand of the PTPL1 or GLM-2 PTP encoding sequence is operably joined to the regulatory sequences, the expression vectors will produce either PTPL1 or GLM-2 PTPs, variants or fragments thereof, or will express PTPL1 and GLM-2 anti-sense RNA, variants or fragments thereof. Such PTPL1 and GLM-2 anti-sense RNA may be used to inhibit expression of the PTPL1 or GLM-2 PTP and/or the replication of those sequences.

Expression of a protein in different hosts may result in different post-translational modifications which may alter the properties of the protein. This is particularly true when eukaryotic genes are expressed in prokaryotic hosts. In the present invention, however, this is of less concern as PTPL1 and GLM-2 are cytoplasmic PTPs and are unlikely to be post-translationally glycosylated.

Transcriptional initiation regulatory sequences can be selected which allow for repression or activation, so that expression of the operably joined sequences can be modulated. Such regulatory sequences include regulatory sequences which are temperature-sensitive so that by varying the temperature, expression can be repressed or initiated, or which are subject to chemical regulation by inhibitors or inducers. Also of interest are constructs wherein both PTPL1 or GLM-2 mRNA and PTPL1 or GLM-2 anti-sense RNA are provided in a transcribable form but with different promoters or other transcriptional regulatory elements such that induction of PTPL1 or GLM-2 mRNA expression is accompanied by repression of the expression of the corresponding anti-sense RNA, or alternatively, repression of PTPL1 or GLM-2 mRNA expression is accompanied by induction of expression of the corresponding anti-sense RNA. Translational sequences are not necessary when it is desired to express PTPL1 and GLM-2 anti-sense RNA sequences.

A non-transcribed and/or non-translated sequence 5' or 3' to the sequence coding for PTPL1 or GLM-2 PTP can be obtained by the above-described cloning methods using one of the probes disclosed herein to select a clone from a genomic DNA library. A 5' region may be used for the endogenous regulatory sequences of the PTPL1 or GLM-2 PTP. A 3'-non-transcribed region may be utilized for a transcriptional termination regulatory sequence or for a translational termination regulatory sequence. Where the native regulatory sequences do not function satisfactorily in the host cell, then exogenous sequences functional in the host cell may be utilized.

The vectors of the invention further comprise other operably joined regulatory elements such as DNA elements which confer tissue or cell-type specific expression of an operably joined coding sequence.

Oligonucleotide probes derived from the nucleotide sequence of PTPL1 or GLM-2 can be used to identify genomic or cDNA library clones possessing a related nucleic acid sequence such as an allelic variant or homologous sequence. A suitable oligonucleotide or set of oligonucleotides, which is capable of encoding a fragment of the PTPL1 or GLM-2 coding sequences, or a PTPL1 or GLM-2 anti-sense complement of such an oligonucleotide or set of oligonucleotides, may be synthesized by means well known in the art (see, for example, *Synthesis and Application of DNA and RNA*, S. A. Narang, ed., 1987, Academic Press, San Diego, Calif.) and employed as a probe to identify and isolate a cloned PTPL1 or GLM-2 sequence, variant or fragment thereof by techniques known in the art. As noted above, a unique or substantially characteristic fragment of a PTPL1 or GLM-2 sequence disclosed herein is preferred. Techniques of nucleic acid hybridization and clone identification are disclosed by Sambrook, et al., *Molecular Cloning, A Laboratory Manual*, 2d ed., Cold Spring Harbor Laboratory Press, Plainview, N.Y. (1989), and by Hames, B.D., et al., in *Nucleic Acid Hybridization, A Practical Approach*, IRL Press, Washington, D.C. (1985). To facilitate the detection of a desired PTPL1 or GLM-2 nucleic acid sequence, whether for cloning purposes or for the mere detection of the presence of PTPL1 or GLM-2 sequences, the above-described probes may be labeled with a detectable group. Such a detectable group may be any material having a detectable physical or chemical property. Such materials have been well-developed in the field of nucleic acid hybridization and in general most any label useful in such methods can be applied to the present invention. Particularly useful are radioactive labels. Any radioactive label may be employed which provides for an adequate signal and has a sufficient half-life. If single stranded, the oligonucleotide may be radioactively labeled using kinase reactions. Alternatively, oligonucleotides are also useful as nucleic acid hybridization probes when labeled with a non-radioactive marker such as biotin, an enzyme or a fluorescent group. See, for example, Leary, J. J., et al., *Proc. Natl. Acad. Sci.*(*USA*) 80:4045 (1983); Renz, M. et al., *Nucl. Acids Res.* 12:3435 (1984); and Renz, M., *EMBO J.* 6:817 (1983).

By using the sequences disclosed herein as probes or as primers, and techniques such as PCR cloning and colony/plaque hybridization, it is within the abilities of one skilled in the art to obtain human allelic variants and sequences substantially similar or homologous to PTPL1 or GLM-2 nucleic acid sequences from species including mouse, rat, rabbit and non-human primates. Thus, the present invention is further directed to mouse, rat, rabbit and primate PTPL1 and GLM-2.

In particular the protein sequences disclosed herein for PTPL1 and GLM-2 may be used to generate sets of degenerate probes or PCR primers useful in isolating similar and potentially evolutionarily similar sequences encoding proteins related to the PTPL1 or GLM-2 PTPs. Such degenerate probes may not be substantially similar to any fragments of the PTPL1 or GLM-2 nucleic acid sequences but, as derived from the protein sequences disclosed herein, are intended to fall within the spirit and scope of the claims.

Antibodies to PTPL1 and GLM-2.

In the following description, reference will be made to various methodologies well-known to those skilled in the art of immunology. Standard reference works setting forth the general principles of immunology include Catty, D. *Antibodies, A Practical Approach*, Vols. I and II, IRL Press, Washington, D.C. (1988); Klein, J. *Immunology: The Science of Cell-Noncell Discrimination*, John Wiley & Sons, New York (1982); Kennett, R., et al. in *Monoclonal Antibodies, Hybridoma: A New Dimension in Biological Analyses*, Plenum Press, New York (1980); Campbell, A., "Monoclonal Antibody Technology," in *Laboratory Techniques in Biochemistry and Molecular Biology*, Volume 13 (Burdon, R., et al., eds.), Elsevier, Amsterdam (1984); and Eisen, H. N., in *Microbiology*, 3rd Ed. (Davis, B. D., et al., eds.) Harper & Row, Philadelphia (1980).

The antibodies of the present invention are prepared by any of a variety of methods. In one embodiment, purified PTPL1 or GLM-2 PTP, a variant or a fragment thereof, is administered to an animal in order to induce the production of sera containing polyclonal antibodies that are capable of binding the PTP, variant or fragment thereof.

The preparation of antisera in animals is a well known technique (see, for example, Chard, *Laboratory Techniques in Biology*, "An Introduction to Radioimmunoassay and Related Techniques," North Holland Publishing Company (1978), pp. 385–396; and *Antibodies, A Practical Handbook*, Vols. I and II, D. Catty, ed., IRL Press, Washington, D.C. (1988)). The choice of animal is usually determined by a balance between the facilities available and the likely requirements in terms of volume of the resultant antiserum. A large species such as goat, donkey and horse may be preferred, because of the larger volumes of serum readily obtained. However, it is also possible to use smaller species such as rabbit or guinea pig which often yield higher titer antisera. Usually, a subcutaneous injection of the antigenic material (the protein or fragment thereof or a hapten-carrier protein conjugate) is used. The detection of appropriate antibodies may be carried out by testing the antisera with appropriately labeled tracer-containing molecules. Fractions that bind tracer-containing molecules are then isolated and further purified if necessary.

Cells expressing PTPL1 or GLM-2 PTP, a variant or a fragment thereof, or, a mixture of such proteins, variants or fragments, can be administered to an animal in order to induce the production of sera containing polyclonal antibodies, some of which will be capable of binding the PTPL1 or GLM-2 PTP. If desired, such PTPL1 or GLM-2 antibody may be purified from other polyclonal antibodies by standard protein purification techniques and especially by affinity chromatography with purified PTPL1 or GLM-2 protein or variants or fragments thereof.

A PTPL1 or GLM-2 protein fragment may also be chemically synthesized and purified by HPLC to render it substantially pure. Such a preparation is then introduced into an animal in order to produce polyclonal antisera of high specific activity. In a preferred embodiment, the protein may be coupled to a carrier protein such as bovine serum albumin or keyhole limpet hemocyanin (KLH), and and used to immunogenize a rabbit utilizing techniques well-known and commonly used in the art. Additionally, the PTPL1 or GLM-2 protein can be admixed with an immunologically inert or active carrier. Carriers which promote or induce immune responses, such as Freund's complete adjuvant, can be utilized.

Monoclonal antibodies can be prepared using hybridoma technology (Kohler et al., *Nature* 256:495 (1975); Kohler, et al., *Eur. J. Immunol.* 6:511 (1976); Kohier, et al., *Eur. J. Immunol.* 6:292 (1976); Hammerling, et al., in *Monoclonal Antibodies and T-Cell Hybridomas*, Elsevier, N.Y., pp. 563–681 (1981)). In general, such procedures involve immunizing an animal with PTPL1 or GLM-2 PTP, or a variant or a fragment thereof. The splenocytes of such animals are extracted and fused with a suitable myeloma cell line. After fusion, the resulting hybridoma cells are selectively maintained in HAT medium, and then cloned by limiting dilution as described by Wands, J. R., et al., *Gastro-enterology* 80:225–232 (1981), which reference is herein incorporated by reference. The hybridoma cells obtained through such a selection are then assayed to identify clones which secrete antibodies capable of binding the PTP and/or the PTP antigen. The proliferation of transfected cell lines is potentially more promising than classical myeloma technology, using methods available in the art.

Through application of the above-described methods, additional cell lines capable of producing antibodies which recognize epitopes of the PTPL1 and GLM-2 PTPs can be obtained.

These antibodies can be used clinically as markers (both quantitative and qualitative) of the PTPL1 and GLM-2 PTPs in brain, blastoma or other tissue. Additionally, the antibodies are useful in a method to assess PTP function in cancer or other patients.

The method whereby two antibodies to PTPL1 were produced is outlined in Example 5.

Substantially pure PTPL1 and GLM-2 proteins.

A variety of methodologies known in the art can be utilized to obtain a purified PTPL1 or GLM-2 PTP. In one method, the protein is purified from tissues or cells which naturally produce the protein. Alternatively, an expression vector may be introduced into cells to cause production of the protein. For example, human fibroblast or monkey kidney COS cells may be employed. In another embodiment, mRNA transcripts may be microinjected into cells, such as *Xenopus* oocytes or rabbit reticulocytes. In another embodiment, mRNA is used with an in vitro translation system. In preferred embodiment, bacterial cells are used to make large quantities of the protein. In a particularly preferred embodiment, a fusion protein, such as a bacterial GST fusion (Pharmacia) may be employed, the fusion product purified by affinity chromatography, and the PTPL1 or GLM-2 protein may be released from the hybrid by cleaving the amino acid sequence joining them.

In light of the present disclosure, one skilled in the art can readily follow known methods for isolating proteins in order to obtain substantially pure PTPL1 or GLM-2 PTP, free of natural contaminants. These include, but are not limited to, immunochromatography, HPLC, size-exclusion chromatography, ion-exchange chromatography, and immuno-affinity chromatography.

Determinations of purity may be performed by physical characterizations (such as molecular mass in size fractionation), immunological techniques or enzymatic assays.

PTPL1 or GLM-2 PTP, variants or fragments thereof, purified in the above manner, or in a manner wherein equivalents of the above sequence of steps are utilized, are useful in the preparation of polyclonal and monoclonal antibodies, for pharmaceutical preparations to inhibit or enhance PTP activity and for in vitro dephosphorylations.
Variants of PTPL1 and GLM-2 nucleic acids and proteins.

Variants of PTPL1 or GLM-2 having an altered nucleic acid sequence can be prepared by mutagenesis of the DNA. This can be accomplished using one of the mutagenesis procedures known in the art.

Preparation of variants of PTPL1 or GLM-2 are preferably achieved by site-directed mutagenesis. Site-directed mutagenesis allows the production of variants of these PTPs through the use of a specific oligonucleotide which contains the desired mutated DNA sequence.

Site-directed mutagenesis typically employs a phage vector that exists in both a single-stranded and double-stranded form. Typical vectors useful in site-directed mutagenesis include vectors such as the M13 phage, as disclosed by Messing, et al., Third Cleveland Symposium on Macromolecules and *Recombinant DNA*, A. Walton, ed., Elsevier, Amsterdam (1981), the disclosure of which is incorporated herein by reference. These phage are commercially available and their use is generally well known to those skilled in the art. Alternatively, plasmid vectors containing a single-stranded phage origin of replication (Veira, et al., *Meth. Enzymol.* 153:3 (1987)) may be employed to obtain single-stranded DNA.

In general, site-directed mutagenesis in accordance herewith is performed by first obtaining a single-stranded vector that includes within its sequence the DNA sequence which is to be altered. An oligonucleotide primer bearing the desired mutated sequence is prepared, generally synthetically, for example by the method of Crea, et al., *Proc. Natl. Acad. Sci.* (*USA*) 75:5765 (1978). The primer is then annealed with the single-stranded vector containing the sequence which is to be altered, and the created vector is incubated with a DNA-polymerizing enzyme such as *E. coli* polymerase I Klenow fragment in an appropriate reaction buffer. The polymerase will complete the synthesis of a mutation-bearing strand. Thus, the second strand will contain the desired mutation. This heteroduplex vector is then used to transform appropriate cells and clones are selected that contain recombinant vectors bearing the mutated sequence.

While the site for introducing a sequence variation is predetermined, the mutation per se need not be predetermined. For example, to optimize the performance of a mutation at a given site, random mutagenesis may be conducted at a target region and the newly generated sequences can be screened for the optimal combination of desired activity. One skilled in the art can evaluate the functionality of the variant by routine screening assays.

The present invention further comprises fusion products of the PTPL1 or GLM-2 PTPs. As is widely known, translation of eukaryotic mRNA is initiated at the codon which encodes the first methionine. The presence of such codons between a eukaryotic promoter and a PTPL1 or GLM-2 sequence results either in the formation of a fusion protein (if the ATG codon is in the same reading frame as the PTP encoding DNA sequence) or a frame-shift mutation (if the ATG codon is not in the same reading frame as the PTP encoding sequence). Fusion proteins may be constructed with enhanced immunospecificity for the detection of these PTPs. The sequence coding for the PTPL1 or GLM-2 PTP may also be joined to a signal sequence which will allow secretion of the protein from, or the compartmentalization of the protein in, a particular host. Such signal sequences may be designed with or without specific protease sites such that the signal peptide sequence is amenable to subsequent removal.

The invention further provides detectably labeled, immobilized and toxin conjugated forms of PTPL1 and GLM-2 PTPs, and variants or fragments thereof. The production of such labeled, immobilized or toxin conjugated forms of a protein are well known to those of ordinary skill in the art. While radiolabeling represents one embodiment, the PTPs or variants or fragments thereof may also be labeled using fluorescent labels, enzyme labels, free radical labels, avidin-biotin labels, or bacteriophage labels, using techniques known to the art (Chard, *Laboratory Techniques in Biology*, "An Introduction to Radioimmunoassay and Related Techniques," North Holland Publishing Company (1978)).

Typical fluorescent labels include fluorescein isothiocyanate, rhodamine, phycoerythrin, phycocyanin, allophycocyanin, and fluorescamine.

Typical chemiluminescent compounds include luminol, isoluminol, aromatic acridinium esters, imidazoles, and the oxalate esters.

Typical bioluminescent compounds include luciferin, and luciferase. Typical enzymes include alkaline phosphatase, β-galactosidase, glucose-6-phosphate dehydrogenase, maleate dehydrogenase, glucose oxidase, and peroxidase.
Transformed cells, cell lines and hosts.

To transform a mammalian cell with the nucleic acid sequences of the invention many vector systems are available depending upon whether it is desired to insert the recombinant DNA construct into the host cell's chromosomal DNA, or to allow it to exist in an extrachromosomal form. If the PTPL1 or GLM-2 PTP coding sequence, along with an operably joined regulatory sequence is introduced into a recipient eukaryotic cell as a non-replicating DNA (or RNA) molecule, the expression of PTPL1 or GLM-2 PTP may occur through the transient expression of the introduced sequence. Such a non-replicating DNA (or RNA) molecule may be a linear molecule or, more preferably, a closed covalent circular molecule which is incapable of autonomous replication.

In a preferred embodiment, genetically stable transformants may be constructed with vector systems, or transformation systems, whereby recombinant PTPL1 or GLM-2 PTP DNA is integrated into the host chromosome. Such integration may occur de novo within the cell or, in a most preferred embodiment, be assisted by transformation with a vector which functionally inserts itself into the host chromosome with, for example, retro vectors, transposons or other DNA elements which promote integration of DNA sequences in chromosomes. A vector is employed which is capable of integrating the desired sequences into a mammalian host cell chromosome. In a preferred embodiment, the transformed cells are human fibroblasts. In another preferred embodiment, the transformed cells are monkey kidney COS cells.

Cells which have stably integrated the introduced DNA into their chromosomes may be selected by also introducing one or more markers which allow for selection of host cells which contain the expression vector in the chromosome, for example the marker may provide biocide resistance, e.g., resistance to antibiotics, or heavy metals, such as copper, or the like. The selectable marker can either be directly linked to the DNA sequences to be expressed, or introduced into the same cell by co-transfection.

In another embodiment, the introduced sequence is incorporated into a vector capable of autonomous replication in the recipient host. Any of a wide variety of vectors may be employed for this purpose, as outlined below.

Factors of importance in selecting a particular plasmid or vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Preferred eukaryotic plasmids include those derived from the bovine papilloma virus, SV40, and, in yeast, plasmids containing the 2-micron circle, etc., or their derivatives. Such plasmids are well known in the art (Botstein, D., et al., *Miami Wntr. Symp.* 19:265–274 (1982); Broach, J. R., in *The Molecular Biology of the Yeast Saccharomyces: Life Cycle and Inheritance*, Cold Spring Harbor Laboratory, Cold Spring Harbor, N.Y., p. 445–470 (1981); Broach, J. R., *Cell* 28:203–204 (1982); Bolion, D. P., et al., *J. Clin. Hematol. Oncol.* 10:39–48 (1980); Maniatis, T., in *Cell Biology: A Comprehensive Treatise, Vol. 3, Gene Expression*, Academic Press, NY, pp. 563–608 (1980)), and are commercially available. For example, mammalian expression vector systems which utilize the MSV-LTR promoter to drive expression of the cloned gene and with which it is possible to co-transfect with a helper virus to amplify plasmid copy number and to integrate the plasmid into the chromosomes of host cells have been described (Perkins, A. S., et al., *Mol. Cell Biol.* 3:1123 (1983); Clontech, Palo Alto, Calif.).

Once the vector or DNA sequence is prepared for expression, it is introduced into an appropriate host cell by any of a variety of suitable means, including transfection. After the introduction of the vector, recipient cells may be grown in a selective medium, which selects for the growth of vector-containing cells. Expression of the cloned nucleic acid sequence(s) results in the production of PTPL1 or GLM-2 PTP, or the production of a variant or fragment of the PTP, or the expression of a PTPL1 or GLM-2 anti-sense RNA, or a variant or fragment thereof. This expression can take place in a transient manner, in a continuous manner, or in a controlled manner as, for example, expression which follows induction of differentiation of the transformed cells (for example, by administration of bromodeoxyuracil to neuroblastoma cells or the like).

In another embodiment of the invention the host is a human host. Thus, a vector may be employed which will introduce into a human with deficient PTPL1 or GLM-2 PTP activity, operable PTPL1 or GLM-2 sequences which can supplement the patient's endogenous production. In another embodiment, the patient suffers from a cancer caused by an oncogene which is a protein tyrosine kinase (PTK). A vector capable of expressing the PTPL1 or GLM-2 protein is introduced within the patient to counteract the PTK activity.

The recombinant PTPL1 or GLM-2 PTP cDNA coding sequences, obtained through the methods above, may be used to obtain PTPL1 or GLM-2 anti-sense RNA sequences. An expression vector may be constructed which contains a DNA sequence operably joined to regulatory sequences such that the DNA sequence expresses the PTPL1 or GLM-2 anti-sense RNA sequence. Transformation with this vector results in a host capable of expression of a PTPL1 or GLM-2 anti-sense RNA in the transformed cell. Preferably such expression occurs in a regulated manner wherein it may be induced and/or repressed as desired. Most preferably, when expressed, anti-sense PTPL1 or GLM-2 RNA interacts with an endogenous PTPL1 or GLM-2 DNA or RNA in a manner which inhibits or represses transcription and/or translation of the PTPL1 or GLM-2 PTP DNA sequences and/or mRNA transcripts in a highly specific manner. Use of anti-sense RNA probes to block gene expression is discussed in Lichtenstein, C., *Nature* 333:801–802 (1988).

Assays for agonists and antagonists.

The cloning of PTPL1 and GLM-2 now makes possible the production and use of high through-put assays for the identification and evaluation of new agonists (inducers/ enhancers) and antagonists (repressors/inhibitors) of PTPL1 or GLM-2 PTPs for therapeutic strategies using single or combinations of drugs. The assay may, for example, test for PTPL1 or GLM-2 PTP activity in transfected cells (e.g. fibroblasts) to identify drugs that interfere with, enhance, or otherwise alter the expression or regulation of these PTPs. In addition, probes developed for the disclosed PTPL1 and GLM-2 nucleic acid sequences or proteins (e.g. DNA or RNA probes or or primers or antibodies to the proteins) may be used as qualitative and/or quantitative indicators for the PTPs in cell lysates, whole cells or whole tissue.

In a preferred embodiment, human fibroblast cells are transformed with the PTPL1 or GLM-2 PTP sequences and vectors disclosed herein. The cells may then be treated with a variety of compounds to identify those which enhance or inhibit PTPL1 or GLM-2 transcription, translation, or PTP activity. In addition, assays for PDGF (platelet derived growth factor) signalling, cell growth, chemotaxis, and actin reorganization are preferred to assess a compounds affect on PTPL1 or GLM-2 PTP transcription, translation or activity.

In another embodiment, the ability of a compound to enhance or inhibit PTPL1 or GLM-2 PTP activity is assayed in vitro. Using the substantially pure PTPL1 or GLM-2 PTPs disclosed herein, and a detectable phosphorylated substrate, the ability of various compounds to enhance or inhibit the phosphatase activity of PTPL1 or GLM-2 may be assayed. In a particularly preferred embodiment the phosphorylated substrate is para-nitryiphenyl phosphate (which turns yellow upon dephosphorylation).

In another embodiment, the ability of a compound to enhance or inhibit PTPL1 or GLM-2 transcription is assayed, Using the PTPL1 or GLM-2 cDNA sequences disclosed herein, one of ordinary skill in the art can clone the 5' regulatory sequences of the PTPL1 or GLM-2 genes. These regulatory sequences may then be operably joined to a sequence encoding a marker. The marker may be an enzyme with an easily assayable activity or may cause the host cells to change phenotypically or in their sensitivity or resistance to certain molecules. A wide variety of markers are known to those of ordinary skill in the art and appropriate markers may be chosen depending upon the host used. Compounds which may alter the transcription of PTPL1 or GLM-2 PTP may be tested by exposing cells transformed with the PTPL1 or GLM-2 regulatory sequences operably joined to the marker and assaying for increased or decreased expression of the marker.

The following examples further describe the particular materials and methods used in developing and carrying out some of the embodiments of the present invention. These examples are merely illustrative of techniques employed to date and are not intended to limit the scope of the invention in any manner.

EXAMPLE 1

Original Cloning of PTPL1

All cells, unless stated otherwise, were cultured in Dulbeco Modified Eagles Medium (DMEM Gibco) supplemented with 10% Fetal Calf Serum (FCS, Flow Laboratories), 100 units of penicillin, 50 $\mu$g/ml streptomycin and glutamine. The human glioma cell line used was U-343 MGa 31L (Nister, M., et al , (1988) *Cancer Res.* 48:3910–3918). The AG1518 human foreskin fibroblasts were from the Human Genetic Mutant Cell Repository, Institute for Medical Research, Camden, N.J.

RNA was prepared from U-343 MGa 31L cells or AG1518 human fibroblasts by guanidine thiocyanate (Merck, Darmstadt) extraction (Chirgwin et al., 1979). Briefly, cells were harvested, washed in phosphate buffered saline (PBS), and lysed in 4M guanidine thiocyanate containing 25 mM sodium citrate (pH 7.0) and 0.1M 2-mercaptoethanol. RNA was sedimented through 5.7M cesium chloride, the RNA pellet was then dissolved in 10 mM Tris hydrochloride (pH 7.5), 5 mM EDTA (TE buffer), extracted with phenol and chloroform, precipitated with ethanol, and the final pellet stored at −70° C. or resuspended in TE buffer for subsequent manipulations. Polyadenylated [poly(A)+] RNA was prepared by chromatography on oligo (dT)-cellulose as described in Maniatis et al., 1982.

Poly(A)+ RNA (5 μg) from U-343 MGa 31 L cells was used to make a cDNA library by oligo (dT)-primed cDNA synthesis using an Amersham λgt10 cDNA cloning system. Similarly, a random and oligo (dT) primed cDNA library was prepared from AG1518 fibroblasts using 5 μg of poly (A)+ RNA, a RiboClone cDNA synthesis system (Promega Corporation, Madison, Wis., USA), a Lambda ZAPII synthesis kit (Stratagene), and Gigapack Gold II packaging extract (Stratagene). Degenerate primers were designed based on conserved amino acid-regions of known PTP sequences and were synthesized using a Gene Assembler Plus (Pharmacia-LKB). Sense oligonucleotides corresponded to the sequences SEQ ID NO:5, FWRM I/V WEQ (5'-TTCTGG A/C GNATGATNTGGGAACA-3', SEQ ID NO:6, 23mer with 32-fold degeneracy) and SEQ ID NO:7 KC A/D Q/E YWP (5'-AA A/G TG C/T GANCAGTA C/T TGGCC-3', SEQ ID NO:8 20mer with 32-fold degeneracy), and the anti-sense oligonucleotide was based on the sequence SEQ ID NO:9 HCSAG V/I G (5'-CCNACNCC A/C GC A/G CTGCAGTG-3', 20mer with 64-fold degeneracy). Unpackaged template cDNA from the U-343 MGa 31L library (100 ng) was amplified using Tag polymerase (Perkin Elmer-Cetus) and 100 nq of either sense primer in combination with 100 ng of the anti-sense primer as described (Saiki et al., 1985). PCR was carried out for 25 cycles each consisting of denaturation at 94° C. for 30 sec, annealing at 40° C. for 2 min followed by 55° C. for 1 min, and extension at 72° C. for 2 min. The PCR products were separated on a 2.0% low gelling temperature agarose gel (FMC BioProducts, Rockland, USA) and DNA fragments of approximately 368 base pairs (with FWRM sense primer SEQ ID NO:6) and approximately 300 bp (with KC A/D Q sense primer) were excised, eluted from the gel, subcloned into a T-tailed vector (TA Cloning Kit, Invitrogen Corporation, San Diego, Calif., USA), and sequenced.

Nucleotide sequences from several of the PCR cDNA clones analysed were representative of both cytoplasmic and receptor types of PTPs. Thirteen clones encoded cytoplasmic enzymes including MEG (Gu et al., 1991; 8 clones), PTPH1 (Yang and Tonks, 1991; 2 clones), P19PTP (den Hertog et al., 1992), and TC-PTP (Cool et al., 1989, one clone); 11 clones encoded receptor-type enzymes such as HPTP-α (Kruger et al., 1990, 7 clones), HPTP-γ (Kruger et al., 1990, 3 clones) and HPTP-δ (Kruger et al., 1990, 1 clone), and three clones defined novel PTP sequences. Two of these were named PTPL1 and GLM-2.

The U-343 MGa 31L cDNA library was screened with $^{32}$P-random prime-labeled (Megaprime Kit, Amersham) approximately 368 bp inserts corresponding to PTPL1 as described elsewhere (Huynh et al., 1986); clone λ6.15 was isolated, excised from purified phage DNA by Eco RI (Biolabs) digestion and subcloned into pUC18 for sequencing. All other cDNA clones were isolated from the AG1518 human fibroblast cDNA library which was screened with $^{32}$P-labeled λ6.15 insert and with subsequently isolated partial cDNA clones.

Double-stranded plasmid DNA was prepared by a single-tube mini preparation method (Del Sal et al., 1988) or using Magic mini or maxiprep kits (Promega) according to the manufacturer's specifications. Double-stranded DNA was denatured and used as template for sequencing by the dideoxynucleotide chain-termination procedure with T7 DNA polymerase (Pharmacia-LKB), and M13-universal and reverse primers or synthetic oligonucleotides derived from the cDNA sequences being determined. The complete 7395 bp open reading frame of PTPL1, was derived from six overlapping cDNA clones totalling 8040 bp and predicts a protein of 2465 amino acids with an approximate molecular mass of 275 kDa. The 8040 bp sequence is disclosed as SEQ ID NO.:1.

EXAMPLE 2

Original Cloning of GLM-2

The human glioma cell line U-343 MGa 31L (Nister, M., et al., (1988) *Cancer Res.* 48:3910–3918) was cultured in Dulbecco's Modified Eagles Medium (DMEM Gibco) supplemented with 10% Fetal Calf Serum (FCS, Flow Laboratories), 100 units of penicillin, 50 μg/ml streptomycin and 2 mM glutamine.

Total RNA was prepared from U-343 MGa 31L cells by guanidine thiocyanate (Merck, Darmstadt) extraction (Chirgwin, et al., 1979). Briefly, cells were harvested, washed in phosphate buffered saline (PBS), and lysed in 4M guanidine thiocyanate containing 25 mM sodium citrate (pH 7.0) and 0.1M 2-mercaptoethanol. RNA was sedimented through 5.7M cesium chloride, the RNA pellet was then dissolved in 10 mM Tris hydrochloride (pH 7.5), 5 mM EDTA (TE buffer), extracted with phenol and chloroform, precipitated with ethanol, and the final pellet stored at −70° C. or resuspended in TE buffer for subsequent manipulations. Polyadenylated [poly(A)+] RNA was prepared by chromatography on oligo (dT)-cellulose as described in Maniatis et al. (1982).

Poly(A)+ RNA (5 μg) isolated from U-343 MGa 31L cells was used to make a cDNA library by oligo (dT)-primed cDNA synthesis using an Amersham λgt10 cDNA cloning system. Degenerate primers were designed based on conserved amino acid regions of known PTP sequences, and synthesized using a Gene Assembler Plus (Pharmacia-LKB). Sense oligonucleotides corresponded to the sequences SEQ ID NO:5 FWRM I/V WEQ (5'-TTCTGG A/C GNATGATNTGGGAACA-3', SEQ ID NO:6 23mer with 32-fold degeneracy=primer P1) and SEQ ID NO:7 KC A/D Q/E YWP (5'-AA A/G TG C/T GANCAGTA C/T TGGCC-3', SEQ ID NO:8 20mer with 32-fold degeneracy=primer P2), and the anti-sense oligonucleotide was based on the sequence SEQ ID NO:9 HCSAG V/I G (5'-CCNACNCC A/C GC A/G CTGCAGTG-3', SEQ ID NO:10 20mer with 64-fold degeneracy=primer P3). Unpackaged template cDNA from the U-343 MGa 31L library (100 ng) was amplified using Tag polymerase (Perkin Elmer-Cetus) and 100 ng of either sense primer in combination with 100 ng of the anti-sense primer as described (Saiki, et al., 1985). PCR was carried out for 25 cycles each consisting of denaturation at 94° C. for 30 sec, annealing at 40° C. for 2 min followed by 55° C. for 1 min, and extension at 72° C. for 2 min. The PCR products were separated on a 2.0% low gelling temperature agarose gel (FMC Bioproducts, Rockland, USA)

and DNA fragments of approximately 368 base pairs (with FWRM sense primer) and approximately 300 bp (with KC A/D Q sense primer) were excised, eluted from the gel, subcloned into a T-tailed vector (TA Cloning Kit, Invitrogen Corporation, San Diego, Calif., USA), and sequenced. Double-stranded plasmid DNA was prepared by a single-tube mini preparation method (Del Sal, et al., 1988) or by using Magic mini or maxiprep kits (Promega) according to the manufacturer's specifications. Double-stranded DNA was denatured and used as template for sequencing by the dideoxynucleotide chain-termination procedure (Sanger, et al., 1977) with T7 DNA polymerase (Pharmacia-LKB), and M13-universal and reverse primers or, in the case of cDNA clones isolated from the brain cDNA library, using also synthetic oligonucleotides derived from the cDNA sequences being determined.

A human brain cDNA library constructed in λgt10 (Clontech, Calif.) was screened as described elsewhere (Huynh, et al., 1986) with $^{32}$P-random prime-labeled (Megaprime Kit, Amersham) approximately 360 bp inserts corresponding to GLM-2. Clone HBM1 was isolated, excised from purified phage DNA by Eco RI (Biolabs) digestion and subcloned into the plasmid vectors pUC18 or Bluescript (Stratagene) for sequencing. The resulting sequence is disclosed as SEQ ID NO.: 3.

EXAMPLE 3

Tissue-Specific Expression of PTPL1

Total RNA (20 μg) or poly(A)+ RNA (2 μg) denatured in formaldehyde and formamide was separated by electrophoresis on a formaldehyde/1% agarose gel and transferred to nitrocellulose. The filters were hybridized for 16 hrs at 42° C. with $^{32}$P-labeled probes in a solution containing 5× standard saline citrate (SSC; 1× SSC is 50 mM sodium citrate, pH 7.0, 150 mM sodium chloride), 50% formamide, 0.1% sodium dodecyl sulfate (SDS), 50 mM sodium phosphate and 0.1 mg/ml salmon sperm DNA. All probes were labeled by random priming (Feinberg and Vogelstein, 1983) and unincorporated $^{32}$P was removed by Sephadex G-25 (Pharmacia-LKB) chromatography. Human tissue blots (Clontech, Calif.) were hybridized with PTPL1 specific probes according to manufacturer's specifications. Filters were washed twice for 30 min at 60° C. in 2× SSC/0.1% SDS, once for 30 min at 60° C. in 0.5× SSC/0.1% SDS, and exposed to X-ray film (Fuji, XR) with intensifying screen (Cronex Lighting Plus, Dupont) at −70° C.

Northern blot analysis of RNAs from various human tissues showed that the 9.5 kb PTPL1 transcript is expressed at different levels with kidney, placenta, ovaries and testes showing high expression, compared to medium expression in lung, pancreas, prostate and brain tissues, low in heart, skeletal muscle, spleen, liver, small intestine and colon and virtually no detectable expression in leukocytes.

EXAMPLE 4

Tissue-Specific Expression of GLM-2

To investigate the expression of GLM-2 mRNA in human tissues, Northern blot analysis was performed on a commercially available filter (Clontech, Calif.) containing mRNAs from human heart, brain, placenta, lung, liver, skeletal muscle, kidney and pancreas tissue. The filter was hybridized according to manufacturer's specifications with $^{32}$P-labeled GLM-2 PCR product as probe, washed twice for 30 min at 60° C. in 2× standard saline citrate (SSC; 1× SSC is 50 mM sodium citrate, pH 7.0, 150 mM sodium chloride), containing 0.1% sodium dodecyl sulfate (SDS), once for 30 min at 60° C. in 0.5× SSC/0.1% SDS, and exposed to X-ray film (Fuji, RX) with intensifying screen (Cronex Lighting Plus, Dupont) at −70° C.

EXAMPLE 5

Production of PTPL1 specific antisera

Rabbit antisera denoted αL1A and αL1B were prepared against peptides corresponding to amino acid residues 1802 to 1823 SEQ ID NO:1 (PAKSDGRLKPGDRLIKVNDTDV) and 450 to 470 SEQ ID NO:1, (DETLSQGQSQRPSRQYETPFE), respectively, of PTPL1. The peptides were synthesized in an Applied Biosystems 430A Peptide Synthesizer using t-butoxycarbonyl chemistry and purified by reverse phase high performance liquid chromatography. The peptides were coupled to keyhole limpet hemocyanin (Calbiochem-Behring) using glutaraldehyde, as described (Gullick, W. J., et al., (1985) *EMBO J.* 4:2869–2877), and then mixed with Freund's adjuvant and used to Immunize a rabbit. The αL1A antiserum was purified by affinity chomatography on protein A-Sepharose CL4B (Pharmacia-LKB) as described by the manufacturer.

EXAMPLE 6

Transfection of the PTPL1 cDNA Into COS-1 Cells

The full length PTPL1 cDNA was constructed using overlapping clones and cloned into the SV40-based expression vector pSV7d (Truett, M. A., et al., (1985) *DNA* 4:333–349), and transfected into COS-1 cells by the calcium phosphate precipitation method (Wigler, M., et al., (1979) *Cell* 16:777–785). Briefly, cells were seeded into 6-well cell culture plates at a density of 5×10$^5$ cells/well, and transfected the following day with 10 μg of plasmid. After overnight incubation, cells were washed three times with a buffer containing 25 mM Tris-HCl, pH 7.4, 138 mM Nacl, 5 mM KCl 0.7 mM CaCl$_2$, 0.5 mM MgCl$_2$ and 0.6 mM Na$_2$HPO$_4$, and then incubated with Dulbecco's modified Eagle's medium containing 10% fetal calf serum and antibiotics. Two days after transfection, the cells were used for metabolic labeling followed by immunoprecipitation and SDS-gel electrophoresis, or immunoprecipitation followed by dephosphorylation experiments.

EXAMPLE 7

Metabolic Labeling, Immunoprecipitation and Electrophoresis of PTPL1

Metabolic labeling of COS-1 cells, AG1518 cells, PC-3 cells, CCL-64 cells, A549 cells and PAE cells was performed for 4 h in methionine- and cysteine-free MCDB 104 medium (Gibco) with 150 μCi/ml of [$^{35}$S]methionine and [$^{35}$S]cysteine (in vivo labeling mix; Amersham). After labeling, the cells were solubilized in a buffer containing 20 mM Tris-HCl, pH 7.4, 150 mM NaCl, 10 mM EDTA, 0.5% Triton X-100, 0.5% deoxycholate, 1.5% Trasylol (Bayer) and 1 mM phenylmethylsulfonyl fluoride (PMSF; Sigma). After 15 min on ice, cell debris was removed by centrifugation. Samples (1 ml) were then incubated for 1.5 h at 4° C. with either αL1A antibodies or αL1A antibodies preblocked with 10 μg of peptide. Immune complexes were then mixed with 50 μl of a protein A-Sepharose (Pharmacia-LKB) slurry (50% packed beads in 150 mM NaCl, 20 Mm Tris-HCL, pH 7.4, 0.2% Triton X-100) and incubated for 45 min at 4° C. The beads were pelleted and washed four times with washing buffer (20 mM Tris-HCl, pH 7.4, 500 mM NaCl, 1% Triton X-100, 1% deoxycholate and 0.2% SDS), followed by one wash in distilled water. The immune complexes were eluted by boiling for 5 min in the SDS-sample buffer (100 mM Tris-HCl, pH 8.8, 0.01% bromophenol blue, 36% glycerol, 4% SDS) in the presence of 10 mM dithiothreitol (DTT), and analyzed by SDS-gel electrophoresis using 4–7% polyacrylamide gels (Blobel, G., and Dobberstein, B. (1975) *J. Cell Biol.* 67:835–851). The gel was fixed, incubated with Amplify (Amersham) for 20 min, dried and subjected to fluorography.

EXAMPLE 8

Dephosphorylation Assay for PTPL1

COS-1 cells were lysed in 20 mM Tris-HCl, pH 7.4, 150 mM NaCl, 10 mM EDTA, 0.5% Triton X-100, 0.5% deoxycholate, 1.5% Trasylol, 1 mM PMSF and 1 mM DTT, for 15 min. Lysates were cleared by centrifugation, 3 μl of the antiserum αL1B, with or without preblocking with 10 μg peptide, were added and samples were incubated for 2 h at 4° C. Protein A-Sepharose slurry (25 μl) was then added and incubation was prolonged another 30 min at 4° C. The beads were pelleted and washed four times with lysis buffer and one time with dephosphorylation assay buffer (25 mM imidazole-HCl, pH 7.2, 1 mg/ml bovine serum albumin and 1 mM DTT), and finally resuspended in dephosphorylation assay buffer containing 2 μM myelin basic protein $^{32}$P-labeled on tyrosine residues by Baculo-virus expressed intracellular part of the insulin receptor, kindly provided by A. J. Flint (Cold Spring Harbor Laboratory) and M. M. Cobb (University of Texas). After incubation for indicated times at 30° C., the reactions were stopped with a charcoal mixture (Streull, M., et al., (1988) *J. Exp. Med.* 168:1523–1530) and the radioactivity in the supernatants was determined by Cerenkov counting. For each sample, lysate corresponding to 5 cm$^2$ of confluent cells was used.

It should be understood that the preceding is merely a detailed description of certain preferred embodiments and examples of particular laboratory embodiments. It therefore should be apparent to those skilled in the art that various modifications and equivalents can be made without departing from the spirit or scope of the invention as definded in the appended claims.

---

We claim:

1. An isolated nucleic acid molecule comprising a nucleotide sequence selected from the group consisting of
   (a) nucleotide sequences which hybridize under high stringency conditions to a nucleic acid molecule consiting of the nucleotide sequence of SEQ ID NO:1, and which encodes a naturally occurring PTPL1 protein tyrosine phosphatase, and
   (b) nucleotide sequences that differ from the nucleotide sequences of (a) in codon sequence due to the degeneracy of the genetic code.

2. The isolated nucleic acid molecule of claim 1, wherein said isolated nucleic acid molecule encodes a PTPL1 comprising the amino acid sequence as set forth in SEQ ID NO:3.

3. The isolated nucleic acid molecule of claim 1 wherein said nucleotide sequence comprises SEQ ID NO.:1.

4. A method of detecting compounds which increase or decrease expression or phosphatase activity of a PTPL1 protein tyrosine phosphatase encoded by the nucleic acid molecule of claim 1 comprising the steps of
   (a) determining a control amount of PTPL1 protein tyrosine phosphatase expression or phosphatase activity in a cell which expresses said PTPL1 protein tyrosine phosphatase;
   (b) contacting the cell which expresses said PTPL1 protein tyrosine phosphatase with a test compound;
   (c) measuring the expression or phosphatase activity of said PTPL1 protein tyrosine phosphatase in said cell contacted with the test compound; and
   (d) comparing the expression or phosphatase activity of said PTPL1 protein tyrosine phosphatase measured in (c) with the control amount of PTPL1 protein tyrosine phosphatase expression or phosphatase activity determined in (a) for an indication of the increase or decrease of expression or phosphatase activity of said PTPL1 protein tyrosine phosphatase.

5. The method of claim 4 wherein expression of said PTPL1 protein tyrosine phosphatase is measured.

6. The method of claim 4 wherein phosphatase activity of said PTPL1 protein tyrosine phosphatase is measured.

7. An isolated PTPL1 protein tyrosine phosphatase encoded by the nucleic acid molecule of claim 1 or claim 3.

8. An isolated nucleic acid molecule comprising a nucleic acid molecule complementary to the isolated nucleic acid molecule of claim 1.

9. The isolated nucleic acid molecule of any one of claims 1–3 and 8 wherein said nucleotide sequence is operably joined to a regulatory sequence.

10. A substantially pure protein comprising a PTPL1 protein tyrosine phosphatase wherein said PTPL1 comprises an amino acid sequence selected from the group consisting of the amino acid sequence as set forth in SEQ ID NO.:3 and a naturally occurring allelic variant of the amino acid sequence as set forth in SEQ ID NO.:3.

11. The substantially pure protein of claim 10 wherein said amino acid sequence comprises the amino acid sequence as forth in SEQ ID NO:3.

12. A method for determining whether a compound increases or decreases the phosphatase activity of a PTPL1 protein tyrosine phosphatase encoded by the nucleic acid molecule of claim 1, comprising (a) determining a control amount of phosphatase activity of the PTPL1 protein tyrosine phosphatase, (b) contacting the PTPL1 protein tyrosine phosphatase with the compound, (c) measuring the phosphatase activity of the PTPL1 protein tyrosine phosphatase, and (d) comparing the phosphatase activity measured in (c) with the control amount of phosphatase activity determined in (a) as an indication whether the compound increases or decreases the phosphatase activity of the PTPL1 protein tyrosine phosphatase.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 8040 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: HOMO SAPIENS ( i x ) FEATURE:
        ( A ) NAME/KEY: CDS
        ( B ) LOCATION: 78..7475

( x i ) SEQUENCE DESCRIPTION: SEQ ID NO:1:

```
CCCGCCCCGA  CGCCGCGTCC  CTGCAGCCCT  GCCCGGCGCT  CCAGTAGCAG  GACCCGGTCT                60

CGGGACCAGC  CGGTAAT ATG CAC GTG TCA CTA GCT GAG GCC CTG GAG GTT                       110
                    Met His Val Ser Leu Ala Glu Ala Leu Glu Val
                    1               5                       10

CGG GGT GGA CCA CTT CAG GAG GAA GAA ATA TGG GCT GTA TTA AAT CAA                       158
Arg Gly Gly Pro Leu Gln Glu Glu Glu Ile Trp Ala Val Leu Asn Gln
            15                  20                  25

AGT GCT GAA AGT CTC CAA GAA TTA TTC AGA AAA GTA AGC CTA GCT GAT                       206
Ser Ala Glu Ser Leu Gln Glu Leu Phe Arg Lys Val Ser Leu Ala Asp
        30                      35                  40

CCT GCT GCC CTT GGC TTC ATC ATT TCT CCA TGG TCT CTG CTG TTG CTG                       254
Pro Ala Ala Leu Gly Phe Ile Ile Ser Pro Trp Ser Leu Leu Leu Leu
    45                      50                      55

CCA TCT GGT AGT GTG TCA TTT ACA GAT GAA AAT ATT TCC AAT CAG GAT                       302
```

|     |     |     |     |     |     |     |     |     |     |     |     |     |     |     |     |
| --- | --- | --- | --- | --- | --- | --- | --- | --- | --- | --- | --- | --- | --- | --- | --- |
| Pro | Ser | Gly | Ser | Val | Ser | Phe | Thr | Asp | Glu | Asn | Ile | Ser | Asn | Gln | Asp |
| 60  |     |     |     |     | 65  |     |     |     | 70  |     |     |     |     | 75  |     |

| CTT | CGA | GCA | TTC | ACT | GCA | CCA | GAG | GTT | CTT | CAA | AAT | CAG | TCA | CTA | ACT | 350 |
| --- | --- | --- | --- | --- | --- | --- | --- | --- | --- | --- | --- | --- | --- | --- | --- | --- |
| Leu | Arg | Ala | Phe | Thr | Ala | Pro | Glu | Val | Leu | Gln | Asn | Gln | Ser | Leu | Thr |     |
|     |     |     |     | 80  |     |     |     |     | 85  |     |     |     |     | 90  |     |     |

| TCT | CTC | TCA | GAT | GTT | GAA | AAG | ATC | CAC | ATT | TAT | TCT | CTT | GGA | ATG | ACA | 398 |
| --- | --- | --- | --- | --- | --- | --- | --- | --- | --- | --- | --- | --- | --- | --- | --- | --- |
| Ser | Leu | Ser | Asp | Val | Glu | Lys | Ile | His | Ile | Tyr | Ser | Leu | Gly | Met | Thr |     |
|     |     |     | 95  |     |     |     |     | 100 |     |     |     |     | 105 |     |     |     |

| CTG | TAT | TGG | GGG | GCT | GAT | TAT | GAA | GTG | CCT | CAG | AGC | CAA | CCT | ATT | AAG | 446 |
| --- | --- | --- | --- | --- | --- | --- | --- | --- | --- | --- | --- | --- | --- | --- | --- | --- |
| Leu | Tyr | Trp | Gly | Ala | Asp | Tyr | Glu | Val | Pro | Gln | Ser | Gln | Pro | Ile | Lys |     |
|     |     | 110 |     |     |     |     | 115 |     |     |     |     | 120 |     |     |     |     |

| CTT | GGA | GAT | CAT | CTC | AAC | AGC | ATA | CTG | CTT | GGA | ATG | TGT | GAG | GAT | GTT | 494 |
| --- | --- | --- | --- | --- | --- | --- | --- | --- | --- | --- | --- | --- | --- | --- | --- | --- |
| Leu | Gly | Asp | His | Leu | Asn | Ser | Ile | Leu | Leu | Gly | Met | Cys | Glu | Asp | Val |     |
|     | 125 |     |     |     |     | 130 |     |     |     |     | 135 |     |     |     |     |     |

| ATT | TAC | GCT | CGA | GTT | TCT | GTT | CGG | ACT | GTG | CTG | GAT | GCT | TGC | AGT | GCC | 542 |
| --- | --- | --- | --- | --- | --- | --- | --- | --- | --- | --- | --- | --- | --- | --- | --- | --- |
| Ile | Tyr | Ala | Arg | Val | Ser | Val | Arg | Thr | Val | Leu | Asp | Ala | Cys | Ser | Ala |     |
| 140 |     |     |     |     | 145 |     |     |     |     | 150 |     |     |     |     | 155 |     |

| CAC | ATT | AGG | AAT | AGC | AAT | TGT | GCA | CCC | TCA | TTT | TCC | TAC | GTG | AAA | CAC | 590 |
| --- | --- | --- | --- | --- | --- | --- | --- | --- | --- | --- | --- | --- | --- | --- | --- | --- |
| His | Ile | Arg | Asn | Ser | Asn | Cys | Ala | Pro | Ser | Phe | Ser | Tyr | Val | Lys | His |     |
|     |     |     |     | 160 |     |     |     |     | 165 |     |     |     |     | 170 |     |     |

| TTG | GTA | AAA | CTG | GTT | CTG | GGA | AAT | CTT | TCT | GGG | ACA | GAT | CAG | CTT | TCC | 638 |
| --- | --- | --- | --- | --- | --- | --- | --- | --- | --- | --- | --- | --- | --- | --- | --- | --- |
| Leu | Val | Lys | Leu | Val | Leu | Gly | Asn | Leu | Ser | Gly | Thr | Asp | Gln | Leu | Ser |     |
|     |     |     | 175 |     |     |     |     | 180 |     |     |     |     | 185 |     |     |     |

| TGT | AAC | AGT | GAA | CAA | AAG | CCT | GAT | CGA | AGC | CAG | GCT | ATT | CGA | GAT | CGA | 686 |
| --- | --- | --- | --- | --- | --- | --- | --- | --- | --- | --- | --- | --- | --- | --- | --- | --- |
| Cys | Asn | Ser | Glu | Gln | Lys | Pro | Asp | Arg | Ser | Gln | Ala | Ile | Arg | Asp | Arg |     |
|     |     | 190 |     |     |     |     | 195 |     |     |     |     | 200 |     |     |     |     |

| TTG | CGA | GGA | AAA | GGA | TTA | CCA | ACA | GGA | AGA | AGC | TCT | ACT | TCT | GAT | GTA | 734 |
| --- | --- | --- | --- | --- | --- | --- | --- | --- | --- | --- | --- | --- | --- | --- | --- | --- |
| Leu | Arg | Gly | Lys | Gly | Leu | Pro | Thr | Gly | Arg | Ser | Ser | Thr | Ser | Asp | Val |     |
|     | 205 |     |     |     |     | 210 |     |     |     |     | 215 |     |     |     |     |     |

| CTA | GAC | ATA | CAA | AAG | CCT | CCA | CTC | TCT | CAT | CAG | ACC | TTT | CTT | AAC | AAA | 782 |
| --- | --- | --- | --- | --- | --- | --- | --- | --- | --- | --- | --- | --- | --- | --- | --- | --- |
| Leu | Asp | Ile | Gln | Lys | Pro | Pro | Leu | Ser | His | Gln | Thr | Phe | Leu | Asn | Lys |     |
| 220 |     |     |     |     | 225 |     |     |     |     | 230 |     |     |     |     | 235 |     |

| GGG | CTT | AGT | AAA | TCT | ATG | GGA | TTT | CTG | TCC | ATC | AAA | GAT | ACA | CAA | GAT | 830 |
| --- | --- | --- | --- | --- | --- | --- | --- | --- | --- | --- | --- | --- | --- | --- | --- | --- |
| Gly | Leu | Ser | Lys | Ser | Met | Gly | Phe | Leu | Ser | Ile | Lys | Asp | Thr | Gln | Asp |     |
|     |     |     |     | 240 |     |     |     |     | 245 |     |     |     |     | 250 |     |     |

| GAG | AAT | TAT | TTC | AAG | GAC | ATT | TTA | TCA | GAT | AAT | TCT | GGA | CGT | GAA | GAT | 878 |
| --- | --- | --- | --- | --- | --- | --- | --- | --- | --- | --- | --- | --- | --- | --- | --- | --- |
| Glu | Asn | Tyr | Phe | Lys | Asp | Ile | Leu | Ser | Asp | Asn | Ser | Gly | Arg | Glu | Asp |     |
|     |     |     | 255 |     |     |     |     | 260 |     |     |     |     | 265 |     |     |     |

| TCT | GAA | AAT | ACA | TTC | TGC | CCT | TAC | CAG | TTC | AAA | ACT | AGT | GGC | CCA | GAA | 926 |
| --- | --- | --- | --- | --- | --- | --- | --- | --- | --- | --- | --- | --- | --- | --- | --- | --- |
| Ser | Glu | Asn | Thr | Phe | Cys | Pro | Tyr | Gln | Phe | Lys | Thr | Ser | Gly | Pro | Glu |     |
|     |     | 270 |     |     |     |     | 275 |     |     |     |     | 280 |     |     |     |     |

| AAA | AAA | CCC | ATC | CCT | GGC | ATT | GAT | GTG | CTT | TCT | AAG | AAG | AAG | ATC | TGG | 974 |
| --- | --- | --- | --- | --- | --- | --- | --- | --- | --- | --- | --- | --- | --- | --- | --- | --- |
| Lys | Lys | Pro | Ile | Pro | Gly | Ile | Asp | Val | Leu | Ser | Lys | Lys | Lys | Ile | Trp |     |
|     | 285 |     |     |     |     | 290 |     |     |     |     | 295 |     |     |     |     |     |

| GCT | TCA | TCC | ATG | GAC | TTG | CTT | TGT | ACA | GCT | GAC | AGA | GAC | TTC | TCT | TCA | 1022 |
| --- | --- | --- | --- | --- | --- | --- | --- | --- | --- | --- | --- | --- | --- | --- | --- | --- |
| Ala | Ser | Ser | Met | Asp | Leu | Leu | Cys | Thr | Ala | Asp | Arg | Asp | Phe | Ser | Ser |     |
| 300 |     |     |     |     | 305 |     |     |     |     | 310 |     |     |     |     | 315 |     |

| GGA | GAG | ACT | GCC | ACA | TAT | CGT | CGT | TGT | CAC | CCT | GAG | GCA | GTA | ACA | GTG | 1070 |
| --- | --- | --- | --- | --- | --- | --- | --- | --- | --- | --- | --- | --- | --- | --- | --- | --- |
| Gly | Glu | Thr | Ala | Thr | Tyr | Arg | Arg | Cys | His | Pro | Glu | Ala | Val | Thr | Val |     |
|     |     |     |     | 320 |     |     |     |     | 325 |     |     |     |     | 330 |     |     |

| CGG | ACT | TCA | ACT | ACG | CCT | AGA | AAA | AAG | GAG | GCA | AGA | TAC | TCA | GAT | GGA | 1118 |
| --- | --- | --- | --- | --- | --- | --- | --- | --- | --- | --- | --- | --- | --- | --- | --- | --- |
| Arg | Thr | Ser | Thr | Thr | Pro | Arg | Lys | Lys | Glu | Ala | Arg | Tyr | Ser | Asp | Gly |     |
|     |     |     |     | 335 |     |     |     |     | 340 |     |     |     |     | 345 |     |     |

| AGT | ATA | GCC | TTG | GAT | ATC | TTT | GGC | CCT | CAG | AAA | ATG | GAT | CCA | ATA | TAT | 1166 |
| --- | --- | --- | --- | --- | --- | --- | --- | --- | --- | --- | --- | --- | --- | --- | --- | --- |
| Ser | Ile | Ala | Leu | Asp | Ile | Phe | Gly | Pro | Gln | Lys | Met | Asp | Pro | Ile | Tyr |     |
|     |     | 350 |     |     |     |     | 355 |     |     |     |     | 360 |     |     |     |     |

| CAC | ACT | CGA | GAA | TTG | CCC | ACC | TCC | TCA | GCA | ATA | TCA | AGT | GCT | TTG | GAC | 1214 |
| --- | --- | --- | --- | --- | --- | --- | --- | --- | --- | --- | --- | --- | --- | --- | --- | --- |
| His | Thr | Arg | Glu | Leu | Pro | Thr | Ser | Ser | Ala | Ile | Ser | Ser | Ala | Leu | Asp |     |
|     |     | 365 |     |     |     |     | 370 |     |     |     |     | 375 |     |     |     |     |

| CGA | ATC | CGA | GAG | AGA | CAA | AAG | AAA | CTT | CAG | GTT | CTG | AGG | GAA | GCC | ATG | 1262 |
| --- | --- | --- | --- | --- | --- | --- | --- | --- | --- | --- | --- | --- | --- | --- | --- | --- |

```
Arg Ile Arg Glu Arg Gln Lys Lys Leu Gln Val Leu Arg Glu Ala Met
380             385             390             395

AAT GTA GAA GAA CCA GTT CGA AGA TAC AAA ACT TAT CAT GGT GAT GTC      1310
Asn Val Glu Glu Pro Val Arg Arg Tyr Lys Thr Tyr His Gly Asp Val
            400             405             410

TTT AGT ACC TCC AGT GAA AGT CCA TCT ATT ATT TCC TCT GAA TCA GAT      1358
Phe Ser Thr Ser Ser Glu Ser Pro Ser Ile Ile Ser Ser Glu Ser Asp
            415             420             425

TTC AGA CAA GTG AGA AGA AGT GAA GCC TCA AAG AGG TTT GAA TCC AGC      1406
Phe Arg Gln Val Arg Arg Ser Glu Ala Ser Lys Arg Phe Glu Ser Ser
            430             435             440

AGT GGT CTC CCA GGG GTA GAT GAA ACC TTA AGT CAA GGC CAG TCA CAG      1454
Ser Gly Leu Pro Gly Val Asp Glu Thr Leu Ser Gln Gly Gln Ser Gln
    445             450             455

AGA CCG AGC AGA CAA TAT GAA ACA CCC TTT GAA GGC AAC TTA ATT AAT      1502
Arg Pro Ser Arg Gln Tyr Glu Thr Pro Phe Glu Gly Asn Leu Ile Asn
460             465             470             475

CAA GAG ATC ATG CTA AAA CGG CAA GAG GAA GAA CTG ATG CAG CTA CAA      1550
Gln Glu Ile Met Leu Lys Arg Gln Glu Glu Glu Leu Met Gln Leu Gln
            480             485             490

GCC AAA ATG GCC CTT AGA CAG TCT CGG TTG AGC CTA TAT CCA GGA GAC      1598
Ala Lys Met Ala Leu Arg Gln Ser Arg Leu Ser Leu Tyr Pro Gly Asp
            495             500             505

ACA ATC AAA GCG TCC ATG CTT GAC ATC ACC AGG GAT CCG TTA AGA GAA      1646
Thr Ile Lys Ala Ser Met Leu Asp Ile Thr Arg Asp Pro Leu Arg Glu
    510             515             520

ATT GCC CTA GAA ACA GCC ATG ACT CAA AGA AAA CTG AGG AAT TTC TTT      1694
Ile Ala Leu Glu Thr Ala Met Thr Gln Arg Lys Leu Arg Asn Phe Phe
525             530             535

GGC CCT GAG TTT GTG AAA ATG ACA ATT GAA CCA TTT ATA TCT TTG GAT      1742
Gly Pro Glu Phe Val Lys Met Thr Ile Glu Pro Phe Ile Ser Leu Asp
540             545             550             555

TTG CCA CGG TCT ATT CTT ACT AAG AAA GGG AAG AAT GAG GAT AAC CGA      1790
Leu Pro Arg Ser Ile Leu Thr Lys Lys Gly Lys Asn Glu Asp Asn Arg
            560             565             570

AGG AAA GTA AAC ATA ATG CTT CTG AAC GGG CAA AGA CTG GAA CTG ACC      1838
Arg Lys Val Asn Ile Met Leu Leu Asn Gly Gln Arg Leu Glu Leu Thr
            575             580             585

TGT GAT ACC AAA ACT ATA TGT AAA GAT GTG TTT GAT ATG GTT GTG GCA      1886
Cys Asp Thr Lys Thr Ile Cys Lys Asp Val Phe Asp Met Val Val Ala
        590             595             600

CAT ATT GGC TTA GTA GAG CAT CAT TTG TTT GCT TTA GCT ACC CTC AAA      1934
His Ile Gly Leu Val Glu His His Leu Phe Ala Leu Ala Thr Leu Lys
    605             610             615

GAT AAT GAA TAT TTC TTT GTT GAT CCT GAC TTA AAA TTA ACC AAA GTG      1982
Asp Asn Glu Tyr Phe Phe Val Asp Pro Asp Leu Lys Leu Thr Lys Val
620             625             630             635

GCC CCA GAG GGA TGG AAA GAA GAA CCA AAG AAA AAG ACC AAA GCC ACT      2030
Ala Pro Glu Gly Trp Lys Glu Glu Pro Lys Lys Lys Thr Lys Ala Thr
            640             645             650

GTT AAT TTT ACT TTG TTT TTC AGA ATT AAA TTT TTT ATG GAT GAT GTT      2078
Val Asn Phe Thr Leu Phe Phe Arg Ile Lys Phe Phe Met Asp Asp Val
            655             660             665

AGT CTA ATA CAA CAT ACT CTG ACG TGT CAT CAG TAT TAC CTT CAG CTT      2126
Ser Leu Ile Gln His Thr Leu Thr Cys His Gln Tyr Tyr Leu Gln Leu
        670             675             680

CGA AAA GAT ATT TTG GAG GAA AGG ATG CAC TGT GAT GAT GAG ACT TCC      2174
Arg Lys Asp Ile Leu Glu Glu Arg Met His Cys Asp Asp Glu Thr Ser
    685             690             695

TTA TTG CTG GCA TCC TTG GCT CTC CAG GCT GAG TAT GGA GAT TAT CAA      2222
```

-continued

| | | | | | | | | | | | | | | | |
|---|---|---|---|---|---|---|---|---|---|---|---|---|---|---|---|
| Leu | Leu | Leu | Ala | Ser | Leu | Ala | Leu | Gln | Ala | Glu | Tyr | Gly | Asp | Tyr | Gln |
| 700 | | | | | 705 | | | | 710 | | | | | | 715 |

| | | | | | | | | | | | | | | | | |
|---|---|---|---|---|---|---|---|---|---|---|---|---|---|---|---|---|
| CCA | GAG | GTT | CAT | GGT | GTG | TCT | TAC | TTT | AGA | ATG | GAG | CAC | TAT | TTG | CCC | 2270 |
| Pro | Glu | Val | His | Gly | Val | Ser | Tyr | Phe | Arg | Met | Glu | His | Tyr | Leu | Pro | |
| | | | | 720 | | | | | 725 | | | | | 730 | | |

| GCC | AGA | GTG | ATG | GAG | AAA | CTT | GAT | TTA | TCC | TAT | ATC | AAA | GAA | GAG | TTA | 2318 |
|---|---|---|---|---|---|---|---|---|---|---|---|---|---|---|---|---|
| Ala | Arg | Val | Met | Glu | Lys | Leu | Asp | Leu | Ser | Tyr | Ile | Lys | Glu | Glu | Leu | |
| | | | 735 | | | | | 740 | | | | | 745 | | | |

| CCC | AAA | TTG | CAT | AAT | ACC | TAT | GTG | GGA | GCT | TCT | GAA | AAA | GAG | ACA | GAG | 2366 |
|---|---|---|---|---|---|---|---|---|---|---|---|---|---|---|---|---|
| Pro | Lys | Leu | His | Asn | Thr | Tyr | Val | Gly | Ala | Ser | Glu | Lys | Glu | Thr | Glu | |
| | | | 750 | | | | | 755 | | | | | 760 | | | |

| TTA | GAA | TTT | TTA | AAG | GTC | TGC | CAA | AGA | CTG | ACA | GAA | TAT | GGA | GTT | CAT | 2414 |
|---|---|---|---|---|---|---|---|---|---|---|---|---|---|---|---|---|
| Leu | Glu | Phe | Leu | Lys | Val | Cys | Gln | Arg | Leu | Thr | Glu | Tyr | Gly | Val | His | |
| | 765 | | | | | 770 | | | | | 775 | | | | | |

| TTT | CAC | CGA | GTG | CAC | CCT | GAG | AAG | AAG | TCA | CAA | ACA | GGA | ATA | TTG | CTT | 2462 |
|---|---|---|---|---|---|---|---|---|---|---|---|---|---|---|---|---|
| Phe | His | Arg | Val | His | Pro | Glu | Lys | Lys | Ser | Gln | Thr | Gly | Ile | Leu | Leu | |
| 780 | | | | | 785 | | | | | 790 | | | | | 795 | |

| GGA | GTC | TGT | TCT | AAA | GGT | GTC | CTT | GTG | TTT | GAA | GTT | CAC | AAT | GGA | GTG | 2510 |
|---|---|---|---|---|---|---|---|---|---|---|---|---|---|---|---|---|
| Gly | Val | Cys | Ser | Lys | Gly | Val | Leu | Val | Phe | Glu | Val | His | Asn | Gly | Val | |
| | | | | 800 | | | | | 805 | | | | | 810 | | |

| CGC | ACA | TTG | GTC | CTT | CGC | TTT | CCA | TGG | AGG | GAA | ACC | AAG | AAA | ATA | TCT | 2558 |
|---|---|---|---|---|---|---|---|---|---|---|---|---|---|---|---|---|
| Arg | Thr | Leu | Val | Leu | Arg | Phe | Pro | Trp | Arg | Glu | Thr | Lys | Lys | Ile | Ser | |
| | | | 815 | | | | | 820 | | | | | 825 | | | |

| TTT | TCT | AAA | AAG | AAA | ATC | ACA | TTG | CAA | AAT | ACA | TCA | GAT | GGA | ATA | AAA | 2606 |
|---|---|---|---|---|---|---|---|---|---|---|---|---|---|---|---|---|
| Phe | Ser | Lys | Lys | Lys | Ile | Thr | Leu | Gln | Asn | Thr | Ser | Asp | Gly | Ile | Lys | |
| | | 830 | | | | | 835 | | | | | 840 | | | | |

| CAT | GGC | TTC | CAG | ACA | GAC | AAC | AGT | AAG | ATA | TGC | CAG | TAC | CTG | CTG | CAC | 2654 |
|---|---|---|---|---|---|---|---|---|---|---|---|---|---|---|---|---|
| His | Gly | Phe | Gln | Thr | Asp | Asn | Ser | Lys | Ile | Cys | Gln | Tyr | Leu | Leu | His | |
| | 845 | | | | | 850 | | | | | 855 | | | | | |

| CTC | TGC | TCT | TAC | CAG | CAT | AAG | TTC | CAG | CTA | CAG | ATG | AGA | GCA | AGA | CAG | 2702 |
|---|---|---|---|---|---|---|---|---|---|---|---|---|---|---|---|---|
| Leu | Cys | Ser | Tyr | Gln | His | Lys | Phe | Gln | Leu | Gln | Met | Arg | Ala | Arg | Gln | |
| 860 | | | | | 865 | | | | | 870 | | | | | 875 | |

| AGC | AAC | CAA | GAT | GCC | CAA | GAT | ATT | GAG | AGA | GCT | TCG | TTT | AGG | AGC | CTG | 2750 |
|---|---|---|---|---|---|---|---|---|---|---|---|---|---|---|---|---|
| Ser | Asn | Gln | Asp | Ala | Gln | Asp | Ile | Glu | Arg | Ala | Ser | Phe | Arg | Ser | Leu | |
| | | | | 880 | | | | | 885 | | | | | 890 | | |

| AAT | CTC | CAA | GCA | GAG | TCT | GTT | AGA | GGA | TTT | AAT | ATG | GGA | CGA | GCA | ATC | 2798 |
|---|---|---|---|---|---|---|---|---|---|---|---|---|---|---|---|---|
| Asn | Leu | Gln | Ala | Glu | Ser | Val | Arg | Gly | Phe | Asn | Met | Gly | Arg | Ala | Ile | |
| | | | 895 | | | | | 900 | | | | | 905 | | | |

| AGC | ACT | GGC | AGT | CTG | GCC | AGC | AGC | ACC | CTC | AAC | AAA | CTT | GCT | GTT | CGA | 2846 |
|---|---|---|---|---|---|---|---|---|---|---|---|---|---|---|---|---|
| Ser | Thr | Gly | Ser | Leu | Ala | Ser | Ser | Thr | Leu | Asn | Lys | Leu | Ala | Val | Arg | |
| | | 910 | | | | | 915 | | | | | 920 | | | | |

| CCT | TTA | TCA | GTT | CAA | GCT | GAG | ATT | CTG | AAG | AGG | CTA | TCC | TGC | TCA | GAG | 2894 |
|---|---|---|---|---|---|---|---|---|---|---|---|---|---|---|---|---|
| Pro | Leu | Ser | Val | Gln | Ala | Glu | Ile | Leu | Lys | Arg | Leu | Ser | Cys | Ser | Glu | |
| | 925 | | | | | 930 | | | | | 935 | | | | | |

| CTG | TCG | CTT | TAC | CAG | CCA | TTG | CAA | AAC | AGT | TCA | AAA | GAG | AAG | AAT | GAC | 2942 |
|---|---|---|---|---|---|---|---|---|---|---|---|---|---|---|---|---|
| Leu | Ser | Leu | Tyr | Gln | Pro | Leu | Gln | Asn | Ser | Ser | Lys | Glu | Lys | Asn | Asp | |
| 940 | | | | | 945 | | | | | 950 | | | | | 955 | |

| AAA | GCT | TCA | TGG | GAG | GAA | AAG | CCT | AGA | GAG | ATG | AGT | AAA | TCA | TAC | CAT | 2990 |
|---|---|---|---|---|---|---|---|---|---|---|---|---|---|---|---|---|
| Lys | Ala | Ser | Trp | Glu | Glu | Lys | Pro | Arg | Glu | Met | Ser | Lys | Ser | Tyr | His | |
| | | | | 960 | | | | | 965 | | | | | 970 | | |

| GAT | CTC | AGT | CAG | GCC | TCT | CTC | TAT | CCA | CAT | CGG | AAA | AAT | GTC | ATT | GTT | 3038 |
|---|---|---|---|---|---|---|---|---|---|---|---|---|---|---|---|---|
| Asp | Leu | Ser | Gln | Ala | Ser | Leu | Tyr | Pro | His | Arg | Lys | Asn | Val | Ile | Val | |
| | | | 975 | | | | | 980 | | | | | 985 | | | |

| AAC | ATG | GAA | CCC | CCA | CCA | CAA | ACC | GTT | GCA | GAG | TTG | GTG | GGA | AAA | CCT | 3086 |
|---|---|---|---|---|---|---|---|---|---|---|---|---|---|---|---|---|
| Asn | Met | Glu | Pro | Pro | Pro | Gln | Thr | Val | Ala | Glu | Leu | Val | Gly | Lys | Pro | |
| | | 990 | | | | | 995 | | | | | 1000 | | | | |

| TCT | CAC | CAG | ATG | TCA | AGA | TCT | GAT | GCA | GAA | TCT | TTG | GCA | GGA | GTG | ACA | 3134 |
|---|---|---|---|---|---|---|---|---|---|---|---|---|---|---|---|---|
| Ser | His | Gln | Met | Ser | Arg | Ser | Asp | Ala | Glu | Ser | Leu | Ala | Gly | Val | Thr | |
| | 1005 | | | | | 1010 | | | | | 1015 | | | | | |

| AAA | CTT | AAT | AAT | TCA | AAG | TCT | GTT | GCG | AGT | TTA | AAT | AGA | AGT | CCT | GAA | 3182 |
|---|---|---|---|---|---|---|---|---|---|---|---|---|---|---|---|---|

```
Lys  Leu  Asn  Asn  Ser  Lys  Ser  Val  Ala  Ser  Leu  Asn  Arg  Ser  Pro  Glu
1020                1025                1030                1035

AGG  AGG  AAA  CAT  GAA  TCA  GAC  TCC  TCA  TCC  ATT  GAA  GAC  CCT  GGG  CAA         3230
Arg  Arg  Lys  His  Glu  Ser  Asp  Ser  Ser  Ser  Ile  Glu  Asp  Pro  Gly  Gln
               1040                1045                1050

GCA  TAT  GTT  CTA  GAT  GTG  CTA  CAC  AAA  AGA  TGG  AGC  ATA  GTA  TCT  TCA         3278
Ala  Tyr  Val  Leu  Asp  Val  Leu  His  Lys  Arg  Trp  Ser  Ile  Val  Ser  Ser
                    1055                1060                1065

CCA  GAA  AGG  GAG  ATC  ACC  TTA  GTG  AAC  CTG  AAA  AAA  GAT  GCA  AAG  TAT         3326
Pro  Glu  Arg  Glu  Ile  Thr  Leu  Val  Asn  Leu  Lys  Lys  Asp  Ala  Lys  Tyr
          1070                1075                1080

GGC  TTG  GGA  TTT  CAA  ATT  ATT  GGT  GGG  GAG  AAG  ATG  GAG  ACT  GAC  CTA         3374
Gly  Leu  Gly  Phe  Gln  Ile  Ile  Gly  Gly  Glu  Lys  Met  Glu  Thr  Asp  Leu
               1085                1090                1095

GGC  ATA  TTT  ATC  AGC  TCA  GTT  GCC  CCT  GGA  GGA  CCA  GCT  GAC  TTC  CAT         3422
Gly  Ile  Phe  Ile  Ser  Ser  Val  Ala  Pro  Gly  Gly  Pro  Ala  Asp  Phe  His
1100                1105                1110                          1115

GGA  TGC  TTG  AAG  CCA  GGA  GAC  CGT  TTG  ATA  TCT  GTG  AAT  AGT  GTG  AGT         3470
Gly  Cys  Leu  Lys  Pro  Gly  Asp  Arg  Leu  Ile  Ser  Val  Asn  Ser  Val  Ser
               1120                1125                1130

CTG  GAG  GGA  GTC  AGC  CAC  CAT  GCT  GCA  ATT  GAA  ATT  TTG  CAA  AAT  GCA         3518
Leu  Glu  Gly  Val  Ser  His  His  Ala  Ala  Ile  Glu  Ile  Leu  Gln  Asn  Ala
               1135                1140                1145

CCT  GAA  GAT  GTG  ACA  CTT  GTT  ATC  TCT  CAG  CCA  AAA  GAA  AAG  ATA  TCC         3566
Pro  Glu  Asp  Val  Thr  Leu  Val  Ile  Ser  Gln  Pro  Lys  Glu  Lys  Ile  Ser
               1150                1155                1160

AAA  GTG  CCT  TCT  ACT  CCT  GTG  CAT  CTC  ACC  AAT  GAG  ATG  AAA  AAC  TAC         3614
Lys  Val  Pro  Ser  Thr  Pro  Val  His  Leu  Thr  Asn  Glu  Met  Lys  Asn  Tyr
               1165                1170                1175

ATG  AAG  AAA  TCT  TCC  TAC  ATG  CAA  GAC  AGT  GCT  ATA  GAT  TCT  TCT  TCC         3662
Met  Lys  Lys  Ser  Ser  Tyr  Met  Gln  Asp  Ser  Ala  Ile  Asp  Ser  Ser  Ser
1180                1185                1190                          1195

AAG  GAT  CAC  CAC  TGG  TCA  CGT  GGT  ACC  CTG  AGG  CAC  ATC  TCG  GAG  AAC         3710
Lys  Asp  His  His  Trp  Ser  Arg  Gly  Thr  Leu  Arg  His  Ile  Ser  Glu  Asn
               1200                1205                1210

TCC  TTT  GGG  CCG  TCT  GGG  GGC  CTG  CGG  GAA  GGA  AGC  CTG  AGT  TCT  CAA         3758
Ser  Phe  Gly  Pro  Ser  Gly  Gly  Leu  Arg  Glu  Gly  Ser  Leu  Ser  Ser  Gln
               1215                1220                1225

GAT  TCC  AGG  ACT  GAG  AGT  GCC  AGC  TTG  TCT  CAA  AGC  CAG  GTC  AAT  GGT         3806
Asp  Ser  Arg  Thr  Glu  Ser  Ala  Ser  Leu  Ser  Gln  Ser  Gln  Val  Asn  Gly
               1230                1235                1240

TTC  TTT  GCC  AGC  CAT  TTA  GGT  GAC  CAA  ACC  TGG  CAG  GAA  TCA  CAG  CAT         3854
Phe  Phe  Ala  Ser  His  Leu  Gly  Asp  Gln  Thr  Trp  Gln  Glu  Ser  Gln  His
1245                1250                1255

GGC  AGC  CCT  TCC  CCA  TCT  GTA  ATA  TCC  AAA  GCC  ACC  GAG  AAA  GAG  ACT         3902
Gly  Ser  Pro  Ser  Pro  Ser  Val  Ile  Ser  Lys  Ala  Thr  Glu  Lys  Glu  Thr
1260                1265                1270                          1275

TTC  ACT  GAT  AGT  AAC  CAA  AGC  AAA  ACT  AAA  AAG  CCA  GGC  ATT  TCT  GAT         3950
Phe  Thr  Asp  Ser  Asn  Gln  Ser  Lys  Thr  Lys  Lys  Pro  Gly  Ile  Ser  Asp
               1280                1285                1290

GTA  ACT  GAT  TAC  TCA  GAC  CGT  GGA  GAT  TCA  GAC  ATG  GAT  GAA  GCC  ACT         3998
Val  Thr  Asp  Tyr  Ser  Asp  Arg  Gly  Asp  Ser  Asp  Met  Asp  Glu  Ala  Thr
               1295                1300                1305

TAC  TCC  AGC  AGT  CAG  GAT  CAT  CAA  ACA  CCA  AAA  CAG  GAA  TCT  TCC  TCT         4046
Tyr  Ser  Ser  Ser  Gln  Asp  His  Gln  Thr  Pro  Lys  Gln  Glu  Ser  Ser  Ser
               1310                1315                1320

TCA  GTG  AAT  ACA  TCC  AAC  AAG  ATG  AAT  TTT  AAA  ACT  TTT  TCT  TCA  TCA         4094
Ser  Val  Asn  Thr  Ser  Asn  Lys  Met  Asn  Phe  Lys  Thr  Phe  Ser  Ser  Ser
               1325                1330                1335

CCT  CCT  AAG  CCT  GGA  GAT  ATC  TTT  GAG  GTT  GAA  CTG  GCT  AAA  AAT  GAT         4142
```

|  |  |  |  |  |  |  |  |  |  |  |  |  |  |  |  |
|--|--|--|--|--|--|--|--|--|--|--|--|--|--|--|--|
| Pro | Pro | Lys | Pro | Gly | Asp | Ile | Phe | Glu | Val | Glu | Leu | Ala | Lys | Asn | Asp |
| 1340 |  |  |  |  | 1345 |  |  |  | 1350 |  |  |  |  | 1355 |  |

```
AAC AGC TTG GGG ATA AGT GTC ACG GGA GGT GTG AAT ACG AGT GTC AGA     4190
Asn Ser Leu Gly Ile Ser Val Thr Gly Gly Val Asn Thr Ser Val Arg
            1360                1365                1370

CAT GGT GGC ATT TAT GTG AAA GAT GTT ATT CCC CAG GGA GCA GCA GAG     4238
His Gly Gly Ile Tyr Val Lys Asp Val Ile Pro Gln Gly Ala Ala Glu
                1375                1380                1385

TCT GAT GGT AGA ATT CAC AAA GGT GAT CGC GTC CTA GCT GTC AAT GGA     4286
Ser Asp Gly Arg Ile His Lys Gly Asp Arg Val Leu Ala Val Asn Gly
            1390                1395                1400

GTT AGT CTA GAA GGA GCC ACC CAT AAG CAA GCT GTG GAA ACA CTG AGA     4334
Val Ser Leu Glu Gly Ala Thr His Lys Gln Ala Val Glu Thr Leu Arg
        1405                1410                1415

AAT ACA GGA CAG GTG GTT CAT CTG TTA TTA GAA AAG GGA CAA TCT CCA     4382
Asn Thr Gly Gln Val Val His Leu Leu Leu Glu Lys Gly Gln Ser Pro
1420                1425                1430                1435

ACA TCT AAA GAA CAT GTC CCG GTA ACC CCA CAG TGT ACC CTT TCA GAT     4430
Thr Ser Lys Glu His Val Pro Val Thr Pro Gln Cys Thr Leu Ser Asp
                1440                1445                1450

CAG AAT GCC CAA GGT CAA GGC CCA GAA AAA GTG AAG AAA ACA ACT CAG     4478
Gln Asn Ala Gln Gly Gln Gly Pro Glu Lys Val Lys Lys Thr Thr Gln
            1455                1460                1465

GTC AAA GAC TAC AGC TTT GTC ACT GAA GAA AAT ACA TTT GAG GTA AAA     4526
Val Lys Asp Tyr Ser Phe Val Thr Glu Glu Asn Thr Phe Glu Val Lys
        1470                1475                1480

TTA TTT AAA AAT AGC TCA GGT CTA GGA TTC AGT TTT TCT CGA GAA GAT     4574
Leu Phe Lys Asn Ser Ser Gly Leu Gly Phe Ser Phe Ser Arg Glu Asp
    1485                1490                1495

AAT CTT ATA CCG GAG CAA ATT AAT GCC AGC ATA GTA AGG GTT AAA AAG     4622
Asn Leu Ile Pro Glu Gln Ile Asn Ala Ser Ile Val Arg Val Lys Lys
1500                1505                1510                1515

CTC TTT GCT GGA CAG CCA GCA GCA GAA AGT GGA AAA ATT GAT GTA GGA     4670
Leu Phe Ala Gly Gln Pro Ala Ala Glu Ser Gly Lys Ile Asp Val Gly
                1520                1525                1530

GAT GTT ATC TTG AAA GTG AAT GGA GCC TCT TTG AAA GGA CTA TCT CAG     4718
Asp Val Ile Leu Lys Val Asn Gly Ala Ser Leu Lys Gly Leu Ser Gln
        1535                1540                1545

CAG GAA GTC ATA TCT GCT CTC AGG GGA ACT GCT CCA GAA GTA TTC TTG     4766
Gln Glu Val Ile Ser Ala Leu Arg Gly Thr Ala Pro Glu Val Phe Leu
    1550                1555                1560

CTT CTC TGC AGA CCT CCA CCT GGT GTG CTA CCG GAA ATT GAT ACT GCG     4814
Leu Leu Cys Arg Pro Pro Pro Gly Val Leu Pro Glu Ile Asp Thr Ala
        1565                1570                1575

CTT TTG ACC CCA CTT CAG TCT CCA GCA CAA GTA CTT CCA AAC AGC AGT     4862
Leu Leu Thr Pro Leu Gln Ser Pro Ala Gln Val Leu Pro Asn Ser Ser
1580                1585                1590                1595

AAA GAC TCT TCT CAG CCA TCA TGT GTG GAG CAA AGC ACC AGC TCA GAT     4910
Lys Asp Ser Ser Gln Pro Ser Cys Val Glu Gln Ser Thr Ser Ser Asp
                1600                1605                1610

GAA AAT GAA ATG TCA GAC AAA AGC AAA AAA CAG TGC AAG TCC CCA TCC     4958
Glu Asn Glu Met Ser Asp Lys Ser Lys Lys Gln Cys Lys Ser Pro Ser
        1615                1620                1625

AGA AGA GAC AGT TAC AGT GAC AGC AGT GGG AGT GGA GAA GAT GAC TTA     5006
Arg Arg Asp Ser Tyr Ser Asp Ser Ser Gly Ser Gly Glu Asp Asp Leu
    1630                1635                1640

GTC ACA GCT CCA GCA AAC ATA TCA AAT TCG ACC TGG AGT TCA GCT TTG     5054
Val Thr Ala Pro Ala Asn Ile Ser Asn Ser Thr Trp Ser Ser Ala Leu
1645                1650                1655

CAT CAG ACT CTA AGC AAC ATG GTA TCA CAG GCA CAG AGT CAT CAT GAA     5102
```

|     |     |     |     |     |     |     |     |     |     |     |     |     |     |     |      |
|---|---|---|---|---|---|---|---|---|---|---|---|---|---|---|---|
| His | Gln | Thr | Leu | Ser | Asn | Met | Val | Ser | Gln | Ala | Gln | Ser | His | His | Glu |
| 1660 |     |     |     |     | 1665 |     |     |     | 1670 |     |     |     | 1675 |     |     |

| GCA | CCC | AAG | AGT | CAA | GAA | GAT | ACC | ATT | TGT | ACC | ATG | TTT | TAC | TAT | CCT | 5150 |
|---|---|---|---|---|---|---|---|---|---|---|---|---|---|---|---|---|
| Ala | Pro | Lys | Ser | Gln | Glu | Asp | Thr | Ile | Cys | Thr | Met | Phe | Tyr | Tyr | Pro | |
|     |     |     | 1680 |     |     |     | 1685 |     |     |     | 1690 |     |     |     |     | |

| CAG | AAA | ATT | CCC | AAT | AAA | CCA | GAG | TTT | GAG | GAC | AGT | AAT | CCT | TCC | CCT | 5198 |
|---|---|---|---|---|---|---|---|---|---|---|---|---|---|---|---|---|
| Gln | Lys | Ile | Pro | Asn | Lys | Pro | Glu | Phe | Glu | Asp | Ser | Asn | Pro | Ser | Pro | |
| 1695 |     |     |     |     | 1700 |     |     |     | 1705 |     |     |     |     |     |     | |

| CTA | CCA | CCG | GAT | ATG | GCT | CCT | GGG | CAG | AGT | TAT | CAA | CCC | CAA | TCA | GAA | 5246 |
|---|---|---|---|---|---|---|---|---|---|---|---|---|---|---|---|---|
| Leu | Pro | Pro | Asp | Met | Ala | Pro | Gly | Gln | Ser | Tyr | Gln | Pro | Gln | Ser | Glu | |
| 1710 |     |     |     |     | 1715 |     |     |     | 1720 |     |     |     |     |     |     | |

| TCT | GCT | TCC | TCT | AGT | TCG | ATG | GAT | AAG | TAT | CAT | ATA | CAT | CAC | ATT | TCT | 5294 |
|---|---|---|---|---|---|---|---|---|---|---|---|---|---|---|---|---|
| Ser | Ala | Ser | Ser | Ser | Ser | Met | Asp | Lys | Tyr | His | Ile | His | His | Ile | Ser | |
|     | 1725 |     |     |     |     | 1730 |     |     |     | 1735 |     |     |     |     |     | |

| GAA | CCA | ACT | AGA | CAA | GAA | AAC | TGG | ACA | CCT | TTG | AAA | AAT | GAC | TTG | GAA | 5342 |
|---|---|---|---|---|---|---|---|---|---|---|---|---|---|---|---|---|
| Glu | Pro | Thr | Arg | Gln | Glu | Asn | Trp | Thr | Pro | Leu | Lys | Asn | Asp | Leu | Glu | |
| 1740 |     |     |     |     | 1745 |     |     |     | 1750 |     |     |     |     |     | 1755 | |

| AAT | CAC | CTT | GAA | GAC | TTT | GAA | CTG | GAA | GTA | GAA | CTC | CTC | ATT | ACC | CTA | 5390 |
|---|---|---|---|---|---|---|---|---|---|---|---|---|---|---|---|---|
| Asn | His | Leu | Glu | Asp | Phe | Glu | Leu | Glu | Val | Glu | Leu | Leu | Ile | Thr | Leu | |
|     |     |     |     |     | 1760 |     |     |     | 1765 |     |     |     | 1770 |     |     | |

| ATT | AAA | TCA | GAA | AAA | GCA | AGC | CTG | GGT | TTT | ACA | GTA | ACC | AAA | GGC | AAT | 5438 |
|---|---|---|---|---|---|---|---|---|---|---|---|---|---|---|---|---|
| Ile | Lys | Ser | Glu | Lys | Ala | Ser | Leu | Gly | Phe | Thr | Val | Thr | Lys | Gly | Asn | |
|     |     |     | 1775 |     |     |     | 1780 |     |     |     | 1785 |     |     |     |     | |

| CAG | AGA | ATT | GGT | TGT | TAT | GTT | CAT | GAT | GTC | ATA | CAG | GAT | CCA | GCC | AAA | 5486 |
|---|---|---|---|---|---|---|---|---|---|---|---|---|---|---|---|---|
| Gln | Arg | Ile | Gly | Cys | Tyr | Val | His | Asp | Val | Ile | Gln | Asp | Pro | Ala | Lys | |
|     | 1790 |     |     |     |     | 1795 |     |     |     | 1800 |     |     |     |     |     | |

| AGT | GAT | GGA | AGG | CTA | AAA | CCT | GGG | GAC | CGG | CTC | ATA | AAG | GTT | AAT | GAT | 5534 |
|---|---|---|---|---|---|---|---|---|---|---|---|---|---|---|---|---|
| Ser | Asp | Gly | Arg | Leu | Lys | Pro | Gly | Asp | Arg | Leu | Ile | Lys | Val | Asn | Asp | |
|     | 1805 |     |     |     |     | 1810 |     |     |     | 1815 |     |     |     |     |     | |

| ACA | GAT | GTT | ACT | AAT | ATG | ACT | CAT | ACA | GAT | GCA | GTT | AAT | CTG | CTC | CGG | 5582 |
|---|---|---|---|---|---|---|---|---|---|---|---|---|---|---|---|---|
| Thr | Asp | Val | Thr | Asn | Met | Thr | His | Thr | Asp | Ala | Val | Asn | Leu | Leu | Arg | |
| 1820 |     |     |     |     | 1825 |     |     |     | 1830 |     |     |     |     |     | 1835 | |

| GCT | GCA | TCC | AAA | ACA | GTC | AGA | TTA | GTT | ATT | GGA | CGA | GTT | CCT | AGA | ATT | 5630 |
|---|---|---|---|---|---|---|---|---|---|---|---|---|---|---|---|---|
| Ala | Ala | Ser | Lys | Thr | Val | Arg | Leu | Val | Ile | Gly | Arg | Val | Pro | Arg | Ile | |
|     |     |     |     | 1840 |     |     |     |     | 1845 |     |     |     | 1850 |     |     | |

| ACC | CAG | AAT | ACC | AAT | GTT | GCC | TCA | TTT | GCT | ACC | GGA | CAT | AAA | CTA | ACG | 5678 |
|---|---|---|---|---|---|---|---|---|---|---|---|---|---|---|---|---|
| Thr | Gln | Asn | Thr | Asn | Val | Ala | Ser | Phe | Ala | Thr | Gly | His | Lys | Leu | Thr | |
|     |     |     | 1855 |     |     |     |     | 1860 |     |     |     | 1865 |     |     |     | |

| TGC | AAC | AAA | GAG | GAG | TTG | GGT | TTT | TCC | TTA | TGT | GGA | GGT | CAT | GAC | AGC | 5726 |
|---|---|---|---|---|---|---|---|---|---|---|---|---|---|---|---|---|
| Cys | Asn | Lys | Glu | Glu | Leu | Gly | Phe | Ser | Leu | Cys | Gly | Gly | His | Asp | Ser | |
|     |     | 1870 |     |     |     |     | 1875 |     |     |     | 1880 |     |     |     |     | |

| CTT | TAT | CAA | GTG | GTA | TAT | ATT | AGT | GAT | ATT | AAT | CCA | AGG | TCC | GTC | GCA | 5774 |
|---|---|---|---|---|---|---|---|---|---|---|---|---|---|---|---|---|
| Leu | Tyr | Gln | Val | Val | Tyr | Ile | Ser | Asp | Ile | Asn | Pro | Arg | Ser | Val | Ala | |
|     | 1885 |     |     |     |     | 1890 |     |     |     | 1895 |     |     |     |     |     | |

| GCC | ATT | GAG | GGT | AAT | CTC | CAG | CTA | TTA | GAT | GTC | ATC | CAT | TAT | GTG | AAC | 5822 |
|---|---|---|---|---|---|---|---|---|---|---|---|---|---|---|---|---|
| Ala | Ile | Glu | Gly | Asn | Leu | Gln | Leu | Leu | Asp | Val | Ile | His | Tyr | Val | Asn | |
| 1900 |     |     |     |     | 1905 |     |     |     | 1910 |     |     |     |     |     | 1915 | |

| GGA | GTC | AGC | ACA | CAA | GGA | ATG | ACC | TTG | GAG | GAA | GTT | AAC | AGA | GCA | TTA | 5870 |
|---|---|---|---|---|---|---|---|---|---|---|---|---|---|---|---|---|
| Gly | Val | Ser | Thr | Gln | Gly | Met | Thr | Leu | Glu | Glu | Val | Asn | Arg | Ala | Leu | |
|     |     |     |     |     | 1920 |     |     |     | 1925 |     |     |     | 1930 |     |     | |

| GAC | ATG | TCA | CTT | CCT | TCA | TTG | GTA | TTG | AAA | GCA | ACA | AGA | AAT | GAT | CTT | 5918 |
|---|---|---|---|---|---|---|---|---|---|---|---|---|---|---|---|---|
| Asp | Met | Ser | Leu | Pro | Ser | Leu | Val | Leu | Lys | Ala | Thr | Arg | Asn | Asp | Leu | |
|     |     |     | 1935 |     |     |     |     | 1940 |     |     |     | 1945 |     |     |     | |

| CCA | GTG | GTT | CCC | AGC | TCA | AAG | AGG | TCT | GCT | GTT | TCA | GCT | CCA | AAG | TCA | 5966 |
|---|---|---|---|---|---|---|---|---|---|---|---|---|---|---|---|---|
| Pro | Val | Val | Pro | Ser | Ser | Lys | Arg | Ser | Ala | Val | Ser | Ala | Pro | Lys | Ser | |
|     |     | 1950 |     |     |     |     | 1955 |     |     |     | 1960 |     |     |     |     | |

| ACC | AAA | GGC | AAT | GGT | TCC | TAC | AGT | GTG | GGG | TCT | TGC | AGC | CAG | CCT | GCC | 6014 |
|---|---|---|---|---|---|---|---|---|---|---|---|---|---|---|---|---|
| Thr | Lys | Gly | Asn | Gly | Ser | Tyr | Ser | Val | Gly | Ser | Cys | Ser | Gln | Pro | Ala | |
|     |     | 1965 |     |     |     | 1970 |     |     |     | 1975 |     |     |     |     |     | |

| CTC | ACT | CCT | AAT | GAT | TCA | TTC | TCC | ACG | GTT | GCT | GGG | GAA | GAA | ATA | AAT | 6062 |

```
Leu  Thr  Pro  Asn  Asp  Ser  Phe  Ser  Thr  Val  Ala  Gly  Glu  Glu  Ile  Asn
1980                1985                     1990                          1995

GAA  ATA  TCG  TAC  CCC  AAA  GGA  AAA  TGT  TCT  ACT  TAT  CAG  ATA  AAG  GGA        6110
Glu  Ile  Ser  Tyr  Pro  Lys  Gly  Lys  Cys  Ser  Thr  Tyr  Gln  Ile  Lys  Gly
                    2000                     2005                          2010

TCA  CCA  AAC  TTG  ACT  CTG  CCC  AAA  GAA  TCT  TAT  ATA  CAA  GAA  GAT  GAC        6158
Ser  Pro  Asn  Leu  Thr  Leu  Pro  Lys  Glu  Ser  Tyr  Ile  Gln  Glu  Asp  Asp
               2015                     2020                     2025

ATT  TAT  GAT  GAT  TCC  CAA  GAA  GCT  GAA  GTT  ATC  CAG  TCT  CTG  CTG  GAT        6206
Ile  Tyr  Asp  Asp  Ser  Gln  Glu  Ala  Glu  Val  Ile  Gln  Ser  Leu  Leu  Asp
               2030                     2035                     2040

GTT  GTT  GAT  GAG  GAA  GCC  CAG  AAT  CTT  TTA  AAC  GAA  AAT  AAT  GCA  GCA        6254
Val  Val  Asp  Glu  Glu  Ala  Gln  Asn  Leu  Leu  Asn  Glu  Asn  Asn  Ala  Ala
               2045                     2050                     2055

GGA  GAC  TCC  TGT  GGT  CCA  GGT  ACA  TTA  AAG  ATG  AAT  GGG  AAG  TTA  TCA        6302
Gly  Asp  Ser  Cys  Gly  Pro  Gly  Thr  Leu  Lys  Met  Asn  Gly  Lys  Leu  Ser
2060                2065                     2070                          2075

GAA  GAG  AGA  ACA  GAA  GAT  ACA  GAC  TGC  GAT  GGT  TCA  CCT  TTA  CCT  GAG        6350
Glu  Glu  Arg  Thr  Glu  Asp  Thr  Asp  Cys  Asp  Gly  Ser  Pro  Leu  Pro  Glu
                    2080                     2085                          2090

TAT  TTT  ACT  GAG  GCC  ACC  AAA  ATG  AAT  GGC  TGT  GAA  GAA  TAT  TGT  GAA        6398
Tyr  Phe  Thr  Glu  Ala  Thr  Lys  Met  Asn  Gly  Cys  Glu  Glu  Tyr  Cys  Glu
               2095                     2100                     2105

GAA  AAA  GTA  AAA  AGT  GAA  AGC  TTA  ATT  CAG  AAG  CCA  CAA  GAA  AAG  AAG        6446
Glu  Lys  Val  Lys  Ser  Glu  Ser  Leu  Ile  Gln  Lys  Pro  Gln  Glu  Lys  Lys
               2110                     2115                     2120

ACT  GAT  GAT  GAT  GAA  ATA  ACA  TGG  GGA  AAT  GAT  GAG  TTG  CCA  ATA  GAG        6494
Thr  Asp  Asp  Asp  Glu  Ile  Thr  Trp  Gly  Asn  Asp  Glu  Leu  Pro  Ile  Glu
               2125                     2130                     2135

AGA  ACA  AAC  CAT  GAA  GAT  TCT  GAT  AAA  GAT  CAT  TCC  TTT  CTG  ACA  AAC        6542
Arg  Thr  Asn  His  Glu  Asp  Ser  Asp  Lys  Asp  His  Ser  Phe  Leu  Thr  Asn
2140                2145                     2150                          2155

GAT  GAG  CTC  GCT  GTA  CTC  CCT  GTC  GTC  AAA  GTG  CTT  CCC  TCT  GGT  AAA        6590
Asp  Glu  Leu  Ala  Val  Leu  Pro  Val  Val  Lys  Val  Leu  Pro  Ser  Gly  Lys
               2160                     2165                     2170

TAC  ACG  GGT  GCC  AAC  TTA  AAA  TCA  GTC  ATT  CGA  GTC  CTG  CGG  GGT  TTG        6638
Tyr  Thr  Gly  Ala  Asn  Leu  Lys  Ser  Val  Ile  Arg  Val  Leu  Arg  Gly  Leu
               2175                     2180                     2185

CTA  GAT  CAA  GGA  ATT  CCT  TCT  AAG  GAG  CTG  GAG  AAT  CTT  CAA  GAA  TTA        6686
Leu  Asp  Gln  Gly  Ile  Pro  Ser  Lys  Glu  Leu  Glu  Asn  Leu  Gln  Glu  Leu
               2190                     2195                     2200

AAA  CCT  TTG  GAT  CAG  TGT  CTA  ATT  GGG  CAA  ACT  AAG  GAA  AAC  AGA  AGG        6734
Lys  Pro  Leu  Asp  Gln  Cys  Leu  Ile  Gly  Gln  Thr  Lys  Glu  Asn  Arg  Arg
2205                     2210                     2215

AAG  AAC  AGA  TAT  AAA  AAT  ATA  CTT  CCC  TAT  GAT  GCT  ACA  AGA  GTG  CCT        6782
Lys  Asn  Arg  Tyr  Lys  Asn  Ile  Leu  Pro  Tyr  Asp  Ala  Thr  Arg  Val  Pro
2220                     2225                     2230                     2235

CTT  GGA  GAT  GAA  GGT  GGC  TAT  ATC  AAT  GCC  AGC  TTC  ATT  AAG  ATA  CCA        6830
Leu  Gly  Asp  Glu  Gly  Gly  Tyr  Ile  Asn  Ala  Ser  Phe  Ile  Lys  Ile  Pro
                    2240                     2245                          2250

GTT  GGG  AAA  GAA  GAG  TTC  GTT  TAC  ATT  GCC  TGC  CAA  GGA  CCA  CTG  CCT        6878
Val  Gly  Lys  Glu  Glu  Phe  Val  Tyr  Ile  Ala  Cys  Gln  Gly  Pro  Leu  Pro
                    2255                     2260                          2265

ACA  ACT  GTT  GGA  GAC  TTC  TGG  CAG  ATG  ATT  TGG  GAG  CAA  AAA  TCC  ACA        6926
Thr  Thr  Val  Gly  Asp  Phe  Trp  Gln  Met  Ile  Trp  Glu  Gln  Lys  Ser  Thr
               2270                     2275                     2280

GTG  ATA  GCC  ATG  ATG  ACT  CAA  GAA  GTA  GAA  GGA  GAA  AAA  ATC  AAA  TGC        6974
Val  Ile  Ala  Met  Met  Thr  Gln  Glu  Val  Glu  Gly  Glu  Lys  Ile  Lys  Cys
               2285                     2290                     2295

CAG  CGC  TAT  TGG  CCC  AAC  ATC  CTA  GGC  AAA  ACA  ACA  ATG  GTC  AGC  AAC        7022
```

| | | | | | | | | | | | | | | | | |
|---|---|---|---|---|---|---|---|---|---|---|---|---|---|---|---|---|
| Gln | Arg | Tyr | Trp | Pro | Asn | Ile | Leu | Gly | Lys | Thr | Thr | Met | Val | Ser | Asn | |
| 2300 | | | | | 2305 | | | | 2310 | | | | | | 2315 | |

| AGA | CTT | CGA | CTG | GCT | CTT | GTG | AGA | ATG | CAG | CAG | CTG | AAG | GGC | TTT | GTG | 7070 |
|---|---|---|---|---|---|---|---|---|---|---|---|---|---|---|---|---|
| Arg | Leu | Arg | Leu | Ala | Leu | Val | Arg | Met | Gln | Gln | Leu | Lys | Gly | Phe | Val | |
| | | | | 2320 | | | | | 2325 | | | | | | 2330 | |

| GTG | AGG | GCA | ATG | ACC | CTT | GAA | GAT | ATT | CAG | ACC | AGA | GAG | GTG | CGC | CAT | 7118 |
|---|---|---|---|---|---|---|---|---|---|---|---|---|---|---|---|---|
| Val | Arg | Ala | Met | Thr | Leu | Glu | Asp | Ile | Gln | Thr | Arg | Glu | Val | Arg | His | |
| | | | | 2335 | | | | | 2340 | | | | | | 2345 | |

| ATT | TCT | CAT | CTG | AAT | TTC | ACT | GCC | TGG | CCA | GAC | CAT | GAT | ACA | CCT | TCT | 7166 |
|---|---|---|---|---|---|---|---|---|---|---|---|---|---|---|---|---|
| Ile | Ser | His | Leu | Asn | Phe | Thr | Ala | Trp | Pro | Asp | His | Asp | Thr | Pro | Ser | |
| | | | 2350 | | | | | 2355 | | | | | 2360 | | | |

| CAA | CCA | GAT | GAT | CTG | CTT | ACT | TTT | ATC | TCC | TAC | ATG | AGA | CAC | ATC | CAC | 7214 |
|---|---|---|---|---|---|---|---|---|---|---|---|---|---|---|---|---|
| Gln | Pro | Asp | Asp | Leu | Leu | Thr | Phe | Ile | Ser | Tyr | Met | Arg | His | Ile | His | |
| | | 2365 | | | | | 2370 | | | | | 2375 | | | | |

| AGA | TCA | GGC | CCA | ATC | ATT | ACG | CAC | TGC | AGT | GCT | GGC | ATT | GGA | CGT | TCA | 7262 |
|---|---|---|---|---|---|---|---|---|---|---|---|---|---|---|---|---|
| Arg | Ser | Gly | Pro | Ile | Ile | Thr | His | Cys | Ser | Ala | Gly | Ile | Gly | Arg | Ser | |
| 2380 | | | | | 2385 | | | | 2390 | | | | | | 2395 | |

| GGG | ACC | CTG | ATT | TGC | ATA | GAT | GTG | GTT | CTG | GGA | TTA | ATC | AGT | CAG | GAT | 7310 |
|---|---|---|---|---|---|---|---|---|---|---|---|---|---|---|---|---|
| Gly | Thr | Leu | Ile | Cys | Ile | Asp | Val | Val | Leu | Gly | Leu | Ile | Ser | Gln | Asp | |
| | | | | 2400 | | | | | 2405 | | | | | | 2410 | |

| CTT | GAT | TTT | GAC | ATC | TCT | GAT | TTG | GTG | CGC | TGC | ATG | AGA | CTA | CAA | AGA | 7358 |
|---|---|---|---|---|---|---|---|---|---|---|---|---|---|---|---|---|
| Leu | Asp | Phe | Asp | Ile | Ser | Asp | Leu | Val | Arg | Cys | Met | Arg | Leu | Gln | Arg | |
| | | | 2415 | | | | | 2420 | | | | | 2425 | | | |

| CAC | GGA | ATG | GTT | CAG | ACA | GAG | GAT | CAA | TAT | ATT | TTC | TGC | TAT | CAA | GTC | 7406 |
|---|---|---|---|---|---|---|---|---|---|---|---|---|---|---|---|---|
| His | Gly | Met | Val | Gln | Thr | Glu | Asp | Gln | Tyr | Ile | Phe | Cys | Tyr | Gln | Val | |
| | | 2430 | | | | | 2435 | | | | | 2440 | | | | |

| ATC | CTT | TAT | GTC | CTG | ACA | CGT | CTT | CAA | GCA | GAA | GAA | GAG | CAA | AAA | CAG | 7454 |
|---|---|---|---|---|---|---|---|---|---|---|---|---|---|---|---|---|
| Ile | Leu | Tyr | Val | Leu | Thr | Arg | Leu | Gln | Ala | Glu | Glu | Glu | Gln | Lys | Gln | |
| | 2445 | | | | | 2450 | | | | | 2455 | | | | | |

| CAG | CCT | CAG | CTT | CTG | AAG | TGACATGAAA | AGAGCCTCTG | GATGCATTTC | 7502 |
|---|---|---|---|---|---|---|---|---|---|
| Gln | Pro | Gln | Leu | Leu | Lys | | | | |
| 2460 | | | | | 2465 | | | | |

| | | | | | |
|---|---|---|---|---|---|
| CATTTCTCTC | CTTAACCTCC | AGCAGACTCC | TGCTCTCTAT | CCAAATAAAG | ATCACAGAGC | 7562 |
| AGNAAGTTCA | TACAACATGC | ATGTTCTCCT | CTATCTTAGA | GGGGTATTCT | TCTTGAAAAT | 7622 |
| AAAAAATATT | GAAATGCTGT | ATTTTTACAG | CTACTTTAAC | CTATGATAAT | TATTTACAAA | 7682 |
| ATTTTAACAC | TAACCAAACA | ATGCAGATCT | TAGGGATGAT | TAAAGGCAGC | ATTGATGATA | 7742 |
| GCAAGACATT | GTTACAAGGA | CATGGTGAGT | CTATTTTTAA | TGCACCAATC | TTGTTTATAG | 7802 |
| CAAAAATGTT | TTCCAATATT | TTAATAAAGT | AGTTATTTTA | TAGGGCATAC | TTGAAACCAG | 7862 |
| TATTTAAGCT | TTAAATGACA | GTAATATTGG | CATAGAAAAA | AGTAGCAAAT | GTTACTGTA | 7922 |
| TCAATTTCTA | ATGTTTACTA | TATAGAATTT | CCTGTAATAT | ATTTATATAC | TTTTCATGA | 7982 |
| AAATGGAGTT | ATCAGTTATC | TGTTTGTTAC | TGCATCATCT | GTTTGTAATC | ATTATCTC | 8040 |

( 2 ) INFORMATION FOR SEQ ID NO:2:

( i ) SEQUENCE CHARACTERISTICS:
        ( A ) LENGTH: 3090 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: HOMO SAPIENS ( i x ) FEATURE:

(A) NAME/KEY: CDS
(B) LOCATION: 1311..2420

(xi) SEQUENCE DESCRIPTION: SEQ ID NO:2:

```
GAATTCCGGA TTTACCTCAG TCTGTATCCC TTGAATAGCT CACAATAATC GACACATGCA      60
GCTGGGGACT GTGGGTGGGA TACTTAGGTG TGGGACACCA TATCTTCCAG CAGTAATAAA     120
GAAGTCAGGT GGGAATATGT AACATCTTGA GTGCTCATCC AGGTAGGTAC TAAGGTATGA     180
TCAACTCTAT GGAAGATCGA TTAGGAAACT CCCTGAAAGA GAGTTCAGCC TGAAGAGAGA     240
ACCAAAGGCC AACATCTTGG AGCTGGCTAC AGGACAGTAG GATGTAAGCT CGAGGGGAGG     300
AGAGGGTTAG GCGCAGTGGC TCACGCCTGT AGTCCCAACC ATTTGGAGG CTGAGGCAGG      360
CAGATCGCTT GAGCCCGGGG GTTCAAGACC AGCCTGGGCA ACATGGCGAA ACCCCATCTC     420
TACAAAAAAA TACAAAAAAA ATGTAGCTGC GTGTGGTGGC ATGCACCTGT AGTCACAGCC     480
ACCACAGAGG TTGAGGTGGG AGGACTGCTT GAGCCTGGGA GGTGGAGGCT GCAGCGAACC     540
GAGATTGTGC CACTGCACTC CAGGATGGGC GACAGAGTGA GACCCGGACA GAGTGAGACC     600
CTGTCTCATT CATTCATTCA TAAATAAGAA GAGGGGAAA ACGGGTGCCC AGATTGCTCT      660
CAGGCTCCTC CTCCCTTTCA GCTGGTACTT AACCACTCTT AACTTCAGCC TGCTCATGAA     720
TGAAATGGGA ATGACAATTC CTAACTCAGG CAGTTTTTGC AAAGACCAGA GAAAATCATG     780
TATTAATACT AGTACCCAGC ACCATTCCAA ACATACAATA CAAATGCCCC ATAAATGACA     840
GCCAAGGTAA CTGTTCTTTG CTTCCTCTCT TAGGAGACGT GTGAGGTTCT CTGTTGCTCC     900
TTTTGACTCC CAACTCCTGC TACAATGACT GATTTGACAC TGATTACCTC ACAGTACACA     960
CTGGGTGCTG GCCAACTGCA GCATGCTACG TATCCCACAC CCCTCCCTG AGTGGTGGGA     1020
CATTAATGGT GGGATGGTAG AATGTGCAGT CCGGTCTTGT ACATTGAGTG TTAAACCTAC     1080
AATGTTTTGG ATGATAGAAG GGACATTCCA TCTTCTTACA AGCAGGGAAG TAACGGCAGA     1140
GCTGACTACT GGAAGGTGGT GCTGGTGGTG CAACAGGTTC TGGAGTTAAA ACCAATGGAA     1200
AAGAAAGATT TCAGCTTTCC TTAAGACAAG ACAAAGAGAA AAACCAGGAG ATCCACCTAT     1260
CGCCCATCAC ATTACAGCCA GCACTGTCCG AGGCAAAGAC AGTCCACAGC ATG GTC       1316
                                                       Met Val
                                                         1
CAA CCT GAG CAG GCC CCA AAG GTA CTG AAT GTT GTC GTG GAC CCT CAA      1364
Gln Pro Glu Gln Ala Pro Lys Val Leu Asn Val Val Val Asp Pro Gln
          5                  10                  15
GGC CGA GGT GCT CCT GAG ATC AAA GCT ACC ACC GCT ACC TCT GTT TGC      1412
Gly Arg Gly Ala Pro Glu Ile Lys Ala Thr Thr Ala Thr Ser Val Cys
 20                  25                  30
CCT TCT CCT TTC AAA ATG AAG CCC ATA GGA CTT CAA GAG AGA AGA GGG      1460
Pro Ser Pro Phe Lys Met Lys Pro Ile Gly Leu Gln Glu Arg Arg Gly
 35                  40                  45                  50
TCC AAC GTA TCT CTT ACA TTG GAC ATG AGT AGC TTG GGA AAC ATT GAA      1508
Ser Asn Val Ser Leu Thr Leu Asp Met Ser Ser Leu Gly Asn Ile Glu
                  55                  60                  65
CCC TTT GTG TCT ATA CCA ACA CCA CGG GAG AAG GTA GCA ATG GAG TAT      1556
Pro Phe Val Ser Ile Pro Thr Pro Arg Glu Lys Val Ala Met Glu Tyr
             70                  75                  80
CTG CAG TCA GCC AGC CGA ATT CTC GAC AAG GTT CAG CTG AGG GAC GTC      1604
Leu Gln Ser Ala Ser Arg Ile Leu Asp Lys Val Gln Leu Arg Asp Val
         85                  90                  95
GTG GCA AGT TCA CAT TTA CTC CAA AGT GAA TTC ATG GAA ATA CCA ATG      1652
Val Ala Ser Ser His Leu Leu Gln Ser Glu Phe Met Glu Ile Pro Met
100                 105                 110
AAC TTT GTG GAT CCC AAA GAA ATT GAT ATT CCG CGT CAT GGA ACT AAA      1700
```

```
Asn  Phe  Val  Asp  Pro  Lys  Glu  Ile  Asp  Ile  Pro  Arg  His  Gly  Thr  Lys
115            120                 125                      130

AAT  CGC  TAT  AAG  ACC  ATT  TTA  CCA  AAT  CCC  CTC  AGC  AGA  GTG  TGT  TTA   1748
Asn  Arg  Tyr  Lys  Thr  Ile  Leu  Pro  Asn  Pro  Leu  Ser  Arg  Val  Cys  Leu
               135                 140                      145

AGA  CCA  AAA  AAT  GTA  ACC  GAT  TCA  TTG  AGC  ACC  TAC  ATT  AAT  GCT  AAT   1796
Arg  Pro  Lys  Asn  Val  Thr  Asp  Ser  Leu  Ser  Thr  Tyr  Ile  Asn  Ala  Asn
               150                 155                      160

TAT  ATT  AGG  GGC  TAC  AGT  GGC  AAG  GAG  AAA  GCC  TTC  ATT  GCC  ACG  CAG   1844
Tyr  Ile  Arg  Gly  Tyr  Ser  Gly  Lys  Glu  Lys  Ala  Phe  Ile  Ala  Thr  Gln
          165                 170                      175

GGC  CCC  ATG  ATC  AAC  ACC  GTG  GAT  GAT  TTC  TGG  CAG  ATG  GTT  TGG  CAG   1892
Gly  Pro  Met  Ile  Asn  Thr  Val  Asp  Asp  Phe  Trp  Gln  Met  Val  Trp  Gln
     180                 185                      190

GAA  GAC  AGC  CCT  GTG  ATT  GTT  ATG  ATC  ACA  AAA  CTC  AAA  GAA  AAA  AAT   1940
Glu  Asp  Ser  Pro  Val  Ile  Val  Met  Ile  Thr  Lys  Leu  Lys  Glu  Lys  Asn
195                 200                      205                           210

GAG  AAA  TGT  GTG  CTA  TAC  TGG  CCG  GAA  AAG  AGA  GGG  ATA  TAT  GGA  AAA   1988
Glu  Lys  Cys  Val  Leu  Tyr  Trp  Pro  Glu  Lys  Arg  Gly  Ile  Tyr  Gly  Lys
                    215                      220                      225

GTT  GAG  GTT  CTG  GTT  ATC  AGT  GTA  AAT  GAA  TGT  GAT  AAC  TAC  ACC  ATT   2036
Val  Glu  Val  Leu  Val  Ile  Ser  Val  Asn  Glu  Cys  Asp  Asn  Tyr  Thr  Ile
               230                 235                      240

CGA  AAC  CTT  GTC  TTA  AAG  CAA  GGA  AGC  CAC  ACC  CAA  CAT  GTG  AGC  AAT   2084
Arg  Asn  Leu  Val  Leu  Lys  Gln  Gly  Ser  His  Thr  Gln  His  Val  Ser  Asn
          245                 250                      255

TAC  TGG  TAC  ACC  TCA  TGG  CCT  GAT  CAC  AAG  ACT  CCA  GAC  AGT  GCC  CAG   2132
Tyr  Trp  Tyr  Thr  Ser  Trp  Pro  Asp  His  Lys  Thr  Pro  Asp  Ser  Ala  Gln
     260                 265                      270

CCC  CTC  CTA  CAG  CTC  ATG  CTG  GAT  GTA  GAA  GAA  GAC  AGA  CTT  GCT  TCC   2180
Pro  Leu  Leu  Gln  Leu  Met  Leu  Asp  Val  Glu  Glu  Asp  Arg  Leu  Ala  Ser
275                 280                      285                           290

CAG  GGG  CCG  AGG  GCT  GTG  GTT  GTC  CAC  TGC  AGT  GCA  GGA  ATA  GGT  AGA   2228
Gln  Gly  Pro  Arg  Ala  Val  Val  Val  His  Cys  Ser  Ala  Gly  Ile  Gly  Arg
               295                 300                      305

ACA  GGG  TGT  TTT  ATT  GCT  ACA  TCC  ATT  GGC  TGT  CAA  CAG  CTG  AAA  GAA   2276
Thr  Gly  Cys  Phe  Ile  Ala  Thr  Ser  Ile  Gly  Cys  Gln  Gln  Leu  Lys  Glu
          310                 315                      320

GAA  GGA  GTT  GTG  GAT  GCA  CTA  AGC  ATT  GTC  TGC  CAG  CTT  CGT  ATG  GAT   2324
Glu  Gly  Val  Val  Asp  Ala  Leu  Ser  Ile  Val  Cys  Gln  Leu  Arg  Met  Asp
     325                 330                      335

AGA  GGT  GGA  ATG  GTG  CAA  ACC  AGT  GAG  CAG  TAT  GAA  TTT  GTG  CAC  CAT   2372
Arg  Gly  Gly  Met  Val  Gln  Thr  Ser  Glu  Gln  Tyr  Glu  Phe  Val  His  His
     340                 345                      350

GCT  CTG  TGC  CTG  TAT  GAG  AGC  AGA  CTT  TCA  GCA  GAG  ACT
Ala  Leu  Cys  Leu  Tyr  Glu  Ser  Arg  Leu  Ser  Ala  Glu  Thr
355                 360                      365

GTC  CAG  TGAGTCATTG    2427
                                                       Val  Gln
                                                            370

AAGACTTGTC  AGACCATCAA  TCTCTTGGGG  TGATTAACAA  ATTACCACC  CAAGGCTTCA   2487

TGAAGGAGCT  TCCTGCAATG  GAAGGAAGGA  GAAGCTCTGA  AGCCCATGTA  TGGCATGGAT   2547

TGTGGAAGAC  TGGGCAACAT  ATTTAAGATT  TCCAGCTCCT  TGTGTATATG  AATGCATTTG   2607

TAAGCATCCC  CCAAATTATT  CTGAAGGTTT  TTTGATGATG  GAGGTATGAT  AGGTTTATCA   2667

CACAGCCTAA  GGCAGATTTT  GTTTTGTCTG  TACTGACTCT  ATCTGCCACA  CAGAATGTAT   2727

GTATGTAATA  TTCAGTAATA  AATGTCATCA  GGTGATGACT  GGATGAGCTG  CTGAAGACAT   2787

TCGTATTATG  TGTTAGATGC  TTTAATGTTT  GCAAAATCTG  TCTTGTGAAT  GGACTGTCAG   2847
```

-continued

```
CTGTTAAACT GTTCCTGTTT TGAAGTGCTA TTACCTTTCT CAGTTACCAG AATCTTGCTG    2907

CTAAAGTTGC AAGTGATTGA TAATGGATTT TTAACAGAGA AGTCTTTGTT TTTGAAAAAC    2967

AAAAATCAAA AACAGTAACT ATTTTATATG GAAATGTGTC TTGATAATAT TACCTATTAA    3027

ATGTGTATTT ATAGTCCCTC CTATCAAACA ATTACAGAGC ACAATGATTG TCATCCGGAA    3087

TTC                                                                  3090
```

( 2 ) INFORMATION FOR SEQ ID NO:3:

( i ) SEQUENCE CHARACTERISTICS:
        ( A ) LENGTH: 2465 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met His Val Ser Leu Ala Glu Ala Leu Glu Val Arg Gly Gly Pro Leu
 1               5                  10                  15

Gln Glu Glu Glu Ile Trp Ala Val Leu Asn Gln Ser Ala Glu Ser Leu
                20                  25                  30

Gln Glu Leu Phe Arg Lys Val Ser Leu Ala Asp Pro Ala Ala Leu Gly
            35                  40                  45

Phe Ile Ile Ser Pro Trp Ser Leu Leu Leu Leu Pro Ser Gly Ser Val
 50                  55                  60

Ser Phe Thr Asp Glu Asn Ile Ser Asn Gln Asp Leu Arg Ala Phe Thr
 65                  70                  75                  80

Ala Pro Glu Val Leu Gln Asn Gln Ser Leu Thr Ser Leu Ser Asp Val
                85                  90                  95

Glu Lys Ile His Ile Tyr Ser Leu Gly Met Thr Leu Tyr Trp Gly Ala
            100                 105                 110

Asp Tyr Glu Val Pro Gln Ser Gln Pro Ile Lys Leu Gly Asp His Leu
            115                 120                 125

Asn Ser Ile Leu Leu Gly Met Cys Glu Asp Val Ile Tyr Ala Arg Val
            130                 135                 140

Ser Val Arg Thr Val Leu Asp Ala Cys Ser Ala His Ile Arg Asn Ser
145                 150                 155                 160

Asn Cys Ala Pro Ser Phe Ser Tyr Val Lys His Leu Val Lys Leu Val
                165                 170                 175

Leu Gly Asn Leu Ser Gly Thr Asp Gln Leu Ser Cys Asn Ser Glu Gln
            180                 185                 190

Lys Pro Asp Arg Ser Gln Ala Ile Arg Asp Arg Leu Arg Gly Lys Gly
            195                 200                 205

Leu Pro Thr Gly Arg Ser Ser Thr Ser Asp Val Leu Asp Ile Gln Lys
            210                 215                 220

Pro Pro Leu Ser His Gln Thr Phe Leu Asn Lys Gly Leu Ser Lys Ser
225                 230                 235                 240

Met Gly Phe Leu Ser Ile Lys Asp Thr Gln Asp Glu Asn Tyr Phe Lys
                245                 250                 255

Asp Ile Leu Ser Asp Asn Ser Gly Arg Glu Asp Ser Glu Asn Thr Phe
            260                 265                 270

Cys Pro Tyr Gln Phe Lys Thr Ser Gly Pro Glu Lys Lys Pro Ile Pro
            275                 280                 285

Gly Ile Asp Val Leu Ser Lys Lys Ile Trp Ala Ser Ser Met Asp
            290                 295                 300
```

```
Leu  Leu  Cys  Thr  Ala  Asp  Arg  Asp  Phe  Ser  Ser  Gly  Glu  Thr  Ala  Thr
305                      310                      315                      320

Tyr  Arg  Arg  Cys  His  Pro  Glu  Ala  Val  Thr  Val  Arg  Thr  Ser  Thr  Thr
                         325                      330                      335

Pro  Arg  Lys  Lys  Glu  Ala  Arg  Tyr  Ser  Asp  Gly  Ser  Ile  Ala  Leu  Asp
               340                      345                      350

Ile  Phe  Gly  Pro  Gln  Lys  Met  Asp  Pro  Ile  Tyr  His  Thr  Arg  Glu  Leu
          355                      360                      365

Pro  Thr  Ser  Ser  Ala  Ile  Ser  Ser  Ala  Leu  Asp  Arg  Ile  Arg  Glu  Arg
     370                      375                      380

Gln  Lys  Lys  Leu  Gln  Val  Leu  Arg  Glu  Ala  Met  Asn  Val  Glu  Glu  Pro
385                      390                      395                      400

Val  Arg  Arg  Tyr  Lys  Thr  Tyr  His  Gly  Asp  Val  Phe  Ser  Thr  Ser  Ser
                    405                      410                      415

Glu  Ser  Pro  Ser  Ile  Ile  Ser  Ser  Glu  Ser  Asp  Phe  Arg  Gln  Val  Arg
                    420                      425                      430

Arg  Ser  Glu  Ala  Ser  Lys  Arg  Phe  Glu  Ser  Ser  Ser  Gly  Leu  Pro  Gly
               435                      440                      445

Val  Asp  Glu  Thr  Leu  Ser  Gln  Gly  Gln  Ser  Gln  Arg  Pro  Ser  Arg  Gln
     450                      455                      460

Tyr  Glu  Thr  Pro  Phe  Glu  Gly  Asn  Leu  Ile  Asn  Gln  Glu  Ile  Met  Leu
465                      470                      475                      480

Lys  Arg  Gln  Glu  Glu  Glu  Leu  Met  Gln  Leu  Gln  Ala  Lys  Met  Ala  Leu
                    485                      490                      495

Arg  Gln  Ser  Arg  Leu  Ser  Leu  Tyr  Pro  Gly  Asp  Thr  Ile  Lys  Ala  Ser
               500                      505                      510

Met  Leu  Asp  Ile  Thr  Arg  Asp  Pro  Leu  Arg  Glu  Ile  Ala  Leu  Glu  Thr
          515                      520                      525

Ala  Met  Thr  Gln  Arg  Lys  Leu  Arg  Asn  Phe  Phe  Gly  Pro  Glu  Phe  Val
     530                      535                      540

Lys  Met  Thr  Ile  Glu  Pro  Phe  Ile  Ser  Leu  Asp  Leu  Pro  Arg  Ser  Ile
545                      550                      555                      560

Leu  Thr  Lys  Lys  Gly  Lys  Asn  Glu  Asp  Asn  Arg  Arg  Lys  Val  Asn  Ile
                    565                      570                      575

Met  Leu  Leu  Asn  Gly  Gln  Arg  Leu  Glu  Leu  Thr  Cys  Asp  Thr  Lys  Thr
               580                      585                      590

Ile  Cys  Lys  Asp  Val  Phe  Asp  Met  Val  Val  Ala  His  Ile  Gly  Leu  Val
          595                      600                      605

Glu  His  His  Leu  Phe  Ala  Leu  Ala  Thr  Leu  Lys  Asp  Asn  Glu  Tyr  Phe
     610                      615                      620

Phe  Val  Asp  Pro  Asp  Leu  Lys  Leu  Thr  Lys  Val  Ala  Pro  Glu  Gly  Trp
625                      630                      635                      640

Lys  Glu  Glu  Pro  Lys  Lys  Lys  Thr  Lys  Ala  Thr  Val  Asn  Phe  Thr  Leu
                    645                      650                      655

Phe  Phe  Arg  Ile  Lys  Phe  Phe  Met  Asp  Asp  Val  Ser  Leu  Ile  Gln  His
               660                      665                      670

Thr  Leu  Thr  Cys  His  Gln  Tyr  Tyr  Leu  Gln  Leu  Arg  Lys  Asp  Ile  Leu
          675                      680                      685

Glu  Glu  Arg  Met  His  Cys  Asp  Asp  Glu  Thr  Ser  Leu  Leu  Leu  Ala  Ser
     690                      695                      700

Leu  Ala  Leu  Gln  Ala  Glu  Tyr  Gly  Asp  Tyr  Gln  Pro  Glu  Val  His  Gly
705                      710                      715                      720

Val  Ser  Tyr  Phe  Arg  Met  Glu  His  Tyr  Leu  Pro  Ala  Arg  Val  Met  Glu
                    725                      730                      735
```

| | | | | | | | | | | | | | |
|---|---|---|---|---|---|---|---|---|---|---|---|---|---|
|Lys|Leu|Asp|Leu|Ser|Tyr|Ile|Lys|Glu|Glu|Leu|Pro|Lys|Leu|His|Asn|
| | | |740| | | |745| | | |750| | |
|Thr|Tyr|Val|Gly|Ala|Ser|Glu|Lys|Glu|Thr|Glu|Leu|Glu|Phe|Leu|Lys|
| | | |755| | | |760| | | |765| | |
|Val|Cys|Gln|Arg|Leu|Thr|Glu|Tyr|Gly|Val|His|Phe|His|Arg|Val|His|
| | |770| | | |775| | | |780| | | |
|Pro|Glu|Lys|Lys|Ser|Gln|Thr|Gly|Ile|Leu|Leu|Gly|Val|Cys|Ser|Lys|
|785| | | |790| | | |795| | | | | |800|
|Gly|Val|Leu|Val|Phe|Glu|Val|His|Asn|Gly|Val|Arg|Thr|Leu|Val|Leu|
| | | | |805| | | |810| | | | |815| |
|Arg|Phe|Pro|Trp|Arg|Glu|Thr|Lys|Lys|Ile|Ser|Phe|Ser|Lys|Lys|Lys|
| | | |820| | | |825| | | | |830| | |
|Ile|Thr|Leu|Gln|Asn|Thr|Ser|Asp|Gly|Ile|Lys|His|Gly|Phe|Gln|Thr|
| | | |835| | | |840| | | | |845| | |
|Asp|Asn|Ser|Lys|Ile|Cys|Gln|Tyr|Leu|Leu|His|Leu|Cys|Ser|Tyr|Gln|
| |850| | | | |855| | | | |860| | | |
|His|Lys|Phe|Gln|Leu|Gln|Met|Arg|Ala|Arg|Gln|Ser|Asn|Gln|Asp|Ala|
|865| | | | |870| | | | |875| | | | |880|
|Gln|Asp|Ile|Glu|Arg|Ala|Ser|Phe|Arg|Ser|Leu|Asn|Leu|Gln|Ala|Glu|
| | | | |885| | | | |890| | | | |895| |
|Ser|Val|Arg|Gly|Phe|Asn|Met|Gly|Arg|Ala|Ile|Ser|Thr|Gly|Ser|Leu|
| | | |900| | | | |905| | | | |910| | |
|Ala|Ser|Ser|Thr|Leu|Asn|Lys|Leu|Ala|Val|Arg|Pro|Leu|Ser|Val|Gln|
| | |915| | | | |920| | | | |925| | | |
|Ala|Glu|Ile|Leu|Lys|Arg|Leu|Ser|Cys|Ser|Glu|Leu|Ser|Leu|Tyr|Gln|
| | |930| | | | |935| | | | |940| | | |
|Pro|Leu|Gln|Asn|Ser|Ser|Lys|Glu|Lys|Asn|Asp|Lys|Ala|Ser|Trp|Glu|
|945| | | | |950| | | | |955| | | | |960|
|Glu|Lys|Pro|Arg|Glu|Met|Ser|Lys|Ser|Tyr|His|Asp|Leu|Ser|Gln|Ala|
| | | | |965| | | | |970| | | | |975| |
|Ser|Leu|Tyr|Pro|His|Arg|Lys|Asn|Val|Ile|Val|Asn|Met|Glu|Pro|Pro|
| | | |980| | | | |985| | | | |990| | |
|Pro|Gln|Thr|Val|Ala|Glu|Leu|Val|Gly|Lys|Pro|Ser|His|Gln|Met|Ser|
| | |995| | | | |1000| | | | |1005| | | |
|Arg|Ser|Asp|Ala|Glu|Ser|Leu|Ala|Gly|Val|Thr|Lys|Leu|Asn|Asn|Ser|
| |1010| | | | |1015| | | | |1020| | | | |
|Lys|Ser|Val|Ala|Ser|Leu|Asn|Arg|Ser|Pro|Glu|Arg|Arg|Lys|His|Glu|
|1025| | | | |1030| | | | |1035| | | | |1040|
|Ser|Asp|Ser|Ser|Ser|Ile|Glu|Asp|Pro|Gly|Gln|Ala|Tyr|Val|Leu|Asp|
| | | | |1045| | | | |1050| | | | |1055| |
|Val|Leu|His|Lys|Arg|Trp|Ser|Ile|Val|Ser|Ser|Pro|Glu|Arg|Glu|Ile|
| | | |1060| | | | |1065| | | | |1070| | |
|Thr|Leu|Val|Asn|Leu|Lys|Lys|Asp|Ala|Lys|Tyr|Gly|Leu|Gly|Phe|Gln|
| | |1075| | | | |1080| | | | |1085| | | |
|Ile|Ile|Gly|Gly|Glu|Lys|Met|Glu|Thr|Asp|Leu|Gly|Ile|Phe|Ile|Ser|
| |1090| | | | |1095| | | | |1100| | | | |
|Ser|Val|Ala|Pro|Gly|Gly|Pro|Ala|Asp|Phe|His|Gly|Cys|Leu|Lys|Pro|
|1105| | | | |1110| | | | |1115| | | | |1120|
|Gly|Asp|Arg|Leu|Ile|Ser|Val|Asn|Ser|Val|Ser|Leu|Glu|Gly|Val|Ser|
| | | | |1125| | | | |1130| | | | |1135| |
|His|His|Ala|Ala|Ile|Glu|Ile|Leu|Gln|Asn|Ala|Pro|Glu|Asp|Val|Thr|
| | | | |1140| | | | |1145| | | | |1150| |
|Leu|Val|Ile|Ser|Gln|Pro|Lys|Glu|Lys|Ile|Ser|Lys|Val|Pro|Ser|Thr|

|     |     |     |     |     | 1155 |     |     |     |     | 1160 |     |     |     |     | 1165 |
| --- | --- | --- | --- | --- | --- | --- | --- | --- | --- | --- | --- | --- | --- | --- | --- |

Pro Val His Leu Thr Asn Glu Met Lys Asn Tyr Met Lys Lys Ser Ser
                    1170                1175                    1180

Tyr Met Gln Asp Ser Ala Ile Asp Ser Ser Lys Asp His His Trp
1185                1190                1195                    1200

Ser Arg Gly Thr Leu Arg His Ile Ser Glu Asn Ser Phe Gly Pro Ser
                    1205                1210                    1215

Gly Gly Leu Arg Glu Gly Ser Leu Ser Ser Gln Asp Ser Arg Thr Glu
                    1220                1225                    1230

Ser Ala Ser Leu Ser Gln Ser Gln Val Asn Gly Phe Phe Ala Ser His
                    1235                1240                    1245

Leu Gly Asp Gln Thr Trp Gln Glu Ser Gln His Gly Ser Pro Ser Pro
                    1250                1255                    1260

Ser Val Ile Ser Lys Ala Thr Glu Lys Glu Thr Phe Thr Asp Ser Asn
1265                1270                1275                    1280

Gln Ser Lys Thr Lys Lys Pro Gly Ile Ser Asp Val Thr Asp Tyr Ser
                    1285                1290                    1295

Asp Arg Gly Asp Ser Asp Met Asp Glu Ala Thr Tyr Ser Ser Ser Gln
                    1300                1305                    1310

Asp His Gln Thr Pro Lys Gln Glu Ser Ser Ser Val Asn Thr Ser
                    1315                1320                    1325

Asn Lys Met Asn Phe Lys Thr Phe Ser Ser Ser Pro Pro Lys Pro Gly
                    1330                1335                    1340

Asp Ile Phe Glu Val Glu Leu Ala Lys Asn Asp Asn Ser Leu Gly Ile
1345                1350                1355                    1360

Ser Val Thr Gly Gly Val Asn Thr Ser Val Arg His Gly Gly Ile Tyr
                    1365                1370                    1375

Val Lys Asp Val Ile Pro Gln Gly Ala Ala Glu Ser Asp Gly Arg Ile
                    1380                1385                    1390

His Lys Gly Asp Arg Val Leu Ala Val Asn Gly Val Ser Leu Glu Gly
                    1395                1400                    1405

Ala Thr His Lys Gln Ala Val Glu Thr Leu Arg Asn Thr Gly Gln Val
                    1410                1415                    1420

Val His Leu Leu Leu Glu Lys Gly Gln Ser Pro Thr Ser Lys Glu His
1425                1430                1435                    1440

Val Pro Val Thr Pro Gln Cys Thr Leu Ser Asp Gln Asn Ala Gln Gly
                    1445                1450                    1455

Gln Gly Pro Glu Lys Val Lys Lys Thr Thr Gln Val Lys Asp Tyr Ser
                    1460                1465                    1470

Phe Val Thr Glu Glu Asn Thr Phe Glu Val Lys Leu Phe Lys Asn Ser
                    1475                1480                    1485

Ser Gly Leu Gly Phe Ser Phe Ser Arg Glu Asp Asn Leu Ile Pro Glu
                    1490                1495                    1500

Gln Ile Asn Ala Ser Ile Val Arg Val Lys Lys Leu Phe Ala Gly Gln
1505                1510                1515                    1520

Pro Ala Ala Glu Ser Gly Lys Ile Asp Val Gly Asp Val Ile Leu Lys
                    1525                1530                    1535

Val Asn Gly Ala Ser Leu Lys Gly Leu Ser Gln Gln Glu Val Ile Ser
                    1540                1545                    1550

Ala Leu Arg Gly Thr Ala Pro Glu Val Phe Leu Leu Leu Cys Arg Pro
                    1555                1560                    1565

Pro Pro Gly Val Leu Pro Glu Ile Asp Thr Ala Leu Leu Thr Pro Leu
                    1570                1575                    1580

```
Gln  Ser  Pro  Ala  Gln  Val  Leu  Pro  Asn  Ser  Ser  Lys  Asp  Ser  Ser  Gln
1585                1590                1595                          1600

Pro  Ser  Cys  Val  Glu  Gln  Ser  Thr  Ser  Ser  Asp  Glu  Asn  Glu  Met  Ser
                    1605                1610                          1615

Asp  Lys  Ser  Lys  Lys  Gln  Cys  Lys  Ser  Pro  Ser  Arg  Arg  Asp  Ser  Tyr
               1620                1625                          1630

Ser  Asp  Ser  Ser  Gly  Ser  Gly  Glu  Asp  Asp  Leu  Val  Thr  Ala  Pro  Ala
               1635                1640                     1645

Asn  Ile  Ser  Asn  Ser  Thr  Trp  Ser  Ser  Ala  Leu  His  Gln  Thr  Leu  Ser
          1650                1655                     1660

Asn  Met  Val  Ser  Gln  Ala  Gln  Ser  His  His  Glu  Ala  Pro  Lys  Ser  Gln
1665                1670                1675                          1680

Glu  Asp  Thr  Ile  Cys  Thr  Met  Phe  Tyr  Tyr  Pro  Gln  Lys  Ile  Pro  Asn
                    1685                1690                          1695

Lys  Pro  Glu  Phe  Glu  Asp  Ser  Asn  Pro  Ser  Pro  Leu  Pro  Pro  Asp  Met
                    1700                1705                          1710

Ala  Pro  Gly  Gln  Ser  Tyr  Gln  Pro  Gln  Ser  Glu  Ser  Ala  Ser  Ser  Ser
               1715                1720                     1725

Ser  Met  Asp  Lys  Tyr  His  Ile  His  His  Ile  Ser  Glu  Pro  Thr  Arg  Gln
                    1730                1735                     1740

Glu  Asn  Trp  Thr  Pro  Leu  Lys  Asn  Asp  Leu  Glu  Asn  His  Leu  Glu  Asp
1745                1750                1755                          1760

Phe  Glu  Leu  Glu  Val  Glu  Leu  Leu  Ile  Thr  Leu  Ile  Lys  Ser  Glu  Lys
                    1765                1770                          1775

Ala  Ser  Leu  Gly  Phe  Thr  Val  Thr  Lys  Gly  Asn  Gln  Arg  Ile  Gly  Cys
               1780                1785                          1790

Tyr  Val  His  Asp  Val  Ile  Gln  Asp  Pro  Ala  Lys  Ser  Asp  Gly  Arg  Leu
               1795                1800                     1805

Lys  Pro  Gly  Asp  Arg  Leu  Ile  Lys  Val  Asn  Asp  Thr  Asp  Val  Thr  Asn
               1810                1815                     1820

Met  Thr  His  Thr  Asp  Ala  Val  Asn  Leu  Leu  Arg  Ala  Ala  Ser  Lys  Thr
1825                1830                1835                          1840

Val  Arg  Leu  Val  Ile  Gly  Arg  Val  Pro  Arg  Ile  Thr  Gln  Asn  Thr  Asn
                    1845                1850                          1855

Val  Ala  Ser  Phe  Ala  Thr  Gly  His  Lys  Leu  Thr  Cys  Asn  Lys  Glu  Glu
                    1860                1865                          1870

Leu  Gly  Phe  Ser  Leu  Cys  Gly  Gly  His  Asp  Ser  Leu  Tyr  Gln  Val  Val
                    1875                1880                     1885

Tyr  Ile  Ser  Asp  Ile  Asn  Pro  Arg  Ser  Val  Ala  Ala  Ile  Glu  Gly  Asn
               1890                1895                     1900

Leu  Gln  Leu  Leu  Asp  Val  Ile  His  Tyr  Val  Asn  Gly  Val  Ser  Thr  Gln
1905                1910                1915                          1920

Gly  Met  Thr  Leu  Glu  Glu  Val  Asn  Arg  Ala  Leu  Asp  Met  Ser  Leu  Pro
                    1925                1930                          1935

Ser  Leu  Val  Leu  Lys  Ala  Thr  Arg  Asn  Asp  Leu  Pro  Val  Val  Pro  Ser
                    1940                1945                          1950

Ser  Lys  Arg  Ser  Ala  Val  Ser  Ala  Pro  Lys  Ser  Thr  Lys  Gly  Asn  Gly
               1955                1960                     1965

Ser  Tyr  Ser  Val  Gly  Ser  Cys  Ser  Gln  Pro  Ala  Leu  Thr  Pro  Asn  Asp
               1970                1975                     1980

Ser  Phe  Ser  Thr  Val  Ala  Gly  Glu  Glu  Ile  Asn  Glu  Ile  Ser  Tyr  Pro
               1985                1990                     1995                2000

Lys  Gly  Lys  Cys  Ser  Thr  Tyr  Gln  Ile  Lys  Gly  Ser  Pro  Asn  Leu  Thr
                    2005                2010                          2015
```

```
Leu  Pro  Lys  Glu  Ser  Tyr  Ile  Gln  Glu  Asp  Asp  Ile  Tyr  Asp  Asp  Ser
               2020                    2025                    2030

Gln  Glu  Ala  Glu  Val  Ile  Gln  Ser  Leu  Leu  Asp  Val  Val  Asp  Glu  Glu
               2035                    2040                    2045

Ala  Gln  Asn  Leu  Leu  Asn  Glu  Asn  Asn  Ala  Ala  Gly  Asp  Ser  Cys  Gly
               2050                    2055                    2060

Pro  Gly  Thr  Leu  Lys  Met  Asn  Gly  Lys  Leu  Ser  Glu  Glu  Arg  Thr  Glu
2065                    2070                    2075                    2080

Asp  Thr  Asp  Cys  Asp  Gly  Ser  Pro  Leu  Pro  Glu  Tyr  Phe  Thr  Glu  Ala
               2085                    2090                    2095

Thr  Lys  Met  Asn  Gly  Cys  Glu  Glu  Tyr  Cys  Glu  Glu  Lys  Val  Lys  Ser
               2100                    2105                    2110

Glu  Ser  Leu  Ile  Gln  Lys  Pro  Gln  Lys  Lys  Thr  Asp  Asp  Asp  Glu
               2115                    2120                    2125

Ile  Thr  Trp  Gly  Asn  Asp  Glu  Leu  Pro  Ile  Glu  Arg  Thr  Asn  His  Glu
               2130                    2135                    2140

Asp  Ser  Asp  Lys  Asp  His  Ser  Phe  Leu  Thr  Asn  Asp  Glu  Leu  Ala  Val
2145                    2150                    2155                    2160

Leu  Pro  Val  Val  Lys  Val  Leu  Pro  Ser  Gly  Lys  Tyr  Thr  Gly  Ala  Asn
               2165                    2170                    2175

Leu  Lys  Ser  Val  Ile  Arg  Val  Leu  Arg  Gly  Leu  Leu  Asp  Gln  Gly  Ile
               2180                    2185                    2190

Pro  Ser  Lys  Glu  Leu  Glu  Asn  Leu  Gln  Glu  Leu  Lys  Pro  Leu  Asp  Gln
               2195                    2200                    2205

Cys  Leu  Ile  Gly  Gln  Thr  Lys  Glu  Asn  Arg  Arg  Lys  Asn  Arg  Tyr  Lys
               2210                    2215                    2220

Asn  Ile  Leu  Pro  Tyr  Asp  Ala  Thr  Arg  Val  Pro  Leu  Gly  Asp  Glu  Gly
2225                    2230                    2235                    2240

Gly  Tyr  Ile  Asn  Ala  Ser  Phe  Ile  Lys  Ile  Pro  Val  Gly  Lys  Glu  Glu
               2245                    2250                    2255

Phe  Val  Tyr  Ile  Ala  Cys  Gln  Gly  Pro  Leu  Pro  Thr  Thr  Val  Gly  Asp
               2260                    2265                    2270

Phe  Trp  Gln  Met  Ile  Trp  Glu  Gln  Lys  Ser  Thr  Val  Ile  Ala  Met  Met
               2275                    2280                    2285

Thr  Gln  Glu  Val  Glu  Gly  Glu  Lys  Ile  Lys  Cys  Gln  Arg  Tyr  Trp  Pro
               2290                    2295                    2300

Asn  Ile  Leu  Gly  Lys  Thr  Thr  Met  Val  Ser  Asn  Arg  Leu  Arg  Leu  Ala
2305                    2310                    2315                    2320

Leu  Val  Arg  Met  Gln  Gln  Leu  Lys  Gly  Phe  Val  Val  Arg  Ala  Met  Thr
               2325                    2330                    2335

Leu  Glu  Asp  Ile  Gln  Thr  Arg  Glu  Val  Arg  His  Ile  Ser  His  Leu  Asn
               2340                    2345                    2350

Phe  Thr  Ala  Trp  Pro  Asp  His  Asp  Thr  Pro  Ser  Gln  Pro  Asp  Asp  Leu
               2355                    2360                    2365

Leu  Thr  Phe  Ile  Ser  Tyr  Met  Arg  His  Ile  His  Arg  Ser  Gly  Pro  Ile
               2370                    2375                    2380

Ile  Thr  His  Cys  Ser  Ala  Gly  Ile  Gly  Arg  Ser  Gly  Thr  Leu  Ile  Cys
2385                    2390                    2395                    2400

Ile  Asp  Val  Val  Leu  Gly  Leu  Ile  Ser  Gln  Asp  Leu  Asp  Phe  Asp  Ile
               2405                    2410                    2415

Ser  Asp  Leu  Val  Arg  Cys  Met  Arg  Leu  Gln  Arg  His  Gly  Met  Val  Gln
               2420                    2425                    2430

Thr  Glu  Asp  Gln  Tyr  Ile  Phe  Cys  Tyr  Gln  Val  Ile  Leu  Tyr  Val  Leu
```

|   | 2435 |   |   |   |   | 2440 |   |   |   |   | 2445 |   |   |   |
|---|---|---|---|---|---|---|---|---|---|---|---|---|---|---|

Thr Arg Leu Gln Ala Glu Glu Glu Gln Lys Gln Gln Pro Gln Leu Leu
                2450                    2455              2460

Lys
2465

(2) INFORMATION FOR SEQ ID NO:4:

(i) SEQUENCE CHARACTERISTICS:
        (A) LENGTH: 369 amino acids
        (B) TYPE: amino acid
        (D) TOPOLOGY: linear (ii) MOLECULE TYPE: protein (xi) SEQUENCE DESCRIPTION: SEQ ID NO:4:

Met Val Gln Pro Glu Gln Ala Pro Lys Val Leu Asn Val Val Asp
 1               5                  10                  15

Pro Gln Gly Arg Gly Ala Pro Glu Ile Lys Ala Thr Thr Ala Thr Ser
                20                  25                  30

Val Cys Pro Ser Pro Phe Lys Met Lys Pro Ile Gly Leu Gln Glu Arg
            35                  40                  45

Arg Gly Ser Asn Val Ser Leu Thr Leu Asp Met Ser Ser Leu Gly Asn
        50                  55                  60

Ile Glu Pro Phe Val Ser Ile Pro Thr Pro Arg Glu Lys Val Ala Met
 65                  70                  75                  80

Glu Tyr Leu Gln Ser Ala Ser Arg Ile Leu Asp Lys Val Gln Leu Arg
                85                  90                  95

Asp Val Val Ala Ser Ser His Leu Leu Gln Ser Glu Phe Met Glu Ile
                100                 105                 110

Pro Met Asn Phe Val Asp Pro Lys Glu Ile Asp Ile Pro Arg His Gly
            115                 120                 125

Thr Lys Asn Arg Tyr Lys Thr Ile Leu Pro Asn Pro Leu Ser Arg Val
    130                 135                 140

Cys Leu Arg Pro Lys Asn Val Thr Asp Ser Leu Ser Thr Tyr Ile Asn
145                 150                 155                 160

Ala Asn Tyr Ile Arg Gly Tyr Ser Gly Lys Glu Lys Ala Phe Ile Ala
                165                 170                 175

Thr Gln Gly Pro Met Ile Asn Thr Val Asp Asp Phe Trp Gln Met Val
            180                 185                 190

Trp Gln Glu Asp Ser Pro Val Ile Val Met Ile Thr Lys Leu Lys Glu
        195                 200                 205

Lys Asn Glu Lys Cys Val Leu Tyr Trp Pro Glu Lys Arg Gly Ile Tyr
    210                 215                 220

Gly Lys Val Glu Val Leu Val Ile Ser Val Asn Glu Cys Asp Asn Tyr
225                 230                 235                 240

Thr Ile Arg Asn Leu Val Leu Lys Gln Gly Ser His Thr Gln His Val
                245                 250                 255

Ser Asn Tyr Trp Tyr Thr Ser Trp Pro Asp His Lys Thr Pro Asp Ser
            260                 265                 270

Ala Gln Pro Leu Leu Gln Leu Met Leu Asp Val Glu Glu Asp Arg Leu
        275                 280                 285

Ala Ser Gln Gly Pro Arg Ala Val Val Val His Cys Ser Ala Gly Ile
    290                 295                 300

Gly Arg Thr Gly Cys Phe Ile Ala Thr Ser Ile Gly Cys Gln Gln Leu
305                 310                 315                 320

| Lys | Glu | Glu | Gly | Val | Val | Asp | Ala | Leu | Ser | Ile | Val | Cys | Gln | Leu | Arg |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Met | Asp | Arg | Gly | Gly | Met | Val | Gln | Thr | Ser | Glu | Gln | Tyr | Glu | Phe | Val |
|-----|-----|-----|-----|-----|-----|-----|-----|-----|-----|-----|-----|-----|-----|-----|-----|
|     |     |     | 340 |     |     |     |     | 345 |     |     |     |     | 350 |     |     |

| His | His | Ala | Leu | Cys | Leu | Tyr | Glu | Ser | Arg | Leu | Ser | Ala | Glu | Thr | Val |
|-----|-----|-----|-----|-----|-----|-----|-----|-----|-----|-----|-----|-----|-----|-----|-----|
|     |     | 355 |     |     |     |     | 360 |     |     |     |     | 365 |     |     |     |

Gln (2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Region
        (B) LOCATION: 5
        (D) OTHER INFORMATION: /note= "Xaa = I or V"

(xi) SEQUENCE DESCRIPTION: SEQ ID NO:5:

| Phe | Trp | Arg | Met | Xaa | Trp | Glu | Gln |
|-----|-----|-----|-----|-----|-----|-----|-----|
| 1   |     |     |     | 5   |     |     |     |

(2) INFORMATION FOR SEQ ID NO:6:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:6:

TTCTGGMGNA TGATNTGGGA ACA                23

(2) INFORMATION FOR SEQ ID NO:7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (ix) FEATURE:
        (A) NAME/KEY: Region
        (B) LOCATION: 3
        (D) OTHER INFORMATION: /note= "Xaa = A or D"

(xi) SEQUENCE DESCRIPTION: SEQ ID NO:7:

| Lys | Cys | Xaa | Glx | Tyr | Trp | Pro |
|-----|-----|-----|-----|-----|-----|-----|
| 1   |     |     |     | 5   |     |     |

( 2 ) INFORMATION FOR SEQ ID NO:8:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:8:

AARTGYGANC AGTAYTGGCC      20

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( i x ) FEATURE:
        ( A ) NAME/KEY: Region
        ( B ) LOCATION: 6
        ( D ) OTHER INFORMATION: /note= "Xaa = V or I"

( x i ) SEQUENCE DESCRIPTION: SEQ ID NO:9:

His Cys Ser Ala Gly Xaa Gly
1               5

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:10:

CCNACNCCMG CRCTGCAGTG      20

( 2 ) INFORMATION FOR SEQ ID NO:11:

( i ) SEQUENCE CHARACTERISTICS:
        ( A ) LENGTH: 303 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:11:

Arg Lys Val Asn Ile Met Leu Leu Asn Gly Gln Arg Leu Glu Leu Thr
1            5                      10                  15

Cys Asp Thr Lys Thr Ile Cys Lys Asp Val Phe Asp Met Val Val Ala

|    |     |     |     |     |     | 20  |     |     |     |     | 25  |     |     |     |     | 30  |     |
| --- | --- | --- | --- | --- | --- | --- | --- | --- | --- | --- | --- | --- | --- | --- | --- | --- | --- |
|     | His | Ile | Gly | Leu | Val | Glu | His | His | Leu | Phe | Ala | Leu | Ala | Thr | Leu | Lys |     |
|     |     |     | 35  |     |     |     |     | 40  |     |     |     |     | 45  |     |     |     |     |
|     | Asp | Asn | Glu | Tyr | Phe | Phe | Val | Asp | Pro | Asp | Leu | Lys | Leu | Thr | Lys | Val |     |
|     |     |     | 50  |     |     |     | 55  |     |     |     |     | 60  |     |     |     |     |     |
|     | Ala | Pro | Glu | Gly | Trp | Lys | Glu | Glu | Pro | Lys | Lys | Lys | Thr | Lys | Ala | Thr |     |
|     | 65  |     |     |     |     | 70  |     |     |     |     | 75  |     |     |     |     | 80  |     |
|     | Val | Asn | Phe | Thr | Leu | Phe | Phe | Arg | Ile | Lys | Phe | Phe | Met | Asp | Asp | Val |     |
|     |     |     |     |     | 85  |     |     |     |     | 90  |     |     |     |     | 95  |     |     |
|     | Ser | Leu | Ile | Gln | His | Thr | Leu | Thr | Cys | His | Gln | Tyr | Tyr | Leu | Gln | Leu |     |
|     |     |     |     | 100 |     |     |     |     | 105 |     |     |     |     | 110 |     |     |     |
|     | Arg | Lys | Asp | Ile | Leu | Glu | Glu | Arg | Met | His | Cys | Asp | Asp | Glu | Thr | Ser |     |
|     |     |     |     | 115 |     |     |     |     | 120 |     |     |     |     | 125 |     |     |     |
|     | Leu | Leu | Leu | Ala | Ser | Leu | Ala | Leu | Gln | Ala | Glu | Tyr | Gly | Asp | Tyr | Gln |     |
|     |     |     | 130 |     |     |     | 135 |     |     |     |     | 140 |     |     |     |     |     |
|     | Pro | Glu | Val | His | Gly | Val | Ser | Tyr | Phe | Arg | Met | Glu | His | Tyr | Leu | Pro |     |
|     | 145 |     |     |     |     | 150 |     |     |     |     | 155 |     |     |     |     | 160 |     |
|     | Ala | Arg | Val | Met | Glu | Lys | Leu | Asp | Leu | Ser | Tyr | Ile | Lys | Glu | Glu | Leu |     |
|     |     |     |     |     | 165 |     |     |     |     | 170 |     |     |     |     | 175 |     |     |
|     | Pro | Lys | Leu | His | Asn | Thr | Tyr | Val | Gly | Ala | Ser | Glu | Lys | Glu | Thr | Glu |     |
|     |     |     |     | 180 |     |     |     |     | 185 |     |     |     |     | 190 |     |     |     |
|     | Leu | Glu | Phe | Leu | Lys | Val | Cys | Gln | Arg | Leu | Thr | Glu | Tyr | Gly | Val | His |     |
|     |     |     | 195 |     |     |     |     | 200 |     |     |     |     | 205 |     |     |     |     |
|     | Phe | His | Arg | Val | His | Pro | Glu | Lys | Lys | Ser | Gln | Thr | Gly | Ile | Leu | Leu |     |
|     |     |     | 210 |     |     |     |     | 215 |     |     |     |     | 220 |     |     |     |     |
|     | Gly | Val | Cys | Ser | Lys | Gly | Val | Leu | Val | Phe | Glu | Val | His | Asn | Gly | Val |     |
|     | 225 |     |     |     |     | 230 |     |     |     |     | 235 |     |     |     |     | 240 |     |
|     | Arg | Thr | Leu | Val | Leu | Arg | Phe | Pro | Trp | Arg | Glu | Thr | Lys | Lys | Ile | Ser |     |
|     |     |     |     |     | 245 |     |     |     |     | 250 |     |     |     |     | 255 |     |     |
|     | Phe | Ser | Lys | Lys | Lys | Ile | Thr | Leu | Gln | Asn | Thr | Ser | Asp | Gly | Ile | Lys |     |
|     |     |     |     | 260 |     |     |     |     | 265 |     |     |     |     | 270 |     |     |     |
|     | His | Gly | Phe | Gln | Thr | Asp | Asn | Ser | Lys | Ile | Cys | Gln | Tyr | Leu | Leu | His |     |
|     |     |     | 275 |     |     |     |     | 280 |     |     |     |     | 285 |     |     |     |     |
|     | Leu | Cys | Ser | Tyr | Gln | His | Lys | Phe | Gln | Leu | Gln | Met | Arg | Ala | Arg |     |     |
|     |     | 290 |     |     |     |     | 295 |     |     |     |     | 300 |     |     |     |     |     |

( 2 ) INFORMATION FOR SEQ ID NO:12:

( i ) SEQUENCE CHARACTERISTICS:
        ( A ) LENGTH: 296 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:12:

|     | Ile | Asn | Val | Arg | Val | Thr | Thr | Met | Asp | Ala | Glu | Leu | Glu | Phe | Ala | Ile |
| --- | --- | --- | --- | --- | --- | --- | --- | --- | --- | --- | --- | --- | --- | --- | --- | --- |
|     | 1   |     |     |     | 5   |     |     |     |     | 10  |     |     |     |     | 15  |     |
|     | Gln | Pro | Asn | Thr | Thr | Gly | Lys | Gln | Leu | Phe | Asp | Gln | Val | Val | Lys | Thr |
|     |     |     |     | 20  |     |     |     |     | 25  |     |     |     |     | 30  |     |     |
|     | Ile | Gly | Leu | Arg | Glu | Val | Trp | Tyr | Phe | Gly | Leu | His | Tyr | Val | Asp | Asn |
|     |     |     |     | 35  |     |     |     |     | 40  |     |     |     |     | 45  |     |     |
|     | Lys | Gly | Phe | Pro | Thr | Trp | Leu | Lys | Leu | Asp | Lys | Lys | Val | Ser | Ala | Gln |

|  |  |  |  | 50 |  |  |  | 55 |  |  |  | 60 |  |  |  |
|---|---|---|---|---|---|---|---|---|---|---|---|---|---|---|---|
| Glu<br>65 | Val | Arg | Lys | Glu | Asn<br>70 | Pro | Leu | Gln | Phe | Lys<br>75 | Phe | Arg | Ala | Lys | Phe<br>80 |
| Tyr | Pro | Glu | Asp | Val<br>85 | Ala | Glu | Leu | Ile | Gln<br>90 | Asp | Ile | Thr | Gln<br>95 | Lys |
| Leu | Phe | Phe | Leu<br>100 | Gln | Val | Lys | Glu | Gly<br>105 | Ile | Leu | Ser | Asp<br>110 | Glu | Ile | Tyr |
| Cys | Pro | Pro<br>115 | Glu | Thr | Ala | Val | Leu<br>120 | Leu | Gly | Ser | Tyr<br>125 | Ala | Val | Gln | Ala |
| Lys | Phe<br>130 | Gly | Asp | Tyr | Asn<br>135 | Lys | Glu | Val | His | Lys<br>140 | Ser | Gly | Tyr | Leu | Ser |
| Ser<br>145 | Glu | Arg | Leu | Ile | Pro<br>150 | Gln | Arg | Val | Met | Asp<br>155 | Gln | His | Lys | Leu | Thr<br>160 |
| Arg | Asp | Gln | Trp | Glu<br>165 | Asp | Arg | Ile | Gln | Val<br>170 | Trp | His | Ala | Glu | His<br>175 | Arg |
| Gly | Met | Leu | Lys<br>180 | Asp | Asn | Ala | Met | Leu<br>185 | Glu | Tyr | Leu | Lys | Ile<br>190 | Ala | Gln |
| Asp | Leu | Glu<br>195 | Met | Tyr | Gly | Ile | Asn<br>200 | Tyr | Phe | Glu | Ile | Lys<br>205 | Asn | Lys | Lys |
| Gly | Thr<br>210 | Asp | Leu | Trp | Leu | Gly<br>215 | Val | Asp | Ala | Leu | Gly<br>220 | Leu | Asn | Ile | Tyr |
| Glu<br>225 | Lys | Asp | Asp | Lys | Leu<br>230 | Thr | Pro | Lys | Ile | Gly<br>235 | Phe | Pro | Trp | Ser | Glu<br>240 |
| Ile | Arg | Asn | Ile | Ser<br>245 | Phe | Asn | Asp | Lys | Lys<br>250 | Phe | Val | Ile | Lys | Pro<br>255 | Ile |
| Asp | Lys | Lys | Ala<br>260 | Pro | Asp | Phe | Val | Phe<br>265 | Tyr | Ala | Pro | Arg | Leu<br>270 | Arg | Ile |
| Asn | Lys | Arg<br>275 | Ile | Leu | Gln | Leu | Cys<br>280 | Met | Gly | Asn | His | Glu<br>285 | Leu | Tyr | Met |
| Arg | Arg<br>290 | Arg | Lys | Pro | Asp | Thr<br>295 | Ile |  |  |  |  |  |  |  |  |

( 2 ) INFORMATION FOR SEQ ID NO:13:

( i ) SEQUENCE CHARACTERISTICS:
        ( A ) LENGTH: 247 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:13:

| Met<br>1 | His | Cys | Lys | Val<br>5 | Ser | Leu | Leu | Asp | Asp<br>10 | Thr | Val | Tyr | Glu | Cys<br>15 | Val |
|---|---|---|---|---|---|---|---|---|---|---|---|---|---|---|---|
| Val | Glu | Lys | His<br>20 | Ala | Lys | Gly | Gln | Asp<br>25 | Leu | Leu | Lys | Arg | Val<br>30 | Cys | Glu |
| His | Leu | Asn<br>35 | Leu | Leu | Glu | Glu | Asp<br>40 | Tyr | Phe | Gly | Leu | Ala<br>45 | Ile | Trp | Asp |
| Asn | Ala<br>50 | Asp | Ile | Thr | Arg | Tyr<br>55 | Tyr | Leu | Cys | Leu | Gln<br>60 | Leu | Arg | Gln | Asp |
| Ile<br>65 | Val | Ala | Gly | Arg | Leu<br>70 | Pro | Cys | Ser | Phe | Ala<br>75 | Thr | Leu | Ala | Leu | Leu<br>80 |
| Gly | Ser | Tyr | Thr | Ile | Gln | Ser | Glu | Leu | Gly | Asp | Tyr | Asp | Pro | Glu | Leu |

|     |     |     |     | 85  |     |     |     |     | 90  |     |     |     |     | 95  |     |
| --- | --- | --- | --- | --- | --- | --- | --- | --- | --- | --- | --- | --- | --- | --- | --- |
| His | Gly | Val | Asp<br>100 | Tyr | Val | Ser | Asp | Phe<br>105 | Lys | Leu | Ala | Pro | Asn<br>110 | Gln | Thr |
| Lys | Glu | Leu<br>115 | Glu | Glu | Lys | Val | Met<br>120 | Glu | Leu | His | Lys | Ser<br>125 | Tyr | Arg | Ser |
| Met | Thr<br>130 | Pro | Ala | Gln | Ala | Asp<br>135 | Leu | Glu | Phe | Leu | Glu<br>140 | Asn | Ala | Lys | Lys |
| Leu<br>145 | Ser | Met | Tyr | Gly | Val<br>150 | Asp | Leu | His | Lys | Ala<br>155 | Lys | Asp | Leu | Glu | Gly<br>160 |
| Val | Asp | Ile | Ile | Leu<br>165 | Gly | Val | Cys | Ser | Ser<br>170 | Gly | Leu | Leu | Val | Tyr<br>175 | Lys |
| Asp | Lys | Leu | Arg<br>180 | Ile | Asn | Arg | Phe | Pro<br>185 | Trp | Pro | Lys | Val | Leu<br>190 | Lys | Ile |
| Ser | Tyr | Lys<br>195 | Arg | Ser | Ser | Phe | Phe<br>200 | Ile | Lys | Ile | Arg | Pro<br>205 | Gly | Glu | Gln |
| Glu | Gln<br>210 | Tyr | Glu | Ser | Thr | Ile<br>215 | Gly | Phe | Lys | Leu | Pro<br>220 | Ser | Tyr | Arg | Ala |
| Ala<br>225 | Lys | Lys | Leu | Trp | Lys<br>230 | Val | Cys | Val | Glu | His<br>235 | His | Thr | Phe | Phe | Arg<br>240 |
| Leu | Thr | Ser | Thr | Asp<br>245 | Thr | Ile |     |     |     |     |     |     |     |     |     |

( 2 ) INFORMATION FOR SEQ ID NO:14:

( i ) SEQUENCE CHARACTERISTICS:
        ( A ) LENGTH: 288 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:14:

| Val<br>1 | Val | Cys | Asn | Ile<br>5 | Leu | Leu | Leu | Asp | Asn<br>10 | Thr | Val | Gln | Ala | Phe<br>15 | Lys |
| --- | --- | --- | --- | --- | --- | --- | --- | --- | --- | --- | --- | --- | --- | --- | --- |
| Val | Asn | Lys | His<br>20 | Asp | Gln | Gly | Gln | Val<br>25 | Leu | Leu | Asp | Val | Val<br>30 | Phe | Lys |
| His | Leu | Asp<br>35 | Leu | Thr | Glu | Gln | Asp<br>40 | Tyr | Phe | Gly | Leu | Gln<br>45 | Leu | Ala | Asp |
| Asp | Ser<br>50 | Thr | Asp | Asn | Pro | Arg<br>55 | Trp | Leu | Asp | Pro | Asn<br>60 | Lys | Pro | Ile | Arg |
| Lys<br>65 | Gln | Leu | Lys | Arg | Gly<br>70 | Ser | Pro | Tyr | Ser | Leu<br>75 | Asn | Phe | Arg | Val | Lys<br>80 |
| Phe | Phe | Val | Ser | Asp<br>85 | Pro | Asn | Lys | Leu | Gln<br>90 | Glu | Glu | Tyr | Thr | Arg<br>95 | Tyr |
| Gln | Tyr | Phe | Leu<br>100 | Gln | Ile | Lys | Gln | Asp<br>105 | Ile | Leu | Thr | Gly | Arg<br>110 | Leu | Pro |
| Cys | Pro | Ser | Asn | Thr<br>115 | Ala | Ala | Leu | Leu<br>120 | Ala | Ser | Phe | Ala | Val<br>125 | Gln | Ser |
| Glu | Leu<br>130 | Gly | Asp | Tyr | Asp | Gln<br>135 | Ser | Glu | Asn | Leu | Ser<br>140 | Gly | Tyr | Leu | Ser |
| Asp<br>145 | Tyr | Ser | Phe | Ile | Pro<br>150 | Asn | Gln | Pro | Gln | Asp<br>155 | Phe | Glu | Lys | Glu | Ile<br>160 |
| Ala | Lys | Leu | His | Gln | Gln | His | Ile | Gly | Leu | Ser | Pro | Ala | Glu | Ala | Glu |

-continued

```
              165                         170                         175
Phe  Asn  Tyr  Leu  Asn  Thr  Ala  Arg  Thr  Leu  Glu  Leu  Tyr  Gly  Val  Glu
               180                         185                         190

Phe  His  Tyr  Ala  Arg  Asp  Gln  Ser  Asn  Asn  Glu  Ile  Met  Ile  Gly  Val
          195                         200                         205

Met  Ser  Gly  Gly  Ile  Leu  Ile  Tyr  Lys  Asn  Arg  Val  Arg  Met  Asn  Thr
     210                         215                         220

Phe  Pro  Trp  Leu  Lys  Ile  Val  Lys  Ile  Ser  Phe  Lys  Cys  Lys  Gln  Phe
225                         230                         235                         240

Phe  Ile  Gln  Leu  Arg  Lys  Glu  Leu  His  Glu  Ser  Arg  Glu  Thr  Leu  Leu
                    245                         250                         255

Gly  Phe  Asn  Met  Val  Asn  Tyr  Arg  Ala  Cys  Lys  Asn  Leu  Trp  Lys  Ala
               260                         265                         270

Cys  Val  Glu  His  His  Thr  Phe  Phe  Arg  Leu  Asp  Arg  Pro  Leu  Pro  Pro
               275                         280                         285
```

(2) INFORMATION FOR SEQ ID NO:15:

(i) SEQUENCE CHARACTERISTICS:
        (A) LENGTH: 288 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:15:

```
Val  Ile  Cys  Ser  Ile  His  Phe  Leu  Asp  Gly  Val  Val  Gln  Thr  Phe  Lys
1                   5                        10                             15

Val  Thr  Lys  Gln  Asp  Thr  Gly  Gln  Val  Leu  Leu  Asp  Met  Val  His  Asn
               20                         25                         30

His  Leu  Gly  Val  Thr  Glu  Lys  Glu  Tyr  Phe  Gly  Leu  Gln  His  Asp  Asp
          35                         40                         45

Asp  Ser  Val  Asp  Ser  Pro  Arg  Trp  Leu  Glu  Ala  Ser  Lys  Pro  Ile  Arg
50                         55                         60

Lys  Gln  Leu  Lys  Gly  Gly  Phe  Pro  Cys  Thr  Leu  His  Phe  Arg  Val  Arg
65                         70                         75                         80

Phe  Phe  Ile  Pro  Asp  Pro  Asn  Thr  Leu  Gln  Gln  Glu  Gln  Thr  Arg  His
                    85                         90                         95

Leu  Tyr  Phe  Leu  Gln  Leu  Lys  Met  Asp  Ile  Cys  Glu  Gly  Arg  Leu  Thr
               100                        105                        110

Cys  Pro  Leu  Asn  Ser  Ala  Val  Val  Leu  Ala  Ser  Tyr  Ala  Val  Gln  Ser
          115                        120                        125

His  Phe  Gly  Asp  Tyr  Asn  Ser  Ser  Ile  His  His  Pro  Gly  Tyr  Leu  Ser
     130                        135                        140

Asp  Ser  His  Phe  Ile  Pro  Asp  Gln  Asn  Glu  Asp  Phe  Leu  Thr  Lys  Val
145                        150                        155                        160

Glu  Ser  Leu  His  Glu  Gln  His  Ser  Gly  Leu  Lys  Gln  Ser  Glu  Ala  Glu
                    165                        170                        175

Ser  Cys  Tyr  Ile  Asn  Ile  Ala  Arg  Thr  Leu  Asp  Phe  Tyr  Gly  Val  Glu
               180                        185                        190

Leu  His  Ser  Gly  Arg  Asp  Leu  His  Asn  Leu  Asp  Leu  Met  Ile  Gly  Ile
          195                        200                        205

Ala  Ser  Ala  Gly  Val  Ala  Val  Tyr  Arg  Lys  Tyr  Ile  Cys  Thr  Ser  Phe
```

```
                   210                      215                      220
        Tyr  Pro  Trp  Val  Asn  Ile  Leu  Lys  Ile  Ser  Phe  Lys  Arg  Lys  Lys  Phe
        225                      230                      235                      240

Phe  Ile  His  Gln  Arg  Gln  Lys  Gln  Ala  Glu  Ser  Arg  Glu  His  Ile  Val
                            245                      250                      255

Ala  Phe  Asn  Met  Leu  Asn  Tyr  Arg  Ser  Cys  Lys  Asn  Leu  Trp  Lys  Ser
                            260                      265                      270

Cys  Val  Glu  His  His  Thr  Phe  Phe  Gln  Ala  Lys  Lys  Leu  Leu  Pro  Gln
                            275                      280                      285
```

( 2 ) INFORMATION FOR SEQ ID NO:16:

( i ) SEQUENCE CHARACTERISTICS:
        ( A ) LENGTH: 77 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:16:

```
        Asp  Ala  Lys  Tyr  Gly  Leu  Gly  Phe  Gln  Ile  Ile  Gly  Gly  Glu  Lys  Met
        1                   5                       10                      15

Gly  Arg  Leu  Asp  Leu  Gly  Ile  Phe  Ile  Ser  Ser  Val  Ala  Pro  Gly  Gly
                            20                      25                      30

Pro  Ala  Asp  Phe  His  Gly  Cys  Leu  Lys  Pro  Gly  Asp  Arg  Leu  Ile  Ser
                            35                      40                      45

Val  Asn  Ser  Val  Ser  Leu  Glu  Gly  Val  Ser  His  His  Ala  Ala  Ile  Glu
                  50                      55                      60

Ile  Leu  Gln  Asn  Ala  Pro  Glu  Asp  Val  Thr  Leu  Val  Ile
        65                      70                      75
```

( 2 ) INFORMATION FOR SEQ ID NO:17:

( i ) SEQUENCE CHARACTERISTICS:
        ( A ) LENGTH: 77 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:17:

```
        Lys  Asn  Asp  Asn  Ser  Leu  Gly  Ile  Ser  Val  Thr  Gly  Gly  Val  Asn  Thr
        1                   5                       10                      15

Ser  Val  Arg  His  Gly  Gly  Ile  Tyr  Val  Lys  Ala  Val  Ile  Pro  Gln  Gly
                            20                      25                      30

Ala  Ala  Glu  Ser  Asp  Gly  Arg  Ile  His  Lys  Gly  Asp  Arg  Val  Leu  Ala
                            35                      40                      45

Val  Asn  Gly  Val  Ser  Leu  Glu  Gly  Ala  Thr  His  Lys  Gln  Ala  Val  Glu
                  50                      55                      60

Thr  Leu  Arg  Asn  Thr  Gly  Gln  Val  Val  His  Leu  Leu  Leu
        65                      70                      75
```

( 2 ) INFORMATION FOR SEQ ID NO:18:

(i) SEQUENCE CHARACTERISTICS:
  (A) LENGTH: 80 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:18:

| Lys | Asn | Ser | Ser | Gly | Leu | Gly | Phe | Ser | Phe | Ser | Arg | Glu | Asp | Asn | Leu |
|---|---|---|---|---|---|---|---|---|---|---|---|---|---|---|---|
| 1 | | | | 5 | | | | | 10 | | | | | 15 | |
| Ile | Pro | Glu | Gln | Ile | Asn | Ala | Ser | Ile | Val | Arg | Val | Lys | Lys | Leu | Phe |
| | | | 20 | | | | | 25 | | | | | 30 | | |
| Ala | Gly | Gln | Pro | Ala | Ala | Glu | Ser | Gly | Lys | Ile | Asp | Val | Gly | Asp | Val |
| | | 35 | | | | | 40 | | | | | 45 | | | |
| Ile | Leu | Lys | Val | Asn | Gly | Ala | Ser | Leu | Lys | Gly | Leu | Ser | Gln | Gln | Glu |
| | 50 | | | | | 55 | | | | | 60 | | | | |
| Val | Ile | Ser | Ala | Leu | Arg | Gly | Thr | Ala | Pro | Glu | Val | Phe | Leu | Leu | Leu |
| 65 | | | | | 70 | | | | | 75 | | | | | 80 |

(2) INFORMATION FOR SEQ ID NO:19:

(i) SEQUENCE CHARACTERISTICS:
  (A) LENGTH: 72 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:19:

| Ser | Glu | Lys | Ala | Ser | Leu | Gly | Phe | Thr | Val | Thr | Lys | Gly | Asn | Gln | Arg |
|---|---|---|---|---|---|---|---|---|---|---|---|---|---|---|---|
| 1 | | | | 5 | | | | | 10 | | | | | 15 | |
| Ile | Gly | Cys | Tyr | Val | His | Asp | Val | Ile | Gln | Asp | Pro | Ala | Lys | Ser | Asp |
| | | | 20 | | | | | 25 | | | | | 30 | | |
| Gly | Arg | Leu | Lys | Pro | Gly | Asp | Arg | Leu | Ile | Lys | Val | Asn | Asp | Thr | Asp |
| | | 35 | | | | | 40 | | | | | 45 | | | |
| Val | Thr | Asn | Met | Thr | His | Thr | Asp | Ala | Val | Asn | Leu | Leu | Arg | Ala | Ala |
| | 50 | | | | | 55 | | | | | 60 | | | | |
| Ser | Lys | Thr | Val | Arg | Leu | Val | Ile |
| 65 | | | | | 70 | | |

(2) INFORMATION FOR SEQ ID NO:20:

(i) SEQUENCE CHARACTERISTICS:
  (A) LENGTH: 75 amino acids
  (B) TYPE: amino acid
  (C) STRANDEDNESS: single
  (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:20:

| Cys | Asn | Lys | Asx | Glu | Leu | Gly | Phe | Ser | Leu | Cys | Gly | Gly | His | Asp | Ser |
|---|---|---|---|---|---|---|---|---|---|---|---|---|---|---|---|

```
            1               5                    10                      15

Leu  Tyr  Gln  Val  Val  Tyr  Ile  Ser  Asp  Ile  Asn  Pro  Arg  Ser  Val  Ala
                       20                      25                      30

Ala  Ile  Glu  Gly  Asn  Leu  Gln  Leu  Leu  Asp  Val  Ile  His  Tyr  Val  Asn
                  35                      40                      45

Gly  Val  Ser  Thr  Gln  Gly  Met  Thr  Leu  Glu  Glu  Val  Asn  Arg  Ala  Leu
             50                      55                      60

Asp  Met  Ser  Leu  Pro  Ser  Leu  Val  Leu  Lys  Ala
        65                       70                      75
```

( 2 ) INFORMATION FOR SEQ ID NO:21:

( i ) SEQUENCE CHARACTERISTICS:
        ( A ) LENGTH: 75 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:21:

```
        Asp  Glu  Asp  Gly  Lys  Pro  Gly  Phe  Asn  Leu  Lys  Gly  Gly  Val  Asp  Gln
        1                   5                        10                      15

Lys  Asn  Pro  Leu  Val  Val  Ser  Arg  Ile  Asn  Pro  Ser  Ser  Pro  Ala  Asp
                       20                      25                      30

Thr  Cys  Ile  Pro  Lys  Leu  Asn  Glu  Gly  Asp  Gln  Ile  Val  Leu  Ile  Asn
                  35                      40                      45

Gly  Arg  Asp  Ile  Ser  Glu  His  Thr  His  Asp  Gln  Val  Val  Met  Phe  Ile
             50                      55                      60

Lys  Ala  Ser  Arg  Glu  Ser  His  Ser  Arg  Glu  Leu
        65                       70                      75
```

( 2 ) INFORMATION FOR SEQ ID NO:22:

( i ) SEQUENCE CHARACTERISTICS:
        ( A ) LENGTH: 75 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:22:

```
        Asp  Glu  Asn  Gly  Arg  Phe  Gly  Phe  Asn  Val  Lys  Gly  Gly  Tyr  Asp  Gln
        1                   5                        10                      15

Lys  Met  Pro  Val  Ile  Val  Ser  Arg  Val  Ala  Pro  Gln  Thr  Pro  Ala  Asp
                       20                      25                      30

Leu  Cys  Val  Pro  Arg  Leu  Asn  Glu  Gly  Asp  Gln  Val  Val  Leu  Ile  Asn
                  35                      40                      45

Gly  Arg  Asp  Ile  Ala  Glu  His  Thr  His  Asp  Gln  Val  Val  Leu  Phe  Ile
             50                      55                      60

Lys  Ala  Ser  Cys  Glu  Arg  His  Ser  Gly  Glu  Leu
        65                       70                      75
```

( 2 ) INFORMATION FOR SEQ ID NO:23:

( i ) SEQUENCE CHARACTERISTICS:
    ( A ) LENGTH: 79 amino acids
    ( B ) TYPE: amino acid
    ( C ) STRANDEDNESS: single
    ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:23:

```
Arg Gly Asn Ser Gly Leu Gly Phe Ser Ile Ala Gly Gly Thr Asp Asn
 1               5                  10                  15
Pro His Ile Gly Thr Asp Thr Ser Ile Tyr Ile Thr Lys Leu Ile Ser
            20                  25                  30
Gly Gly Ala Ala Ala Ala Asp Gly Arg Leu Ser Ile Asn Asp Ile Ile
         35                  40                  45
Val Ser Val Asn Asp Val Ser Val Val Asp Val Pro His Ala Ser Ala
     50                  55                  60
Val Asp Ala Leu Lys Lys Ala Gly Asn Val Val Lys Leu His Val
 65                  70                  75
```

( 2 ) INFORMATION FOR SEQ ID NO:24:

( i ) SEQUENCE CHARACTERISTICS:
        ( A ) LENGTH: 83 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:24:

```
Lys Gly Gly Lys Gly Leu Gly Phe Ser Ile Ala Gly Gly Ile Gly Asn
 1               5                  10                  15
Gln His Ile Pro Gly Asp Asn Gly Ile Tyr Val Thr Lys Leu Thr Asp
            20                  25                  30
Gly Gly Arg Ala Gln Val Asp Gly Arg Leu Ser Ile Gly Asp Lys Leu
         35                  40                  45
Ile Ala Val Arg Thr Asn Gly Ser Glu Lys Asn Leu Glu Asn Val Thr
     50                  55                  60
His Glu Leu Ala Val Ala Thr Leu Lys Ser Ile Thr Asp Lys Val Thr
 65                  70                  75                  80
Leu Ile Ile
```

( 2 ) INFORMATION FOR SEQ ID NO:25:

( i ) SEQUENCE CHARACTERISTICS:
        ( A ) LENGTH: 73 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:25:

```
Lys  Gly  Pro  Gln  Gly  Leu  Gly  Phe  Asn  Ile  Val  Gly  Gly  Glu  Asp  Gly
  1              5                        10                        15

Gln  Gly  Ile  Tyr  Val  Ser  Phe  Ile  Leu  Ala  Gly  Gly  Pro  Ala  Asp  Leu
               20                       25                        30

Gly  Ser  Glu  Leu  Lys  Arg  Gly  Asp  Gln  Leu  Leu  Ser  Val  Asn  Asn  Val
          35                  40                        45

Asn  Leu  Thr  His  Ala  Thr  His  Glu  Glu  Ala  Ala  Gln  Ala  Leu  Lys  Thr
     50                       55                        60

Ser  Gly  Gly  Val  Val  Thr  Leu  Leu  Ala
 65                      70
```

(2) INFORMATION FOR SEQ ID NO:26:

(i) SEQUENCE CHARACTERISTICS:
        (A) LENGTH: 79 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:26:

```
Arg  Gly  Asn  Ser  Gly  Leu  Gly  Phe  Ser  Ile  Ala  Gly  Gly  Thr  Asp  Asn
 1              5                        10                        15

Pro  His  Ile  Gly  Asp  Asp  Pro  Ser  Ile  Phe  Ile  Thr  Lys  Ile  Ile  Pro
               20                        25                       30

Gly  Gly  Ala  Ala  Ala  Gln  Asp  Gly  Arg  Leu  Arg  Val  Asn  Asp  Ser  Ile
          35                  40                        45

Leu  Phe  Val  Asn  Glu  Val  Asp  Val  Arg  Glu  Val  Thr  His  Ser  Ala  Ala
     50                       55                        60

Val  Glu  Ala  Leu  Lys  Glu  Ala  Gly  Ser  Ile  Val  Arg  Leu  Tyr  Val
 65                      70                       75
```

(2) INFORMATION FOR SEQ ID NO:27:

(i) SEQUENCE CHARACTERISTICS:
        (A) LENGTH: 79 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:27:

```
Lys  Gly  Pro  Lys  Gly  Leu  Gly  Phe  Ser  Ile  Ala  Gly  Gly  Val  Gly  Asn
 1              5                        10                        15

Gln  His  Ile  Pro  Gly  Asp  Asn  Ser  Ile  Tyr  Val  Thr  Lys  Ile  Ile  Glu
               20                        25                       30

Gly  Gly  Ala  Ala  His  Lys  Asp  Gly  Arg  Leu  Gln  Ile  Gly  Asp  Lys  Ile
          35                  40                        45

Leu  Ala  Val  Asn  Ser  Val  Gly  Leu  Glu  Asp  Val  Met  His  Glu  Asp  Ala
     50                       55                        60

Val  Ala  Ala  Leu  Lys  Asn  Thr  Tyr  Asp  Val  Val  Tyr  Leu  Lys  Val
 65                      70                       75
```

( 2 ) INFORMATION FOR SEQ ID NO:28:

( i ) SEQUENCE CHARACTERISTICS:
        ( A ) LENGTH: 73 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:28:

```
Arg Gly Ser Thr Gly Leu Gly Phe Asn Ile Val Gly Gly Glu Asp Gly
 1               5                  10                      15
Glu Gly Ile Phe Ile Ser Phe Ile Leu Ala Gly Gly Pro Ala Asp Leu
             20                  25                  30
Ser Gly Glu Leu Arg Lys Gly Asp Gln Ile Leu Ser Val Asn Gly Val
         35                  40                  45
Asp Leu Arg Asn Ala Ser His Glu Gln Ala Ala Ile Ala Leu Lys Asn
     50                  55                  60
Ala Gly Gln Thr Val Thr Ile Ile Ala
 65                  70
```

( 2 ) INFORMATION FOR SEQ ID NO:29:

( i ) SEQUENCE CHARACTERISTICS:
        ( A ) LENGTH: 78 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:29:

```
His Arg Ala Pro Gly Phe Gly Ile Ala Ile Ser Gly Gly Arg Asp Asn
 1               5                  10                      15
Pro His Phe Gln Ser Gly Glu Thr Ser Ile Val Ile Ser Asp Val Leu
             20                  25                  30
Lys Gly Gly Pro Ala Asx Gly Gln Leu Gln Glu Asn Asn Arg Val Ala
         35                  40                  45
Met Val Asn Gly Val Ser Met Asp Asn Val Glu His Ala Phe Ala Val
     50                  55                  60
Gln Gln Leu Arg Lys Ser Gly Lys Asn Ala Lys Ile Thr Ile
 65                  70                  75
```

( 2 ) INFORMATION FOR SEQ ID NO:30:

( i ) SEQUENCE CHARACTERISTICS:
        ( A ) LENGTH: 68 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:30:

Arg Lys Asn Glu Glu Tyr Gly Leu Arg Pro Ala Ser His Ile Phe Val
1               5                       10                      15

Lys Glu Ile Ser Gln Asp Ser Leu Ala Ala Arg Asp Gly Asp Ile Gln
            20                  25                  30

Glu Gly Asp Val Val Leu Lys Ile Asn Gly Thr Val Thr Glu Asn Met
            35                  40                  45

Ser Leu Thr Asp Ala Lys Thr Leu Ile Glu Arg Ser Lys Gly Lys Leu
    50                  55                  60

Lys Met Val Val
65

(2) INFORMATION FOR SEQ ID NO:31:

(i) SEQUENCE CHARACTERISTICS:
(A) LENGTH: 71 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:31:

Arg Lys Gly Asp Ser Val Gly Leu Arg Leu Ala Gly Gly Asn Asp Val
1               5                       10                      15

Gly Ile Phe Val Ala Gly Val Leu Glu Asp Ser Pro Ala Ala Lys Glu
            20                  25                  30

Gly Leu Glu Glu Gly Asp Gln Ile Leu Arg Val Asn Asn Val Asp Phe
            35                  40                  45

Thr Asn Ile Ile Arg Glu Glu Ala Val Leu Phe Leu Leu Asp Leu Pro
    50                  55                  60

Lys Gly Glu Glu Val Thr Ile
65              70

(2) INFORMATION FOR SEQ ID NO:32:

(i) SEQUENCE CHARACTERISTICS:
(A) LENGTH: 72 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:32:

Val Thr Glu Glu Pro Met Gly Ile Thr Leu Lys Leu Asn Glu Lys Gln
1               5                       10                      15

Ser Cys Thr Val Ala Arg Ile Leu His Gly Gly Met Ile His Arg Gln
            20                  25                  30

Gly Ser Leu His Val Gly Asp Glu Ile Leu Glu Ile Asn Gly Thr Asn
            35                  40                  45

Val Thr Asn His Ser Val Asp Gln Leu Gln Lys Ala Met Lys Glu Thr
    50                  55                  60

Lys Gly Met Ile Ser Leu Lys Val
65              70

( 2 ) INFORMATION FOR SEQ ID NO:33:

( i ) SEQUENCE CHARACTERISTICS:
      ( A ) LENGTH: 74 amino acids
      ( B ) TYPE: amino acid
      ( C ) STRANDEDNESS: single
      ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:33:

| Arg | Lys | Val | Gly | Gly | Leu | Gly | Phe | Leu | Val | Lys | Glu | Arg | Val | Ser | Pro |
| 1 | | | | 5 | | | | | 10 | | | | | 15 | |
| Lys | Lys | Pro | Val | Ile | Ile | Ser | Asp | Leu | Ile | Arg | Gly | Gly | Ala | Ala | Glu |
| | | | 20 | | | | | 25 | | | | | 30 | | |
| Gln | Ser | Gly | Leu | Ile | Gln | Ala | Gly | Asp | Ile | Ile | Leu | Ala | Val | Asn | Asp |
| | | 35 | | | | | 40 | | | | | 45 | | | |
| Arg | Pro | Leu | Val | Asp | Leu | Ser | Tyr | Asp | Ser | Ala | Leu | Glu | Val | Leu | Arg |
| | 50 | | | | | 55 | | | | | 60 | | | | |
| Gly | Ile | Ala | Ser | Glu | Thr | His | Val | Val | Leu |
| 65 | | | | | 70 | | | | |

( 2 ) INFORMATION FOR SEQ ID NO:34:

( i ) SEQUENCE CHARACTERISTICS:
      ( A ) LENGTH: 74 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:34:

| Glu | Asp | His | Glu | Gly | Leu | Gly | Ile | Ser | Ile | Thr | Gly | Gly | Leu | Glu | His |
| 1 | | | | 5 | | | | | 10 | | | | | 15 | |
| Gly | Val | Pro | Ile | Leu | Ile | Ser | Gly | Ile | His | Pro | Gly | Gln | Pro | Ala | Asp |
| | | | 20 | | | | | 25 | | | | | 30 | | |
| Arg | Cys | Gly | Gly | Leu | His | Val | Gly | Asp | Ala | Ile | Leu | Ala | Val | Asn | Gly |
| | | 35 | | | | | 40 | | | | | 45 | | | |
| Val | Asn | Leu | Arg | Asp | Thr | Leu | His | Leu | Gly | Ala | Val | Thr | Ile | Leu | Ser |
| | 50 | | | | | 55 | | | | | 60 | | | | |
| Gln | Gln | Arg | Gly | Glu | Ile | Glu | Phe | Glu | Val |
| 65 | | | | | 70 | | | | |